US009687553B2

(12) United States Patent
Almutairi et al.

(10) Patent No.: US 9,687,553 B2
(45) Date of Patent: *Jun. 27, 2017

(54) POLYMERIC NANOCARRIERS WITH LINEAR DUAL RESPONSE MECHANISM

(71) Applicant: The Regents of the University of California, Oakland, CA (US)

(72) Inventors: Adah Almutairi, La Jolla, CA (US); Jagadis Sankaranarayanan, San Diego, CA (US); Enas Mahmoud, San Diego, CA (US); Eric Schopf, Solana Beach, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 218 days.

This patent is subject to a terminal disclaimer.

(21) Appl. No.: 14/272,429

(22) Filed: May 7, 2014

(65) Prior Publication Data
US 2015/0079005 A1 Mar. 19, 2015

Related U.S. Application Data

(63) Continuation of application No. 13/234,969, filed on Sep. 16, 2011, now Pat. No. 8,758,778.

(60) Provisional application No. 61/383,340, filed on Sep. 16, 2010.

(51) Int. Cl.
A61K 49/06 (2006.01)
A61K 31/711 (2006.01)
A61K 38/02 (2006.01)
C12N 5/071 (2010.01)
A61K 47/34 (2006.01)
C08G 69/40 (2006.01)
A61K 49/00 (2006.01)
A61K 9/51 (2006.01)
A61K 49/12 (2006.01)
A61K 49/18 (2006.01)
B82Y 5/00 (2011.01)
B82Y 15/00 (2011.01)
B82Y 30/00 (2011.01)
B82Y 40/00 (2011.01)
C08G 63/672 (2006.01)
C08G 63/685 (2006.01)
C08G 63/688 (2006.01)
C08G 73/06 (2006.01)
A61K 48/00 (2006.01)
C12N 15/87 (2006.01)
A61K 31/713 (2006.01)
A61K 38/16 (2006.01)
A61K 9/19 (2006.01)

(52) U.S. Cl.
CPC ............ *A61K 47/34* (2013.01); *A61K 9/5153* (2013.01); *A61K 31/713* (2013.01); *A61K 38/16* (2013.01); *A61K 48/0041* (2013.01); *A61K 49/0093* (2013.01); *A61K 49/126* (2013.01); *A61K 49/128* (2013.01); *A61K 49/1818* (2013.01); *B82Y 5/00* (2013.01); *B82Y 15/00* (2013.01); *B82Y 30/00* (2013.01); *B82Y 40/00* (2013.01); *C08G 63/672* (2013.01); *C08G 63/6856* (2013.01); *C08G 63/6886* (2013.01); *C08G 73/0627* (2013.01); *C12N 15/87* (2013.01); *A61K 9/19* (2013.01)

(58) Field of Classification Search
None
See application file for complete search history.

(56) References Cited

U.S. PATENT DOCUMENTS

| 6,471,968 B1 | 10/2002 | Baker, Jr. et al. |
| 7,018,624 B2 | 3/2006 | Harris |
| 8,758,778 B2 | 6/2014 | Almutairi et al. |
| 8,828,383 B2 | 9/2014 | Almutairi et al. |
| 2005/0265961 A1* | 12/2005 | Langer ............ A61K 47/48192 424/78.36 |
| 2005/0271615 A1 | 12/2005 | Shabat et al. |
| 2006/0069230 A1 | 3/2006 | Papisov |
| 2006/0269480 A1 | 11/2006 | Amir et al. |
| 2007/0009980 A1 | 1/2007 | Graham et al. |
| 2007/0148074 A1 | 6/2007 | Sadoqi et al. |
| 2009/0233359 A1 | 9/2009 | Kwon |

FOREIGN PATENT DOCUMENTS

WO 2004019993 A1 3/2004

OTHER PUBLICATIONS

Wilson, D.S. et al., "Orally delivered thioketal nanoparticles loaded with TNF-α-siRNA target inflammation and inhibit gene expression in the intestines", 2009, Nature Materials, pp. 923-928.
Alexis, F., et al., "HER-2-Targeted Nanoparticle-Affibody Bioconjugates for Cancer Therapy", 2008, Cem MedChem, pp. 1839-1843.
Xu, L., et al, "Effects of Temperature and pH on the Degradation of Poly(lactic acid) Brushes", 2011, Macromolecules, pp. 4777-4782.
Andersson, L., et al., "Poly(ethylene glycol)-Poly(ester-carbonate) Block Copolymers Carrying PEG-Peptidyl-Doxorubicin Pendant Side Chains: Synthesis and Evaluation as Anticancer Conjugates", 2005, Biomacromolecules, pp. 914-926.

(Continued)

Primary Examiner — Michael G Hartley
Assistant Examiner — Lance Rider
(74) Attorney, Agent, or Firm — Eleanor Musick; Musick Davison LLP

(57) ABSTRACT

Nanocarriers are synthesized with polymers that respond to lower pH and/or ROS by being degraded. The compositions may be utilized to selectively deliver payloads within patients by responding to lower pH and/or ROS at localities within the patient. The present invention also features methods of synthesizing nanocarriers that are degraded by lower pH and/or ROS.

20 Claims, 43 Drawing Sheets

(56) References Cited

OTHER PUBLICATIONS

Sankaranarayanan, J., et al., "Multiresponse Strategies to Modulate Burst Degradation and Release from Nanoparticles", 90/90/2010, ACS Nano, pp. 5930-5936.
Mahmoud, E.A., et al., "Inflammation Responsive Logic Gate Nanoparticles for the Delivery of Proteins", 2011, Bioconjugate Chem., 22, pp. 1416-1421.
Fomina, N., et al., "UV and Near-IR triggered release from polymeric nanoparticles", Jul. 21, 2010, J Am Chem Soc., 132(28): 9540-9542.
Huotari, J., et al., "Endosome Maturation", 2011, The EMBO Journal, (30) 3481-3500.
Sagi, A., et al., "Self-Immolative Polymers", 2008, J. Am Chem Soc., 130(16): 5434-5435.
Kneipp, J., et al., "Two-photon vibrational spectroscopy for biosciences based on surface-enhanced hyper-Raman scattering", 2006, PNAS, (103(46): 17149-17153.
Furuta, T., et al., "Brominated 7-hydroxycoumarin-4-ymethyls: Photolabile protecting groups with biologically useful cross-sections for two photon photolysis", 1999, PNAS vol. 96, pp. 1193-1200.
Gil, P.R., et al., "Composite Nanoparticles Take Aim at Cancer", 2008, ACS Nano, 2(11):2200-2205.
Amir, R.J., et al., "Prodrug Activation Gated by a Molecular "OR" Logic Trigger", 2005, Angew. Chem. Int. Ed., vol. 44, pp. 2-4.
Flomenbom, O., et al., "Some new aspects of dendrimer applications", 2005, J. Luminescent, vol. 111, pp. 315-325.
Bedard, M. F., et al., "Polymeric microcapsules with light responsive properties of encapsulation and release", 2010, Advances in Colloid and Interface Science, vol. 158, pp. 2-14.
Bedard, M.F., et al., "Toward Self-Assembly of Nanoparticles on Polymeric Microshells: Near-IR Release and Permeability", 2008, ACS Nano; 2(9): 1807-1816.
Medina, S.H., et al., "Dendrimers as Carriers for Delivery of Chemotherapeutic Agents", 2009, Chem. Rev., 109, pp. 3141-3157.
Singh, S.K., et al., "Dendrimer a versatile polymer in drug discovery", 2009, Asian J Pharm., 3:178-187.
Sopczynski, B.P., "A New Anti-Tumor Drug Delivery System: Dendrimers", 2008, MMG 445 Basic Biotechnology eJournal, 2:87-92.
Weinstain, R., et al., "Self-Immolative Comb-Polymers: Multiple-Release of Side-Reporters by a Single Stimulus Event", 2008, Chem. Eur. J., 14:6857-6861.
Crampton, H.L., et al., "Dendrimers as drug delivery vehicles: non-covalent interactions of bioactive compounds with dendrimers", Mar. 2, 2007, Polym. Int., 56(4): 489-496.
Haba, K., et al., Single-Triggered Trimeric Prodrugs, Angew. Chem. 2005, 117, 726-730.
Goodwin, A.P., et al., "Synthetic Micelle Sensitive to IR Light via a Two-Photon Process", J. Am. Chem. Soc. 2005, 127, 9952-9953, published online Jun. 25, 2005.
Mynar, J.L., et al., "Two-photon degradable supramolecular assemblies of linear-dendritic copolymers", Chem Commun. (Camb.) 2007, 2081-2082.
Jourden, J.L.M. And Cohen, S.M., "Hydrogen Peroxide Activated Matrix Metalloproteinase Inhibitors: A Prodrug Approach," Angew Chem Int Ed Engl., Sep. 10, 2010; 49(38):6795-6797.
Jourden, J.L.M., et al., "Investigation of self-immolvative linkers in the design of hydrogen peroxide activated metalloprotein inhibitors", Chem Commun. (Camb.) Jul. 28, 2011; 47(28):7968-7970.
Murthy, N., et al., "A macromolecular delivery vehicle for protein-based vaccines: Acid-degradable protein-loaded microgels", Proc. Nat. Acad. Sci. (PNAS) Apr. 29, 2003; 100(9):4995-5000.
Van de Bittner, G., et al., "In vivo imaging of hydrogen peroxide production in a murine tumor model with chemoselective bioluminescent reporter", Proc. Nat. Acad. Sci. (PNAS); Dec. 14, 2010; 107(50):21316-21321.
Wang, W., et al., "Self-Immolative Polymers", Angew. Chem Int'l. Ed.; 2008, 47; 7804-7806.
Makadia, H.K., et al., "Poly Lactic-co-Glycolic Acide (PLGA) as Biodegradable Controlled Drug Delivery Carrier," Polymers 2011, 3:1377-1379.

* cited by examiner

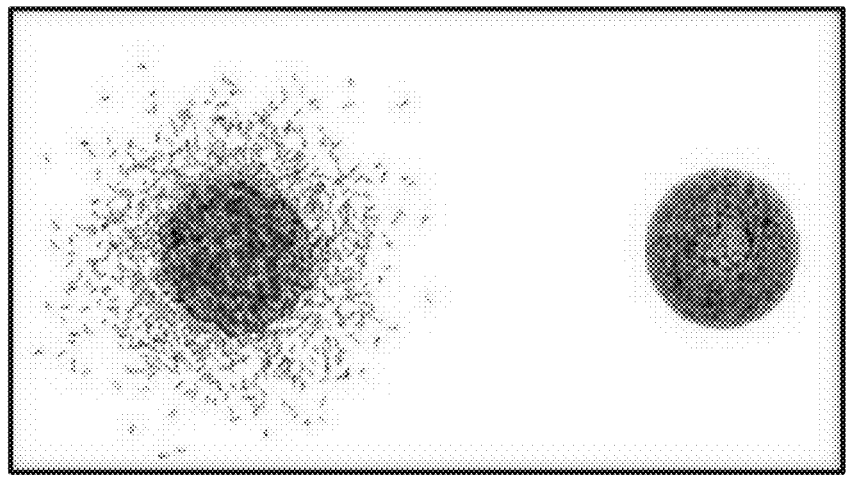
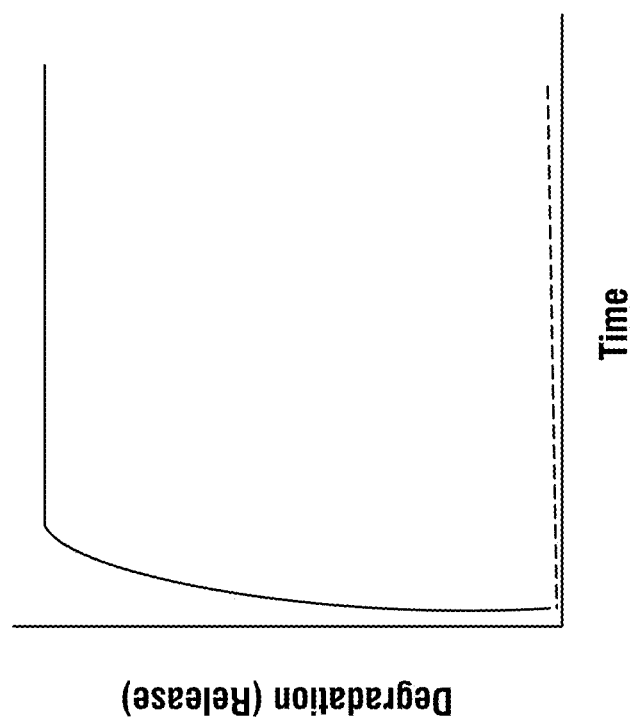
FIG. 3

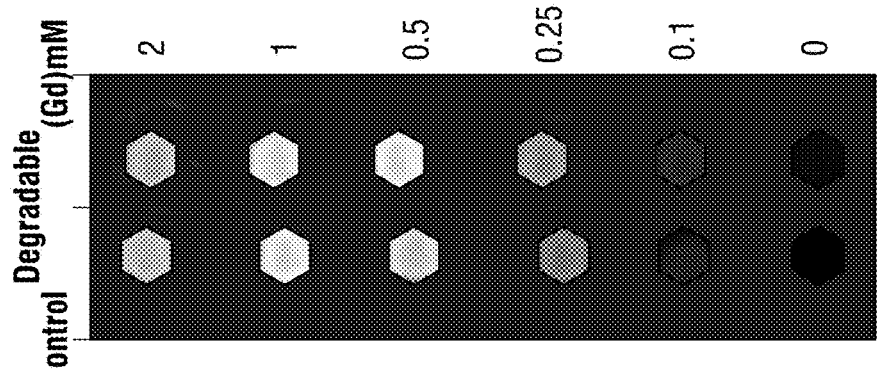
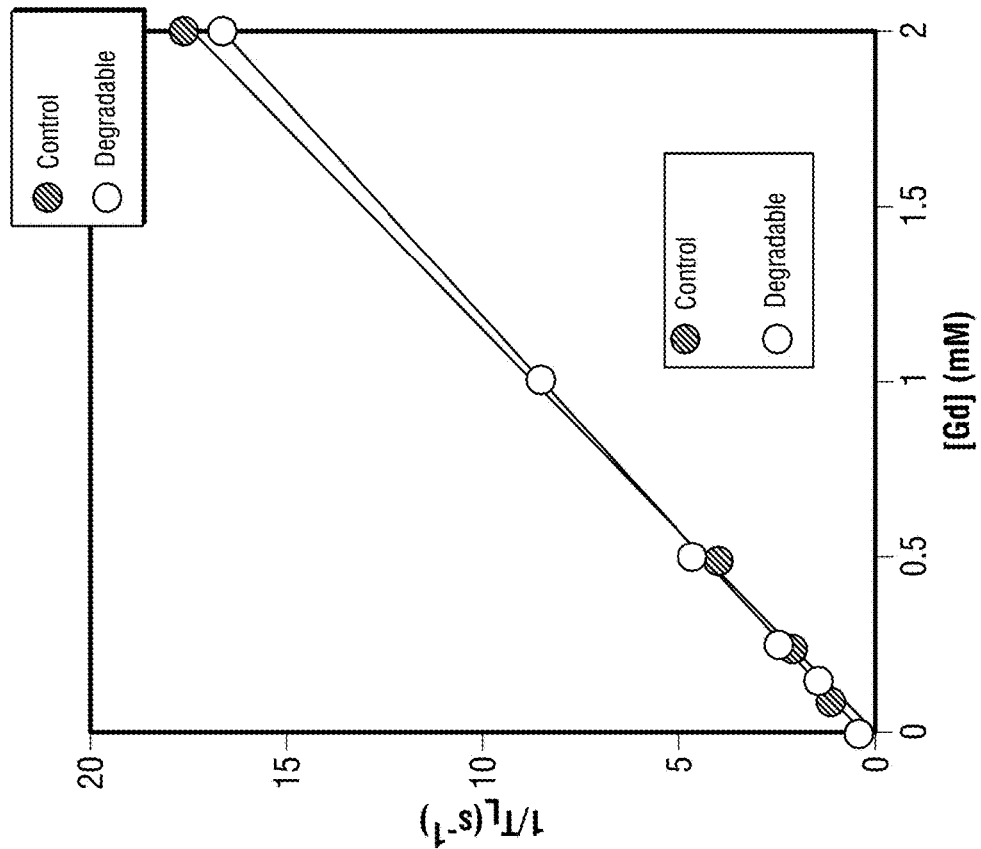
FIG. 28B
FIG. 28A

POLYMERIC NANOCARRIERS WITH LINEAR DUAL RESPONSE MECHANISM

RELATED APPLICATIONS

This is a continuation of application Ser. No. 13/234,969, filed Sep. 16, 2011, which claims the benefit of the priority of U.S. Provisional Application No. 61/383,340 filed Sep. 16, 2010, the disclosure of which is incorporated herein by reference in its entirety.

GOVERNMENT RIGHTS

This invention was made with government support under Grant OD006499 awarded by the National Institutes of Health. The government has certain rights in the invention.

FIELD OF THE INVENTION

The present invention relates to nanocarriers and methods for synthesizing nanocarriers. The present invention also relates to methods of enclosing, then releasing to localized areas in living systems, compounds of interest via the nanocarriers of the present invention.

Nanoparticle Packaging

The emerging technology of nanoparticles packaging offers a way to package and deliver compounds of interest that offers advantages to the practitioner. Nanoparticles can be synthesized and/or assembled so as to enclose other compounds of interest. Thus, nanoparticles can serve to protect compounds of interest by sequestration and/or encapsulation. Nanoparticulate media involved in this approach include nano- and microgels, nano- and microspheres, polymer micelles, and polymerized liposomes. Retention of the active compound in the nanocarriers is achieved by physical entrapment or by thermodynamic forces such as hydrophobic interactions. The use of microbeads with a slowly degradable shell, for example of poly-β-aminoesters or poly-orthoesters is described in the literature. Such microspheres are conveniently prepared from a pre-formed polymer using a water-oil-water double emulsion method. Similarly, a number of pre-formed hydrophobic polymers can be used to encapsulate hydrophobic drugs or hydrophilic macromolecules in processes known as nanoprecipitation and double emulsion condensation (DEC).

Non-limiting examples of compounds of interest in the present invention include bioactive agents, pharmaceutical agents, or imaging agents, and deliver them to an area of interest, such as tumor tissue. Nanoparticles may be then signaled to release their contents via externally-applied signals and/or signals present at the area of interest. In some examples, nanoparticles may be delivered systematically to a patient, while releasing of the contents of the nanoparticle at a focused area of interest within a living organism. Non-limiting examples of the contents of nanoparticles, i.e., payloads, include pharmaceutical agents, drugs, antibodies, and/or labeling compounds.

Nanoparticle packaging can also improve the effectiveness of bioactive agents and/or pharmaceutical agents. In some nanoparticle designs, the serum stability of bioactive agents and/or pharmaceutical agents can be enhanced and solubility limitations bypassed. Thus, nanoparticle packaging circumvents the vulnerability of bioactive agents and/or pharmaceutical agents, for example, to a reduction in efficacy due to bioavailability problems, e.g., solubility and/or stability. Moreover, such carriers can also serve to minimize undesirable side effects by reducing systemic exposure to drugs and/or by decreasing their necessary dosage. In addition, encapsulating bioactive agents and/or imaging agents may protect them from sequestration and/or renal clearance.

Nanoparticles also offer the potential, at least, for targeted delivery of their payloads to specific areas of interest within a patient. For example, an affinity reagent attached externally to nanoparticles enables an increase the concentration of such nanoparticles at their intended location. An example of such an affinity reagent is an antibody. Modifying the nanoparticles, and not the payload itself, avoids direct modification of the enclosed bioactive agent while improving its targeting and therefore obviates concerns about changing the activity of the bioactive agent.

Nanoparticles may be designed to be capable of a controlled and rapid triggered response to physiological events and/or conditions. Such physiological events and/or conditions may include changes in extracellular pH, temperature and reactive oxygen species. Therefore, nanoparticles capable of such a triggered response may be useful in the delivery of therapeutics and diagnostics to diseased cells and tissue. (See, e.g., Farokhzad, et al., (2006) *Expert Opinion on Drug Delivery*, 3, 311-324; Farokhzad & Langer (2009) *ACS Nano*, 3, 16-20; Ferrari, (2005) *Nat. Rev. Cancer* 5, 161-171; Ganta, et al., (2008) *J. Control. Release*, 126, 187-204; Langer (1990) *Science*, 249, 1527-33; LaVan, et al. (2003) *Nat. Biotechnol.* 21, 1184-1191; Whitesides (2003) *Nat. Biotechnol.* 21, 1161-1165; and Zhang et al. (2008) *Clinical Pharmacology and Therapeutics*, 83, 761-9).

Additionally, encapsulation within nanoparticles constructed from biodegradable polymers can allow bioactive agents to be delivered to the cytosol of diseased cells via endosomes and cytosolic release (Lewis (1990) Drugs and the Pharmaceutical Sciences, Vol. 45: Biodegradable Polymers as Drug Delivery Systems, Chasin & Langer, Eds.; Marcel Dekker, pp 1-42; Panyam & Labhasetwar (2003) *Adv. Drug Delivery. Rev.*, 55, 329-347; and Shenoy, et al. (2005) *Pharm. Res.*, 22, 2107-14.). Cytosolic delivery is particularly challenging and can be a major hurdle for effective therapeutic delivery (Vasir & Labhasetwar (2007) *Adv. Drug Delivery. Rev.*, 59, 718-728; and Mescalchin et al. (2007) *Expert Opin. Biol. Ther.*, 7, 1531-1538). Burst-degrading drug delivery systems hold promise in achieving increased cytosolic release through elevated osmotic pressure within the endosomes (Sonawane, et al. (2003) *J. Biol. Chem.* 2003, 278, 44826-31; and Hu, et al. (2007) *Nano Lett.* 7, 3056-64).

In the past, nanoparticles have been developed from hydrogels utilizing ketal crosslinks. However the payloads of such nanoparticles are usually limited to large water-soluble macromolecules. Unfortunately, with nanoparticles such as these, significant unwanted degradation occurs at physiological pH values over time (Cohen, et al. (2008) *Bioconjug. Chem.*, 19, 876-81). Similarly, hydrophobic polyketals can encapsulate both hydrophobic and hydrophilic payloads, however, as nanoparticles they no longer undergo rapid acid catalyzed hydrolysis unless fully hydrated (Yang, et al. (2008) *Bioconjug. Chem.*, 19, 1164-1169).

Formulation of nanoparticles from polymers may provide them with a hydrophobic character. However, this dramatically slows down their hydrolysis degradation kinetics as degradation only occurs slowly by a surface erosion mechanism (Heffernan, et al. (2009) *Biomaterials*, 30, 910-918; Heffernan & Murthy (2005) *Bioconjug. Chem.*, 16, 1340-1342; Paramonov, et al. (2008) *Bioconjug. Chem.*, 19, 911-919).

There is growing interest in polymeric biomaterials that can be remotely disassembled in a controlled fashion with an external stimulus, but are otherwise stable under physiological conditions (Wang, W.; Alexander, C. *Angew. Chem. Int. Ed.,* 2008, 47, 7804-7806). Various internal and external stimuli, such specific enzymes, temperature, ultrasound, and electromagnetic radiation have been exploited as release mechanisms. (See, e.g., Veronese, et al. (2005) *Bioconjugate Chem.* 16, 775-784; Chung, et al. (1999) *Controlled Release,* 62 (1-2), 115-27; Liu, et al. (2005) *Biomaterials,* 26, 5064-5074; Na, et al. (2006) *Eur. J. Pharm. Sci.,* 27, 115-122; Gao, et al. (2005) *Controlled Release,* 102, 203-22; Nelson, et al. (2002) *Cancer Research,* 62, 7280-83); and PCT Publication WO 2011/038117 A2, Almutairi et al.)

As noted above, one approach to nanoparticle targeting utilizes pH-dependent triggering. (See, e.g., Murthy, et al. (2003) *Proc. Natl. Acad. Sci. U.S.A.,* 100, 4995-5000.) However, current pH-activated polymers created for this approach to nanoparticle synthesis and delivery still produce unfavorable side effects from unwanted interactions with other parts of a patient's body. For example, such materials used for drug delivery are predominantly based on polyesters, and polyesters are potentially problematic for treating inflammatory diseases because of their slow hydrolysis kinetics and acidic degradation products. The acidic degradation products have been observed to frequently cause inflammation (Anderson, J. M., Shive, M. S. (1997) *Advanced Drug Delivery Reviews,* 28, 5-24 (1997)). A more recent approach relies on other release mechanisms to target disease-state tissues and achieve the controlled the release of nanoparticle payload, however release still occurs at a significant level in healthy tissue (Murthy, et al. (2003) *Proc. Natl. Acad. Sci. U.S.A.,* 100, 4995-5000.)

Poly-β-aminoesters, (PbAE), among pH sensitive polymers which are able to switch from hydrophobic to hydrophilic, are widely studied because of their excellent tunability (Akinc, et al. (2003) *Bioconjug. Chem.* 14, 979-88; Kohane, et al. (2006) *J Biomed Mater Res A* 77, 351-61; Lynn, et al. (2006) *Angew Chem Int Ed Engl* 40, 1707-1710; Lynn, et al. (2001) *J. Am. Chem. Soc.* 123, 8155-6; and Lynn & Langer (2000) *J. Am. Chem. Soc.* 122, 10761-10768) and ease of preparation (Lynn, et al. (2001) *J. Am. Chem. Soc.* 123, 8155-6; Anderson, et al. (2003) *Angew. Chem., Int. Ed.* 42, 3153-3158). Hydrophobic nanoparticles made of PbAE undergo protonation of the amine backbone upon decreasing the pH, leading to immediate dissolution in aqueous solutions (Hofmann, et al. (2009) *Adv. Mater.* 21, 3237-3245; Smith, et al. (2009) *Chem. Mater.* 21, 1108-1115; Zhang, et al. (2006)—*Langmuir* 22, 239-245; and Zhong, et al. (2005) *J. Control. Release* 109, 317-329).

Targeting Inflammation

Inflammation, especially chronic, is associated with several diseases, including cancer and cardiovascular disease. Although there are numerous reports of 'smart' nanoparticles that rapidly and selectively respond to different disease specific stimuli, there is a dearth of nanoparticles capable of specifically targeting inflammation. Furthermore, nanoparticles capable of cytoplasmic delivery are particularly challenging and this remains a major hurdle for effective therapeutic delivery. In achieving increased cytoplasmic delivery, burst-fragmenting nanoparticles hold promise as they can lead to elevated osmotic pressure within the endosome leading to endosomal escape of the nanoparticles payload (Hu, et al. (2007) Cytosolic delivery of membrane-impermeable molecules in dendritic cells using pH-responsive core-shell nanoparticles, Nano Lett. 7, 3056-3064; Sankaranarayanan, et al. (2010) Multi-response strategies to modulate burst degradation and release from nanoparticles. ACS Nano 4, 5930-5936; and Sonawane, et al. (2003) Chloride accumulation and swelling in endosomes enhances DNA transfer by polyamine-DNA polyplexes. J. Biol. Chem. 278, 44826-31).

Important biomarkers of diseased tissue that have been successfully used to trigger nanoparticle degradation include reduced extracellular pH, thermal responsiveness, reductive microenvironments, and oxidative stress. Although these nanoparticles respond to a single disease stimulus, control over the degradation kinetics, and thus the ON/OFF state of the system, has been difficult to achieve. For example, polyketals have gained prominence as the choice of drug delivery nanoparticles owing to their rapid pH response (Paramonov, et al., (2008) *Bioconjugate Chem.* 19, 911-19; Heffernan & Murthy (2005) *Bioconjugate Chem.* 16, 1340-2; Broaders, et al., (2009) *Proc. Natl. Acad. Sci. U.S.A.* 106, 5497-5502.). Nanoparticles formulated from these polyketals can degrade at acidic pH into acetone and other benign molecules, and can rapidly releasing their payload to the cytoplasm.

However, a key drawback of these systems is that as hydrophobic polymeric nanoparticles their degradation rates are very slow (many days) in acidic pH (pH 6-5) because of reduced water influx. Although a hydrophobic backbone is advantageous in formulating stable nanoparticles at physiological conditions, a hydrophilic backbone is needed to produce fast release in targeted tissue. On the other hand, a hydrophilic backbone often results in nanoparticles that are not stable in pH 7.4 for longer than a few hours.

Others have developed polysulfides that have been used to formulate oxidation-sensitive vesicles (Napoli et al. (2004) *Nature Materials* 3, 183-189) and nanoparticles (Rehor, et al. (2005) *Oxidation-Sensitive Polymeric* nanoparticles, *Langmuir* 21, 411-417), with such nanoparticles also being used to selectively target dendritic cells in vivo (Reddy, et al. (2006) *J of Controlled Release* 112, 26-34).

Gene Delivery

Emerging gene delivery tools offer novel therapeutic approaches to address several types of diseases including Progeria, Cystic Fibrosis, Parkinson's, and multiple types of cancers. Gene therapy encompasses the entire process of effectively delivering functional DNA into cells to replace a missing or mutated gene within malfunctioning cells. One of the main challenges with gene delivery is that free DNA circulating in the body is exposed to nuclease degradation. Additional obstacles for gene delivery include the inability of DNA to cross the cell membrane, escape the endosome, and enter the nucleus, due to the DNA's size and negative charge.

Recent advances using virus-mediated delivery of DNA have been promising due to their high transfection efficiencies and high expression rates. However, viral delivery systems face several fundamental problems associated with viral vector systems, including toxicity, immunogenicity, and manufacturing costs.

Non-viral polymeric systems offer an attractive alternative to deliver plasmid DNA and other nucleic acid molecules like siRNA. However, polymeric systems must overcome various steps leading to gene expression. In order to promote high efficiency of gene delivery, DNA must escape from the endosome before degrading within the late endosome and lysosome. A method that is widely used to promote endosomal lysis is to include chloroquine within the formulation to enhance gene expression. A drawback of chloroquine, however, is that it can disrupt potentially all the endosomes and lysosomes in the cell. Advances in cationic polymers such as poly(L-lysine) (PLL) and polyethyleneimine (PEI), PAMAM dendrimers, and chitosan have shown some promise in complexing DNA into polyplexes and used for DNA delivery in vivo. The positively charged complexes allow binding and entry into the negatively charged cell membrane. Additionally, the large number of amino groups in PEI and other polymers offers a buffering effect in the low pH environment of the endosome and creates the "proton sponge effect" leading to endosomal burst and release of the DNA complex into the cytoplasm to produce higher transfection efficiencies.

Due to toxicity and relatively poor stability of polyplexes, nano- and microparticles provide an alternative method for delivery. Nanoparticles offer superior protection from circulating nuclease activity and offer an array of possible targeting advantages when combined with specific peptides. Nanoparticles composed of synthetic polymers such as poly(lactic-co-glycolic acid) (PLGA) are safe and attractive methods for DNA delivery applications and have been used in several studies. Encapsulation of DNA with PLGA protects it from nuclease degradation, but the DNA is released slowly over time as PLGA degrades through ester hydrolysis. An additional limitation of using PLGA nanoparticles is their negative charge that must usually be modified to become more compatible for DNA encapsulation and delivery.

Molecular Imaging

Molecular imaging, as distinct from structural (anatomic) or functional imaging, is a nascent field that aims to characterize and quantify cellular and sub-cellular events in intact organisms non-invasively (Weissleder & Mahmood (2001) *Radiology* 219, 316-333).

Aspects of such imaging include imaging physiological conditions, such as pH or the presence of reactive oxygen species, as well as diseases, such as tumors or areas of inflammation. Current medical imaging technology is generally limited to the detection of late structural manifestations of disease, not the molecular events that underlie disease.

MRI exploits the abundance of water in vivo, has no radiative burden, and is very versatile. FIGS. 1A and 1B provide an illustration of how MRI works and the parameters that govern the strength of MRI contrast agents. MRI resolution can be improved through the use of gadolinium-based contrast agents.

Imaging agents, such as small molecule gadolinium chelates, offer enhanced contrast in Magnetic Resonance Imaging (MRI). These particular agents are also rapidly cleared by a healthy renal system, thus posing little risk of demetallation and its accompanying gadolinium-associated toxicity. Many gadolinium contrast agents (Gd-CAs) are currently approved by the FDA and are used in over 25-30% of MRI imaging procedures. However, the same rate of clearance of these small molecule chelates reduces their bioavailability in many tissues below an optimal level.

Additionally, these Gd-CAs are not perfect MRI contrast agents because their relaxivity is low. Therefore, in spite of their popularity, their contrasting ability could be improved. Macromolecular-based gadolinium contrast agents such as polymers and dendrimers enjoy higher molecular relaxivities and are thus promising candidates for use as contrasting agents. This is due in part to the slower tumbling frequency of macromolecules, and due in part to the higher loading of gadolinium atoms per macromolecule, as well as increased tissue permeability.

Unfortunately, despite these promising properties of this latter class of macromolecular Gd-CAs, they have not been approved due to toxicity concerns. These concerns stem from both in vivo animal studies and human studies that found gadolinium accumulation in tissue, organs, and even bones after administration. Further studies demonstrated that the slower clearance of macromolecular CAs allow for more gadolinium to be dissociated and accumulate in the body where they could transmetallate.

Non-invasive spectroscopic approaches for measuring pH mostly rely on endogenous and/or exogenous monovalent molecular probes that are weak acids or bases with pH-dependable spectral properties (Gillies, et al. (2004) *IEEE Engineering in Medicine and Biology Magazine* 23, 57-64).

ROS

As noted, supra, infected tissues are frequently characterized by a decreased pH and the presence of reactive oxygen species (ROS). A recent approach to selectively visualize $H_2O_2$ is to use the chemoselective hydrogen-peroxide-mediated transformation of arylboronates to phenols to activate small molecule contrast probes that fluoresce in the visible region of the electromagnetic spectrum and are thus applicable in vitro (Chang, et al. (2004) *J. Am. Chem. Soc.* 126, 15392-15393).

SUMMARY OF THE INVENTION

In one aspect, the present invention features a composition comprising a logic gate nanocarrier wherein the logic gate nanocarrier comprises at least one polymer, or a plurality of polymers, or a multiplicity of polymers, and wherein the polymer comprises at least one response element and wherein the response element can respond to lower pH and/or ROS.

In some embodiments of this aspect, the logic gate nanocarrier comprises a molecularly engineered polymer of the present invention. In some embodiments, the polymer features a structural element, also known as a response element, which renders the polymer capable of responding to some feature of its environment such as pH or the presence of ROS. In some embodiments, such a response can result in the polymer, as well as the logic gate nanocarrier becoming more hydrophilic. In some embodiments, the logic gate nanocarrier becomes more hydrophilic in response to lower pH; in some embodiments, the logic gate nanocarrier becomes more hydrophilic in response to ROS.

In some embodiments, a response to, for example, lower pH or ROS, can result in the polymer become cleaved, as well as causing the overall degradation of the logic gate nanocarrier. In some embodiments of this aspect, the polymer can respond to both pH and ROS via separate structural elements. In these embodiments, a polymer may have more than one type of response elements; in a non-limiting example, each polymer subunit may have two response elements. In some embodiments, the response element is a ketal group. In some embodiments, the response element is a sulfur atom within the polymer. In many embodiments, the logic gate nanocarrier of the present invention is stable under normal physiological conditions.

In many embodiments of this aspect, the logic gate nanocarrier comprises a payload. The payload may comprise bioactive agents; and may further comprise more than one type of bioactive agents. Such bioactive agents may include, but is not restricted to, drugs or imaging agents. Such imaging agents may include, but is not restricted to, MRI imaging agents. Such MRI imaging agents may include gadolinium-based MRI imaging agents.

In various aspects of the invention, the polymers comprise a monomer selected from

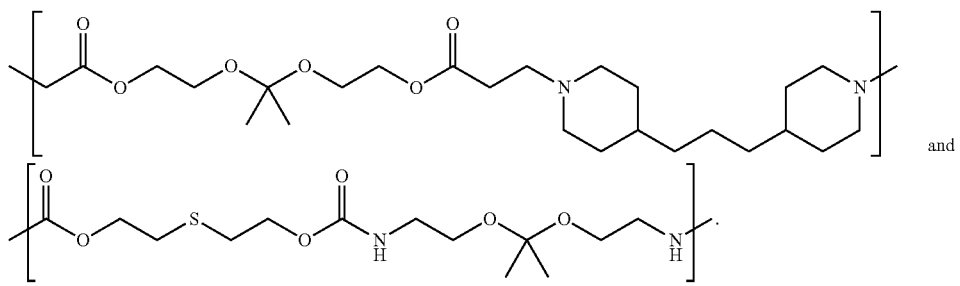

In some embodiments, the polymer comprises

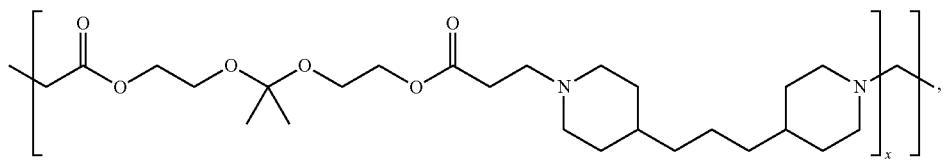

wherein x is a single integer greater than 1. In other embodiments, the polymer comprises

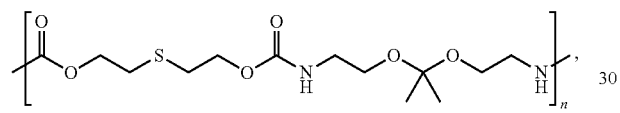

wherein n is a single integer greater than 1.

In some embodiments of the invention described herein, the polymer comprises:

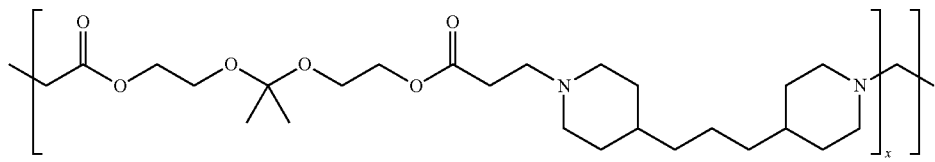

or a derivative thereof, wherein x is as defined herein and understood in the art. In other embodiments, the polymer comprises:

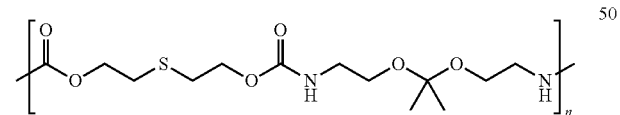

or a derivative thereof, wherein n is as defined herein an understood in the art. In some embodiments of the invention, the polymer comprises

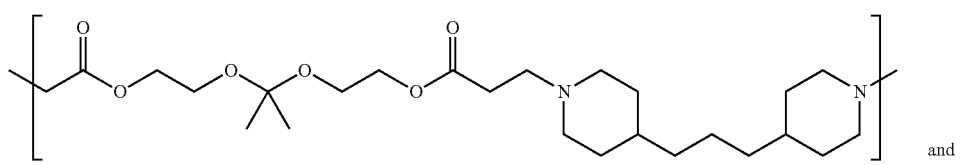

-continued

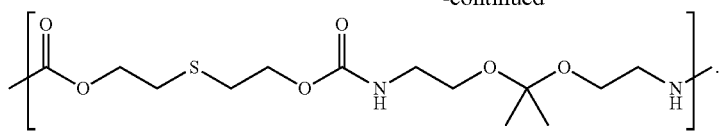

In a further aspect, the present invention features a kit comprising a composition of the invention. Such a kit may comprise instructions.

In another aspect, the present invention features a composition comprising a logic gate nanocarrier as described herein that is used to deliver the payload to a patient in need of treatment. The logic gate nanocarrier of the present invention features the ability to deliver the payload to specific areas, specific tissues, organs, diseases, disease tissues, or disease areas within the patient by being able to respond to environmental signals in these localities to degrade the logic gate nanocarrier and thereby release the payload. In some embodiments, the environmental signal is lower pH; in some embodiments, the environmental signal is the presence of a higher than normal concentration of ROS. In some embodiments, the logic gate nanocarrier responds to both a lower pH and a higher than normal concentration of ROS.

In yet another aspect, the present invention features methods of manufacturing a logic gate nanocarrier. In some embodiments of this aspect, the logic gate nanocarrier comprises a payload; in some embodiments, the payload features at least one type of bioactive agent.

BRIEF DESCRIPTION OF THE DRAWINGS

FIG. 3 diagrammatically illustrates a Logic Gate design for tuning the degradation and release profile of polymeric nanoparticles. A nanoparticle, such as a nanocarrier of the present invention, fragments and releases its payload.

FIG. 27A shows the calculated molecular weight change of the pH-degradable versus time at three pH values. FIG. 27B shows the percent acetone release from the same samples.

FIGS. 28A and 28B depict the relaxivity determination of both polymer contrast agents, where FIG. 28A is a plot of inverse T1 relaxation time versus gadolinium concentration, and FIG. 28B is a sample phantom image of the setup of the relaxation experiment. Polymer solutions used in calculating the relaxivity of the polymers are visible (intensity vs. concentration is not linear).

FIG. 34A shows DNA encapsulation efficiency analyzed by comparing free DNA (lane 1) with un-encapsulated DNA (lane 2); FIG. 34B plots nanoparticles-DNA stability in pH 7.4 tested over 24 hours followed by immediate release in pH 5; and FIG. 34C shows complexation of DNA.

DETAILED DESCRIPTION pH Activation

Iterations in acid-base homeostasis are common in pathology, especially in and/or near cancers (Gillies, et al. (2004) *IEEE Engineering in Medicine and Biology Magazine* 23, 57-64). In some embodiments, nanocarriers of the present invention degrade and release their contents in response to reduced pH. Thus, in some embodiments of the present invention, physiological disease pH states trigger a response from the molecularly-engineered polymer, which in turn, leads to the activation of a secondary catalytic response within nanocarriers and thereby the rapid and bulk degradation of nanocarriers of the present invention. An illustration of using such pH-responsive behavior to deliver a bioactive agent as described herein is shown in FIG. 3.

Figure 4:
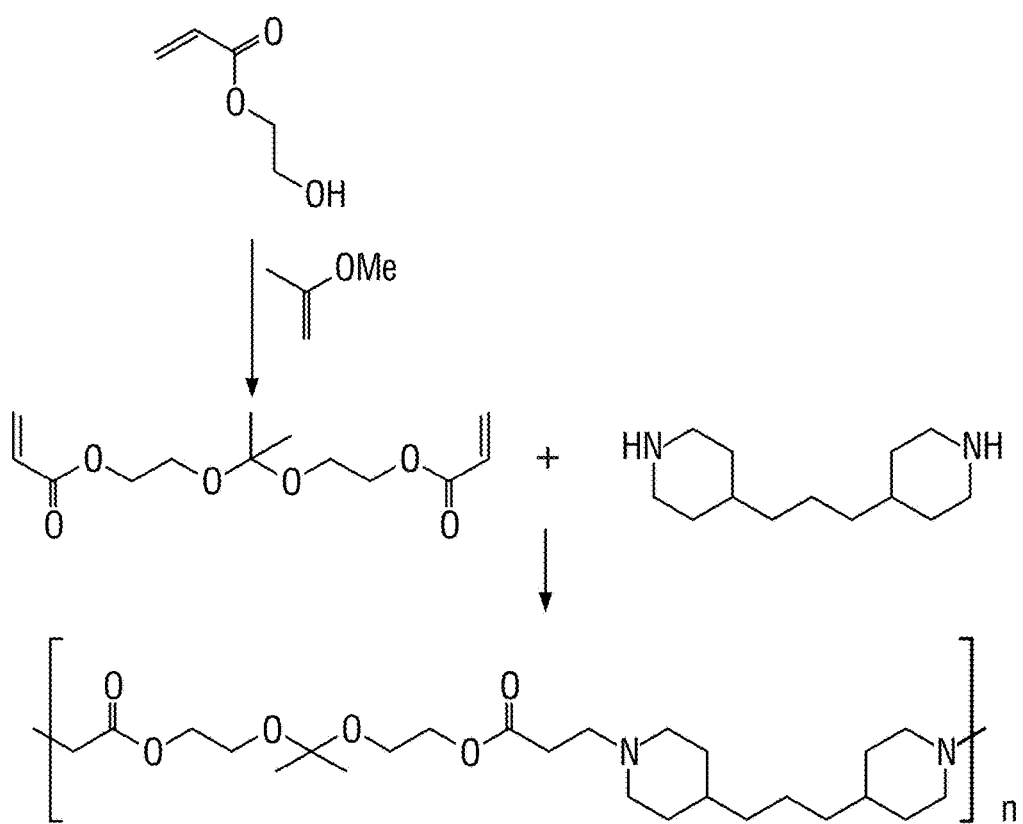
FIG. 4 depicts the chemical structure of a dual-responsive pH-sensitive polymer of the present invention, as well as a synthetic scheme that yields the desired polymeric backbone. Without being bound by any theory, the primary response mechanism utilizes the molecular unit of 4,4'-trimethylenedipiperidine, which in the polymeric form is protonated (more hydrophilic) at mildly acidic pH 6-6.5; and the secondary response molecular unit is a ketal group, and it facilities rapid and bulk hydrolysis catalyzed by protons.

The chemical structure of a pH-responsive molecularly-engineered class of polymer of the present invention is depicted at the bottom of FIG. 4. Hydrophobic polymers, such as poly-β-aminoesters made from 4,4'-trimethylene-dipiperidine can encapsulate payloads of hydrophilic macromolecules and hydrophobic small molecules, forming nanocarriers (Lynn, et al. (2001) *Angewandte Chemie—International Edition* 40, 1707-1710). Incorporating ketal groups in the polymer backbone (Yang, et al. (2008) *Bioconjugate Chem.* 19, 1164-1169), as disclosed in some embodiments herein, incorporates the pH lability into the polymeric backbone of nanocarriers. Using the ketal structure in the backbone also allows for the breakdown of the material forming the nanocarrier backbone into less toxic degradation products than other backbone constituents used in the art. For example, by using ketal groups as labile bonds, as opposed to, for example, esters, the degradation products of polymer degradation are not acids, this thereby reduces or avoids inflammatory effects, such as those documented by (Anderson & Shive (1997) *Advanced Drug Delivery Reviews* 28, 5-24).

ROS Activation

Hydrogen peroxide is a source of oxidative stress and oxidative damage resulting from cellular imbalances of $H_2O_2$ and other reactive oxygen species (ROS). It is associated with cancer (Ohshima, et al. (2003) Arch. Biochem. and Biophy, 417, 3-11 (2003).) and other human diseases, some of them severe (Shah & Channon (2004) *Heart* 90, 486-487.). The chemical structure of a ROS-responsive molecularly-engineered polymer of the present invention is depicted in FIG. 5, as well as its response to mildly oxidative environments.

In some embodiments of the present invention, ROS, such as those found associated with some physiological disease states, trigger a response from the molecularly-engineered polymer, which in turn, leads to the activation of a secondary response within nanocarriers and thereby the rapid and bulk degradation of nanocarriers of the present invention.

Figure 5:
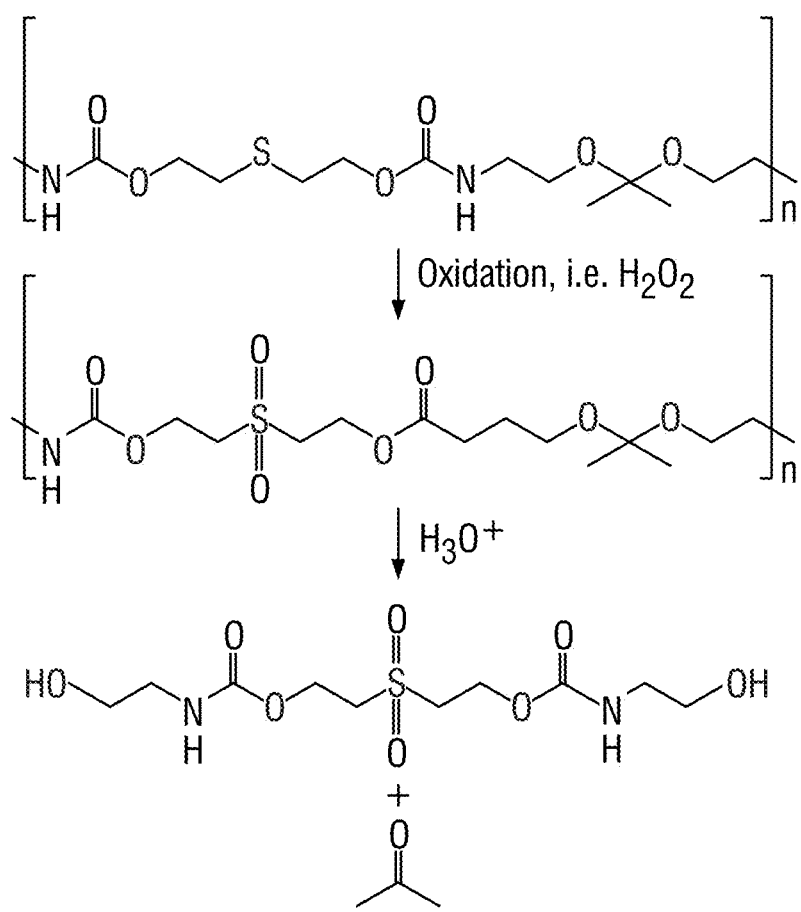
FIG. 5 depicts a hydrophobic polymer that reacts with hydrogen peroxide to yield a hydrophilic polymer, which in mildly acidic environments will fragment.

Hydrophobic polymers, such as those shown in FIGS. 4 and 5 can be used to encapsulate payloads of hydrophilic macromolecules and hydrophobic small molecules, forming nanocarriers. Incorporating a sulfur atom into the polymer backbone, as disclosed in some embodiments herein, allows the polymeric backbone of nanocarriers to respond to mildly oxidative conditions. Using the sulfur-containing structure in the backbone also allows for the breakdown of this material forming the nanocarrier backbone into degradation products with little or no toxicity.

Exemplary Biomarkers

In some embodiments, the active targeted release provided by the present invention exploits atypical extra- and intra-cellular microenvironments as well as other physiological characteristics to distinguish targeted, e.g., diseased, and untargeted tissue. Reactive oxygen species, transition metals, tissue homeostasis of pH, and enzymes are highly regulated in vivo equilibria and/or processes that are frequently altered in pathological states. As noted supra, mildly acidic pH and mildly oxidative environments are common in metabolic disorders such as cancer and can be used to distinguish cancer tissue from healthy tissue at distal locations in the body. Other diseases, or disease states, such as unwanted or excessive inflammation, can also be distinguished on the basis of altered in vivo equilbria and/or processes.

In particular, pH-activation has long been a useful tool for differentiating between healthy and disease-state tissue in the pharmaceutical industry. This has been particularly illustrated by the research focus on pro-drugs activated by a change in pH. Combining the concept of pH-activation selection with the polymeric nanocarrier delivery technology of the present invention produces increased site-specific targeting while creating a delivery vehicle that is broadly applicable.

In the present invention, this strategy is applied to physiological cues of inflammatory diseases (see, e.g., Punnia-Moorthy, A. (1987) *J of Oral Path. & Med.* 16, 36-44; Ródenas et al. (1995) *Free Radical Biol. Med.* 18, 869-875; and Greenwald, R. A. (1991) *Seminars in Arthritis and Rheumatism* 20, 219-240).

Treatment of Disease

The potential impact and benefits of the present invention are broad and large. The 'sense and release' dual response technology detailed in this invention enables the effective delivery to a site of interest one or more bioactive agents encapsulated in a nanocarrier of the invention. The present invention detailed herein overcomes logistical issues that have prevented the commercialization of many pharmaceuticals and/or drug delivery systems; among these logistical issues are serum instability and short shelf life. The present invention provides for methods to deliver pharmaceutical agents and in a more accurate, and more cost effective manner. Furthermore, the present invention may facilitate monitoring the effect and status of the delivered pharmaceutical agent.

Diagnosis of Disease

In some embodiments of the present invention, in addition to a nanocarrier's use in delivering bioactive agents and pharmaceutical agents, they can also be used for the controlled release of imaging agents.

Using novel polymeric nanosystems that are activated upon a specific in vivo event, the present invention therefore also features site-specific molecular imaging. In some embodiments, in a non-limiting example, Magnetic Resonance Imaging (MRI) and/or Near Infrared (NIR) Imaging agents are deactivated through their enclosure in a nanocarrier, then released in proximity to disease tissue, or another site of interest. Thus, nanocarriers of the present invention may be used image and/or detect cancer and/or cardiovascular disease.

Figure 1A:
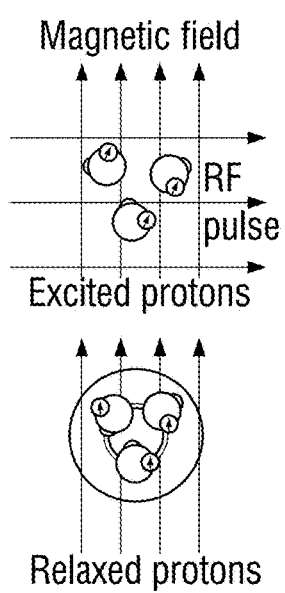
FIG. 1A depicts (i) an external magnetic field is applied and protons are excited with a radio frequency (RF) pulse, and (ii) signal is detected when protons relax.
Figure 1B:
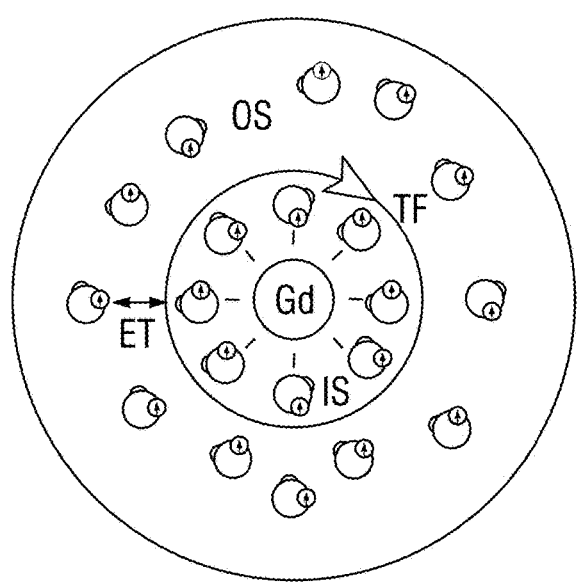
FIG. 1B illustrates the four parameters that influence the enhancement in proton relaxation rates; outer water sphere (OS) and inner water (IS), tumbling frequency (TF) of the MRI agents, and the water exchange rate of the contrast agent (ET).
Figure 2:
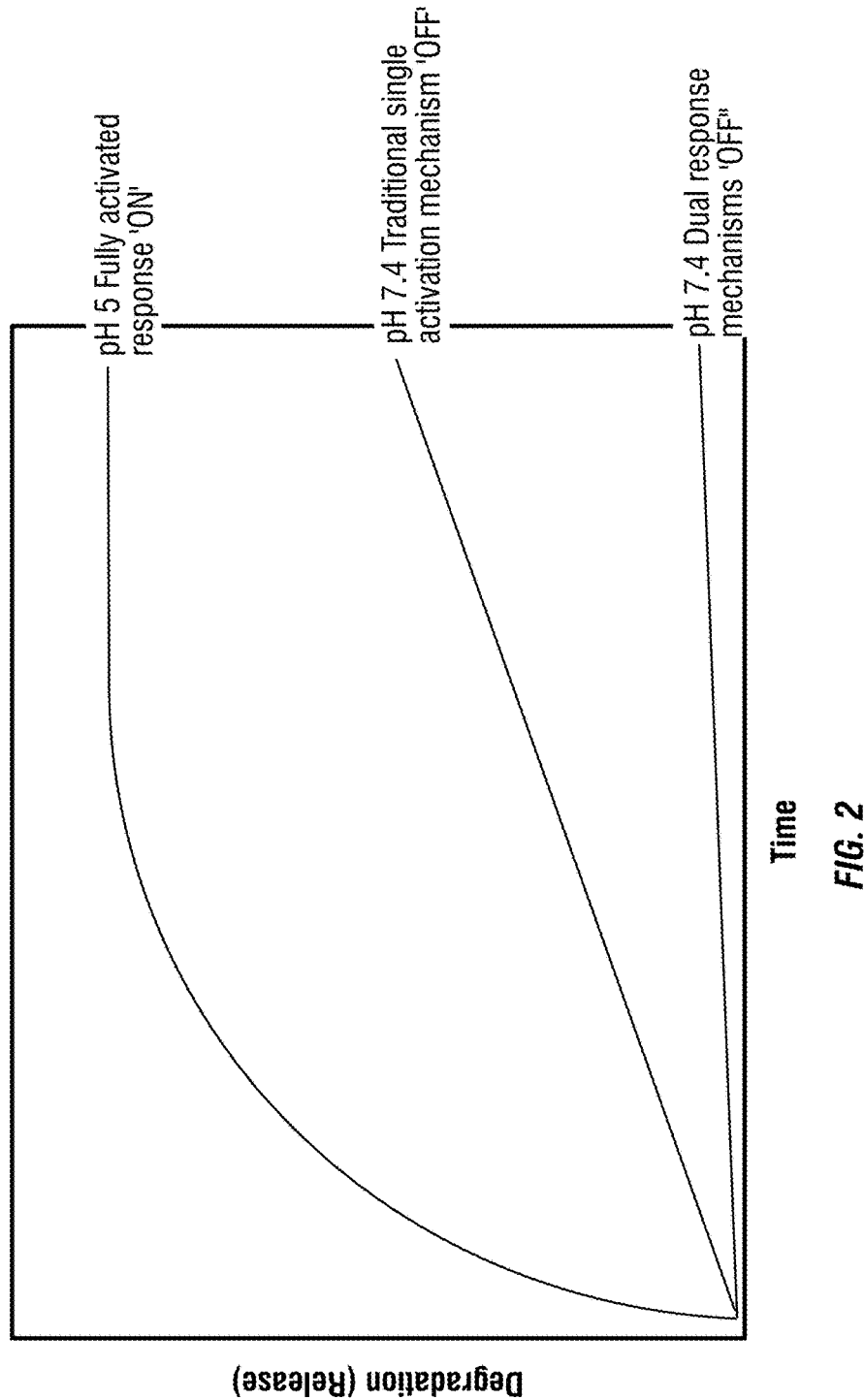
FIG. 2 depicts the synergistic release of a bioactive agent of interest accomplished by the two gate linear response in the present invention. This illustrates advantages of increasing the degradation rate in the 'ON' state and reducing non-specific degradation rate in the 'OFF' state by the incorporation of a two gate linear response (also known as a dual-response activation) versus a single activation mechanism.

In summary, various embodiments of the present invention feature molecularly engineering linear dual-response mechanisms into the backbone of polymeric nanocarriers, and thereby (1) enhancing the stability of nanocarriers as well as any encapsulated bioactive agent both with respect to its half-life in serum and to its shelf life; (2) increase response sensitivity and efficacy of targeted delivery to targeted, e.g., diseased, environments; and (3) reduce overall toxicity by virtue of the degradation of the polymeric nanoparticles into innocuous and easily excretable fragments once the nanocarrier's function is fragmented. Prepared logic gate nanocarriers taught by the present invention will prove valuable in delivering therapeutics and diagnostics to close proximity of cells and diseased tissue. FIG. 2 demonstrates the synergistic release ability of the present invention accomplished by the two gate linear response.

The nanocarriers of the present invention are composed of a dual stimuli and response polymeric backbone are stable in healthy physiological conditions yet they are able to rapidly fragment in subcellular and diseased conditions. Rapid fragmentation is important for release of the bioactive payload, especially the cytoplasmic release.

Although this description of the present invention focuses on the use of nanocarriers to deliver bioactive agents, other types of Payloads are possible.

By forming a cage around the Payload(s) that can be uncoupled remotely, the present invention provides a 'locate and release' technology enabling the effective delivery of a cargo encapsulated in nanoparticles or microparticles to specific areas.

The instant invention overcomes logistical issues that have heretofore increased the difficulties inherent with commercialization of many drug delivery systems, such as serum instability and short storage life. The instant invention provides the pharmaceutical worker in the art with methods to deliver drugs in a more accurate and more cost-effective manner as well as providing means for evaluating their performance.

The instant invention provides advantages in the diagnostics arena where it can be used to enhance the early diagnosis of disease, which, in turn, improves the possibility of successful treatment. If the nanoparticle and/or microparticle of the invention is localized by affinity to an area of interest, e.g., a metastatic tumor's location, the remotely triggered response of the present invention increases the ease of detection.

These applications open to the present invention are facilitated by the ability of the present invention to easily tune the size, chemistry, topology, and the biological response of these materials through chemical design, synthesis and engineering. Encapsulation of viral particles, DNA, proteins, and adjuvants, in the same nanoparticle may help to realize optimal cytotoxic T lymphocytes (CTLs) responses and antibody responses by sequestering the vaccine components until they reach the target cell, delivering them to a particular class of cells, and/or aiding in their presentation via the desired pathway. Moreover, with the development of new adjuvants, gene based vaccines and other multi-modal approaches to vaccination, it becomes increasingly important to use carriers tailored to these novel immunization approaches.

It should be appreciated that certain features of the present invention that are, for clarity reasons only, described in the context of separate embodiments, may also be provided as part of the present invention in combination in a single embodiment. On the other hand, various features of the invention, which are, for clarity purposes only, described in the context of a single embodiment may also be provided separately or in any suitable sub-combination.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention illustratively described herein can suitably be practiced in the absence of any element or elements, limitation or limitations that is not specifically disclosed herein. Thus, for example, the terms "comprising," "including," "containing," etc. shall be read expansively and without limitation. Furthermore, although elements of the present invention has been defined broadly with the compositions and/or methods of the invention comprising a variety of elements, in particular embodiments, individual elements may be claimed as "consisting of" or "consisting essentially of" that individual element.

Additionally, the terms and expressions employed herein have been used as terms of description and not of limitation, and there is no intention in the use of such terms and expressions of excluding any equivalent of the invention shown or portion thereof, but it is recognized that various modifications are possible within the scope of the invention claimed.

Thus, it should be understood that although the present invention has been specifically disclosed by preferred embodiments and optional features, modifications and variations of the inventions embodied herein disclosed can be readily made by those skilled in the art, and that such modifications and variations are considered to be within the scope of the inventions disclosed herein. The inventions have been described broadly and generically herein. Each of the narrower species and subgeneric groupings falling within the generic disclosure also form the part of these inventions. This includes within the generic description of each of the inventions a proviso or negative limitation that will allow removing any subject matter from the genus, regardless or whether or not the material to be removed was specifically recited.

In addition, where features or aspects of an invention are described in terms of the Markush group, those schooled in the art will recognize that the invention is also thereby described in terms of any individual member or subgroup of members of the Markush group. Further, when a reference to an aspect of the invention lists a range of individual members, as for a non-limiting example, 'the letters A through F, inclusive,' it is intended to be equivalent to listing every member of the list individually, that is 'A, B, C, D, E and/or F,' and additionally it should be understood that every individual member may be excluded or included in the claim individually. Additionally, when a reference to an aspect of the invention lists a range of individual numbers, as for a non-limiting example, '0.25% to 0.35%, inclusive,' it is intended to be equivalent to listing every number in the range individually, and additionally it should be understood that any given number within the range may be included in the claim individually.

The steps depicted and/or used in methods herein may be performed in a different order than as depicted and/or stated. The steps are merely exemplary of the order these steps may occur. The steps may occur in any order that is desired such that it still performs the goals of the claimed invention.

Furthermore, although the present invention has been described in conjunction with specific embodiments thereof, it is evident that many modifications, alternatives, and variations will be apparent to those skilled in the art. Accordingly, the present invention should be construed to embrace all such modifications, alternatives, and variations that fall within the spirit and broad scope of the claims.

All publications, patents, and patent applications mentioned in this specification are hereby incorporated in their entirety by reference into the specification to the same extent as if each individual publication, patent, or patent application was specifically and individually indicated to be incorporated herein by reference. In addition, citation or identification of any reference in this application shall not be construed as an admission that such reference is available as prior art to the present invention.

Exemplary Definitions

As used here, the term "molecularly-engineered polymer" is a polymer comprising subunits that have been designed and synthesized with at least two structural features that allow for two linear response mechanisms. When, for example, nanocarriers made from polymers of the present invention are exposed to a mildly acidic pH (or, in some embodiments, mildly oxidative) environment, the structural feature causes the polymeric nanocarriers to become hydrophilic. This allows water to intercalate into the nanocarrier. In another non-limiting example, the structural feature activates a second response mechanism that brings about a rapid and full degradation of the nanocarrier.

Exemplary molecularly-engineered polymer subunits include one selected from the group consisting of

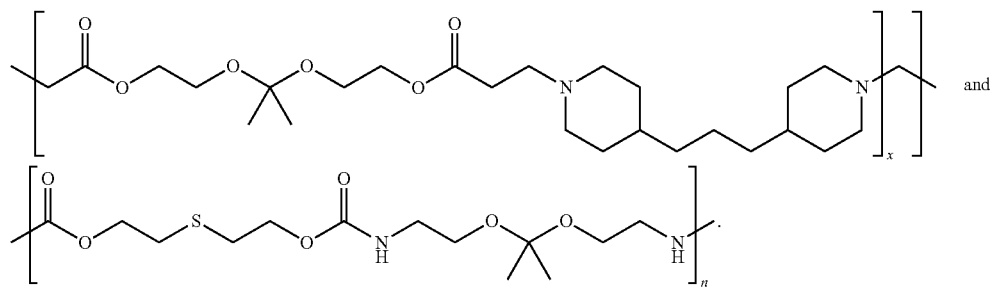

With the teachings herein, skilled artisans will understand that other polymer subunits are possible and within the teachings of the invention.

In some embodiments, x is a single integer greater than 1. In other embodiments, x is a single integer greater than 500 or a single integer greater than 1,000. In some embodiments, x is a single integer between 1 and 100, 1 and 1000, 1 and 10,000 or 1 and 1,000,000. In other embodiments x is a single integer between 500 and a million. In yet other embodiments, x is a single integer between 100 and 100,000.

In various embodiments, n is a large number that varies depending on polymer polydispersity. In some of these embodiments, the value of n is based on a polydispersity level reported herein. In some embodiments, n is a single integer greater than 1. In other embodiments, n is a single integer greater than 500 or a single integer greater than 1,000. In some embodiments, n is a single integer between 1 and 100, 1 and 1000, 1 and 10,000 or 1 and 1,000,000. In other embodiments n is a single integer between 500 and a million. In yet other embodiments, n is a single integer between 100 and 100,000.

As used herein, the term "linear dual-response activation mechanism" refers to a combination of two different activation mechanisms associated with a logic gate nanocarrier that brings about the degradation of the nanocarrier. By utilizing a primary and secondary mechanism of activation, the present invention achieves a more rapid and wide-spread response to the stimulus. This provides for an increased sensitivity and efficacy in sensing diseased environments, or other targeted site, and then releasing and/or activating bioactive agents at the targeted site. More than two activation mechanisms are also possible within the present invention. The activation mechanism may be triggered by the interior of an endosome.

As used herein, the term "Logic Gate Nanocarrier" refers to a nanocarrier where two chemical transformations are required to bring about degradation of all or substantially all of the nanocarriers, and where the two chemical transformations are required to take place in a defined order. As used herein "preferentially release" refers to when a nanocarrier releases its Payload in response to encountering triggering conditions, e.g., low pH within a patient or both ROS and low pH within a patient. In many embodiments, a logic gate nanocarrier comprises a molecularly-engineered polymer as described in the present invention.

The rapid, controlled fragmentation obtained by the logic gate nanocarrier of the invention may be referred to herein as "burst fragmentation" and the rapid, controlled release obtained by the logic gate nanocarrier of the invention may be referred to herein as "burst delivery".

As used herein, the term "nanocarrier" refers to an assembly of polymers according to the teachings of the present invention. A nanocarrier of the present invention may include an associated Payload. The term "nanoparticles" is generally synonymous with the term "nanocarrier," but may used to indicate there is no payload associated with the nanocarrier. Even so, when used herein, the term "nanoparticles" may refer to nanocarriers with a payload.

The term "nanoparticle" as used herein, generally refers to discrete structures that are at least under 200 nm in diameter, in other words, significantly less than the diameter of a capillary. (See, e.g., Singh, R., J. W. Lillard Jr., Exper Mol Path 86 (2009) 215-223.) The term "nanoparticle" may also refer to particles that are between 1 nm and 100 nm in diameter. Some of the novel properties associated with nanoparticles, which differentiate them from bulk materials, is generally associated with their size being less than 100 nm.

Microparticles and/or nanoparticles can be formed by a wide variety of means and with widely varying compositions. Examples include hydrogels such as acrylamide micelle polymerization. The may also be created from such diverse substances as poly(D,L) lactides; poly (lactic acid) ("PLA"); poly (D,L glycolide) ("PLG"); poly(lactide-co-glycolide) ("PLGA"); and poly-cyanoacrylate ("PCA") (Singh, R., J. W. Lillard Jr., (2009) Exper Mol Path 86, 215-223). Microparticles and/or nanoparticles can also be created from various forms of micelles/liposomes; such micelles/liposomes can be assembled via emulsions or through a process of depositions. Acrylamide hydrogels, such as ones made from N-isopropylacrylamide (NIPAAm) and acrylamide (AAm) have been made incorporating gold-gold sulfide nanoshells designed to strongly absorb near-infrared light, e.g., wavelengths between 800 and 1200 nm. When these nanoparticles are irradiated, the temperature is increased, causing in turn the release of associated molecular cargo (Sershen, et al. (2000) *J Biomed Mater Res.* 51(3): 293-98. Examples of microparticles and/or nanoparticles also include dendrimers (see, e.g., Cheng, et al. (2008) *Front. Biosci.* 13 1447-1471). Types of microparticles and/or nanoparticles have also been described in PCT US2007/006844.

Microparticles and/or nanoparticles can also be formed according to the teachings of the present invention.

As used herein, the term "bioactive agent" refers to any molecule or molecules that are administered by a practitioner to produce an effect within a patient. A bioactive agent may include a pharmaceutical agent, such as a drug, and/or an imaging agent. The term "bioactive agent" is not meant to be restricted to a single type of agent, and a bioactive agent associated with a nanocarrier as used herein may also can include populations and/or combinations of bioactive agents with one, two, or a plurality of components. Each of the components may be capable of acting, or functioning as a bioactive agent, by itself.

The bioactive agents, pharmaceutical agents and/or other substances carried and/or then released by the nanocarriers are broadly referred to herein as "Payload(s)". One type of bioactive agent is a drug. The term "drug" as used herein is defined as a medicament, medicine, or composition which is used for the therapeutic treatment of a medical condition or disease. The drug may be used in combination with another drug or type of therapy and in a preferred embodiment is effective for the treatment of an abnormal condition such as a disease.

As used herein, the term "Payload(s)" refers to any compound of interest that can be incorporated into the molecular network of the present invention. Non-limiting examples of Payloads comprise chemicals such as drugs, APAs, pharmaceutical agents, and/or radioactive elements; a Payload can also comprise proteins such as antibodies, antibody fragments, antigens, cytokines; a Payload can also comprise nucleic acids, including DNAs, RNAs, siRNAs, antisense oligonucleotides; a Payload can also comprise detectable labels, such as fluorescent compounds (e.g., rhodamine dyes or fluorescent proteins); and/or a Payload can also comprise a cocktail that comprises more than one compound (e.g., a pharmaceutical agent and an antibody). In the embodiment where a Payload consists of multiple entities, each may be present separately within the nanoparticle and/or microparticle or some of the entities may be conjugated together in various combinations. Furthermore the multiple entities may be present in separate particles and the particle may be combined for use. The Payload(s) delivered by the embodiments of the present invention may routinely contain pharmaceutically acceptable concentrations of salts, buffering agents, preservatives, compatible carriers, and optionally other therapeutic agents. In preferred embodiments of the present invention the Payload(s) is not covalently attached to the molecular network of the invention.

As used herein, the terms "enclosed" and "encapsulated" refer to associating an agent with a nanocarrier. The term doesn't require that the agent is completely enclosed within the nanocarrier, only that it is substantially associated with the nanocarrier and this association is stable and protects the agent.

As used herein, the term "release" means that all or substantially all the Payload associated with the nanocarrier becomes dissociated from the nanocarriers and its constituent polymers, frequently, but not always, accompanying the degradation of the nanocarrier. As used herein in this instance, the "substantial release" may refer to the release of approximately 50% or more; the release of approximately 60% or more; the release of approximately 70% or more; the release of approximately 80% or more; the release of approximately 90% or more; the release of approximately 95% or more; or the release of approximately 99% or more of the Payload associated with the nanocarrier.

The term "treating" refers to administering a composition to an organism afflicted with an abnormal condition, such as a cell proliferative disorder, where the administration of the composition has a therapeutic effect and at least partially alleviates or abrogates the abnormal condition. Note that the treatment needs not provide a complete cure and the treatment will be considered effective if at least one symptom is improved or eradicated. The treatment may reduce mortality. Furthermore, the treatment need not provide a permanent improvement of the medical condition or other abnormal condition, such as a cell proliferative disorder, although this is preferable. The treatment may work by killing cancerous cells, facilitating killing of the cancerous cells, inhibiting the growth of cancerous cells, and/or inhibiting the process of metastasis of cancer. The treatment may also work by reducing the tumor volume, inhibiting an increase in tumor volume, inhibiting the progression of the tumor, stimulating tumor cell lysis, stimulating tumor cell lysis necrosis, or stimulating tumor cell lysis apoptosis.

The terms "administration" or "administering" refer to a method of incorporating a compound into the cells or tissues of an animal, preferably a mammal, in order to treat or prevent an abnormal condition. When the composition of the invention is provided in combination with one or active agents, the terms "administration" or "administering" include sequential or concurrent introduction of the composition with the other agent(s). For cells harbored within the organism, many techniques exist in the art to administer compounds, including (but not limited to) oral, injection, parenteral, dermal, and aerosol applications.

The term "abnormal condition" refers to a function in the cells or tissues of an organism that deviates from their normal functions in that organism and includes, but is not limited to, conditions commonly referred to as diseases. An abnormal condition can relate to cell proliferation, cell differentiation, cell survival, cellular function, or the activities of enzymes within a cell. Abnormal conditions relating to cell proliferative disorders include cancers, fibrotic and mesangial disorders, abnormal angiogenesis and vasculogenesis, wound healing, psoriasis, diabetes mellitus, and inflammation. Abnormal conditions relating to differentiation include, but are not limited to, neurodegenerative disorders, slow wound healing rates, and slow tissue grafting healing rates. Abnormal conditions relating to cell survival refer to conditions in which programmed cell death (apoptosis) pathways are activated or abrogated. As used herein, the term "disease" broadly relates to all abnormal conditions. Preferably the disease is selected from the group consisting of cancers, immune-related diseases and disorders, cardiovascular disease, brain or neuronal-associated diseases, and metabolic disorders. More specifically these diseases include cancer of tissues or hematopoietic origin; central or peripheral nervous system diseases and conditions including migraine, pain, sexual dysfunction, mood disorders, attention disorders, cognition disorders, hypotension, and hypertension; psychotic and neurological disorders, including anxiety, schizophrenia, manic depression, delirium, dementia, severe mental retardation and dyskinesias, such as Huntington's disease or Tourette's Syndrome; neurodegenerative diseases including Alzheimer's, Parkinson's, Multiple sclerosis, and Amyotrophic lateral sclerosis; viral infections caused by HIV-1, HIV-2 or other viral- or prion-agents or fungal- or bacterial-organisms; metabolic disorders including Diabetes and obesity and their related syndromes, among others; cardiovascular disorders including reperfusion restenosis, coronary thrombosis, clotting disorders, unregulated cell growth disorders, atherosclerosis; ocular disease including glaucoma, retinopathy, and macular degeneration; inflammatory disorders including rheumatoid arthritis, chronic inflammatory bowel disease, chronic inflammatory pelvic disease, multiple sclerosis, asthma, osteoarthritis, psoriasis, atherosclerosis, rhinitis, autoimmunity, and organ transplant rejection.

The term "patient" as used herein refers to a human subject who has presented at a clinical setting with a particular symptom or symptoms suggesting the need for treatment. A patient's diagnosis can alter during the course of the disease, condition, or abnormal condition, such as development of further symptoms, or remission of the disease, condition, or abnormal condition, either spontaneously or during the course of a therapeutic regimen or treatment. The term "patient" may also broadly refer to non-human organisms, such as a mouse, rat, rabbit, guinea pig, goat, cow, horse, pig or other domestic animals.

The present invention, in its various embodiments, provides methods, compounds and formulations for synthesizing and utilizing nanocarriers. Such nanocarriers may comprise bioactive agents, pharmaceutical agents and/or other substances where nanocarriers of the present invention release and/or allow the activation of their payloads in response to signals such as pH and/or reactive oxygen species. In many of these embodiments, the signals required to release and/or activate the payloads of nanocarriers arise from physiological conditions within a patient. The bioactive agents, pharmaceutical agents and/or other substances carried and/or then released by the nanocarriers are broadly referred to herein as "Payload(s)". In some embodiments of the present invention, methods, compounds, and formulations of the present invention are used inside living organisms and their tissues non-invasively, providing a previously unattainable control of the release and/or activation. Because of the location control of the activation and/or release, it is frequently proximate to the disease to be imaged or treated; and thus this proximity increases the efficacy of the Payload. Such control may, for example, greatly increase a practitioner's ability to conduct an assay at a specific location within an organism and/or within a tissue type.

Thus it can be seen that the potential for the embodiments of the invention is large and broad, allowing for localized delivery of bioactive agents within a patient without invasive procedures. Furthermore since the release and/or activation is related to the physiological state in the vicinity of the diseased tissue or other target, previously undetected target sites may be located specifically and precisely, as well as those sites that are already known to a practitioner. This will assist the practitioner in treatment and/or diagnosis.

The present invention accomplishes this by Logic Gate nanocarriers that use dual response mechanisms to impart stability to the 'OFF' state while maintaining a rapid degradation or a sharp 'ON' state. A polymer of the present invention is molecularly engineered with two linear response mechanisms. When, e.g., in a non-limiting example, nanocarriers made from polymers of the present invention are exposed to a mildly acidic pH (or, in some embodiments, mildly oxidative) environment, the polymeric nanocarriers become hydrophilic. This allows water to intercalate into the particle and the water further activates a second response mechanism that brings about a rapid and full degradation of the nanocarrier. In some embodiments, the water activates an encapsulated bioactive agent, e.g., a contrast agent.

The two gate linear response design allows for an increased overall stability of the nanocarrier with respect to both its storage and shelf life, and also in vivo when present in healthy tissue. The advantages of this approach are depicted in FIG. 2, where the combination of two linear responses produces a combined accelerated response. (See, also, e.g., FIG. 3.)

Thus, the present invention addresses two challenges of drug efficacy: substantially increasing the stability of a drug (or other bioactive agent) and substantially increasing a drug's (or another bioactive agent's) effectiveness by releasing of the drug (or other bioactive agent) in a location selected by the practitioner and/or a disease location.

Some embodiments of the present invention also relate to the synthesis of nanocarriers and/or components thereof. Thus, the present invention also provides the synthesis and use of novel molecularly-engineered classes of polymers. When incorporated into the backbone of nanocarriers, the result is polymeric nanocarriers that are stable under physiological conditions. These molecularly-engineered polymers of the present invention used in nanocarriers may respond to different stimuli found in physiological conditions so as to degrade and thereby release the contents of the nanocarriers.

One class of novel polymeric nanocarriers of the present invention responds to lower pH values. For example, such lower pH values may be found surrounding disease sites or diseased tissues, or within endosomes. Nanocarriers produced according to the methods and with the compounds of the present invention may react to a lower pH with linear dual-response activation mechanisms. This feature provides for an increased sensitivity and efficacy in sensing low pH environments, then releasing and/or activating bioactive agents contained by the nanocarriers at the targeted location.

Another class of novel polymeric nanocarriers of the present invention responds to reactive oxygen species (ROS) such as may be found surrounding disease and/or diseased tissue. Nanocarriers produced according the methods and compounds of the present invention react to ROS with linear dual-response activation mechanisms. This feature again provides for an increased sensitivity and efficacy in sensing diseased environments and then releasing and/or activating bioactive agents contained by the nanocarriers at the targeted site.

By utilizing a primary and secondary mechanism of activation, the present invention creates more stable polymeric nanocarriers under normal physiological conditions, thereby substantially protecting bioactive agents from unwanted degradation. In some embodiments of the present invention, this increases the shelf life of the bioactive agents. In some embodiments of the present invention, this allows a highly sensitive release of bioactive agents at, for example, disease sites within a patient's body or at other locations of interest within a patient's body.

Without being bound by any theory, the nanocarriers of the present invention are designed to protect their contents of bioactive agents under normal physiological conditions, and preferentially release the contents under triggering conditions, such as reduced pH and/or the presence of ROS. Thus, in some embodiments of the present invention, a nanocarrier of the present invention does not release bioactive agents non-specifically within the body of a patient to any substantial degree.

Nanocarriers constructed according the principals of the present invention responsive to a reduced pH and/or ROS may respond to such stimuli in an effectively amplified manner.

EXAMPLES

The following examples demonstrate the utility of the present invention. The examples are furnished for illustration, and should not be considered to limit the scope of the present invention.

Example 1 pH-Responsive Polymers

In some embodiments of the present invention, formulating nanocarriers from polymers with a hydrophilic pH switch can both ensure the stability of the nanocarriers, together with an associated payload, in normal physiological pH conditions and still achieve the desired rapid catalytic degradation, and release of their associated bioactive agents, in relatively acidic conditions. In some embodiments, the present invention features a system that has two or more pH response mechanisms responding to triggering events to more finely tune response to pH stimuli.

To accomplish this, logic gate nanocarriers, where two chemical transformations take place one after the other, were successfully formulated from a newly synthesized random co-polymer. This polymer, poly([2,2'-(propane-2,2-diylbis (oxy))bis(ethane-2,1-diyl)diacrylate]-co-[hexane-1,6-diyl diacrylate]-4,4' trimethylene dipiperidine), (poly-β-aminoester ketal-2) contains two pH responsive moieties within its backbone.

Figure 6:
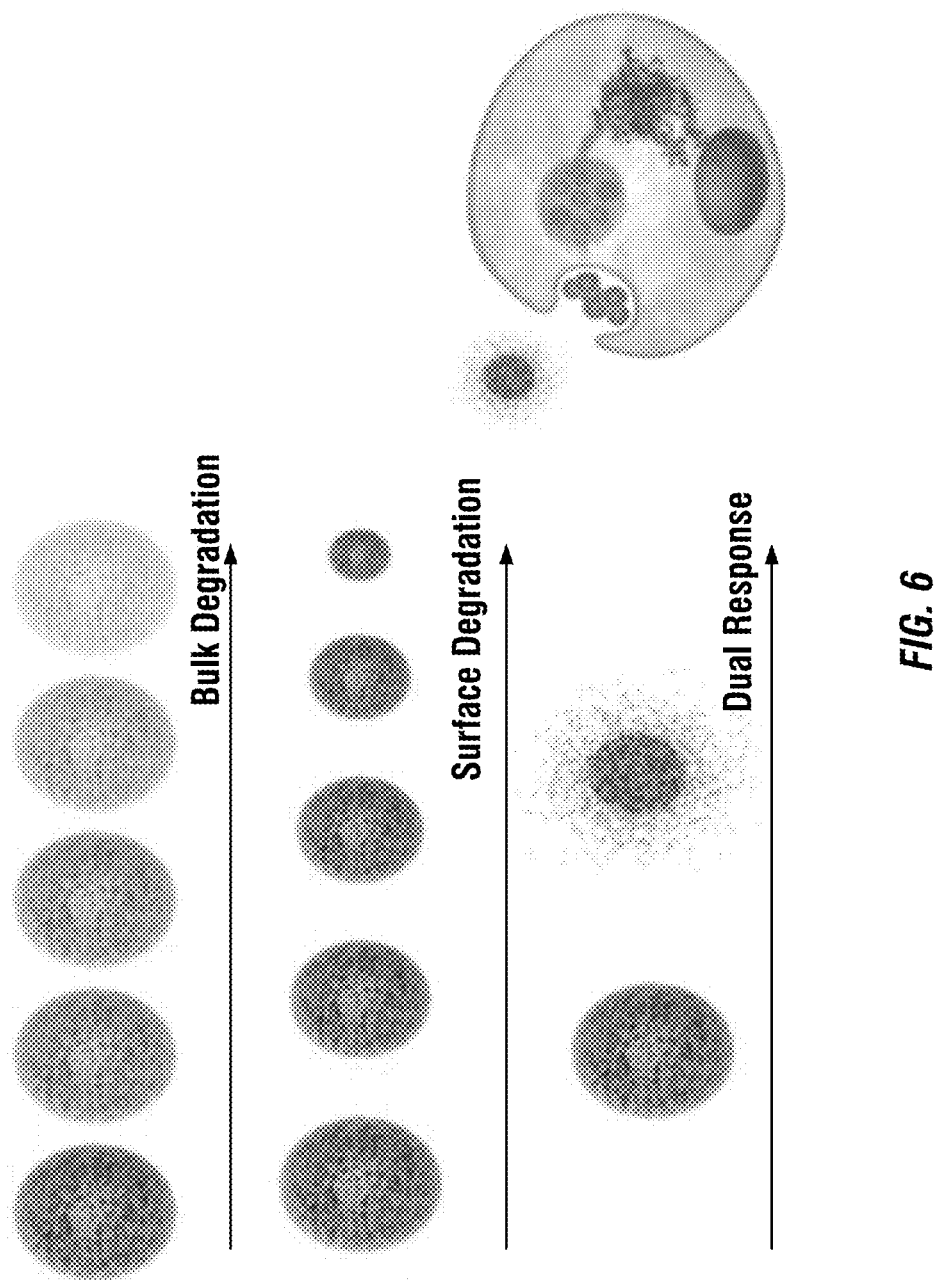
FIG. 6 diagrammatically depicts examples of different release profiles from nanoparticles result in different cellular response.

In response to a single triggering event of a decrease in pH, the amine backbone undergoes a sharp hydrophobic-hydrophilic switch. This leads to an increase in uptake of water (bulk dissolution) and hence an increase in ketal hydrolysis (surface degradation). The second degradation step proceeds by both surface and bulk erosion simultaneously. The degradation and release profile of this newly developed system has promise in exhibiting increased cytosolic release (FIG. 6). (ref 3-33)

When used in nanocarriers, these polymers function akin to an AND logic gate. The β-aminoester backbone moiety provides a pH triggered solubility switch—only when this switch is 'ON' does the ketal moiety also turn 'ON' to undergo rapid acid catalyzed hydrolysis.

Nanocarriers were prepared using an oil in water (o/w) emulsion method. Their degradation in the pH range of 7.4 to 5 was monitored by Dynamic Light Scattering; they showed excellent stability at pH 7.4 and rapid degradation at pH 5.

Nanocarriers formulated using the poly-β-aminoester ketal-2 become hydrophilic at mildly acidic pH 6.5-5.0 and in turn lead to accelerated hydrolysis of the ketal moieties. The pronounced effect of a hydrophilic-hydrophobic balance is evidenced by the fact that the degradation times are significantly faster than that obtained for other hydrophobic polyketals. Furthermore, the dual pH response design of the present invention showed better stability at physiological pH (7.4) than other hydrophilic polyketals, while maintaining the desired rapid degradation at acidic pH.

Synthesis

FIG. 4 depicts the method of synthesizing polymers with a dual pH response system from poly-β-aminoester ketal-1. Nanocarriers formulated from poly-β-aminoester ketal-1 were found to dissolve rapidly at pH 7.4 owing to the increased charge density of the polymer backbone. While the $pK_a$ of the polymer is expected to be similar to the ones calculated in the literature, the solubility switch of the polymer depends on a hydrophilic-hydrophobic balance between the hydrophilic protonated amines and hydrophobic alkyl backbone. Without being bound by any theory, the presence of the ketal group on every monomer unit may make the backbone more hydrophilic and result in more rapidly soluble nanocarriers at pH 7.4. In some other embodiments of the present invention, polymers made from β-aminoester ketal-2 were synthesized incorporating a more hydrophobic spacer. This feature increased the hydrophobicity of the backbone and thereby improved the stability of the nanocarriers at pH 7.4.

Figure 7:
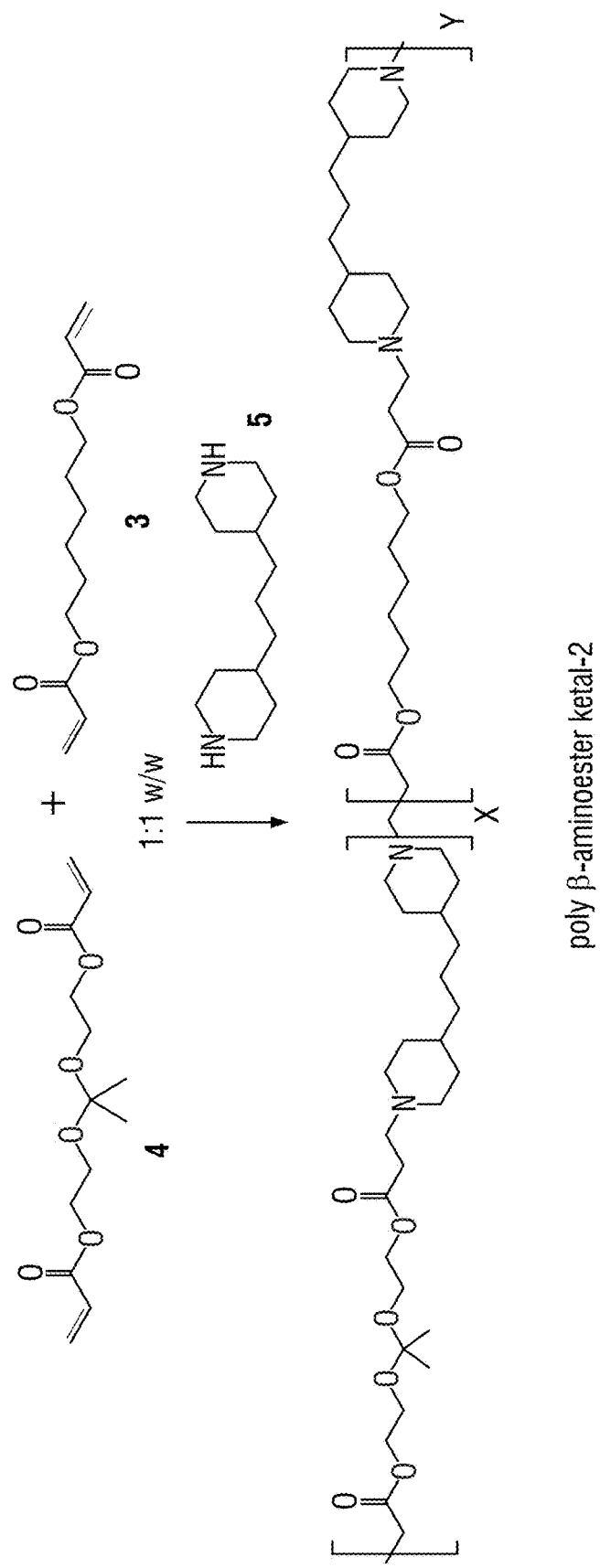
FIG. 7 depicts the scheme for the synthesis of random co-poly-β-aminoester ketal-2.

Poly-β-aminoester ketal-2 was synthesized as shown in FIG. 7 via Michael-type addition of bis(secondary amine) monomers to diacrylate ester and diacrylate ester ketal monomers in a 2:1:1 mixture. The resulting poly-β-aminoester ketal-2 was then formulated using emulsion techniques into logic gate nanocarriers. Transmission electron microscope (TEM) images of the nanocarriers formulated show diameters of 100-150 nm while their average hydrodynamic radius was ~300 nm by Dynamic Light Scattering, DLS.

Influence of pH on Nanocarrier Size

Figures 8A, 8B:
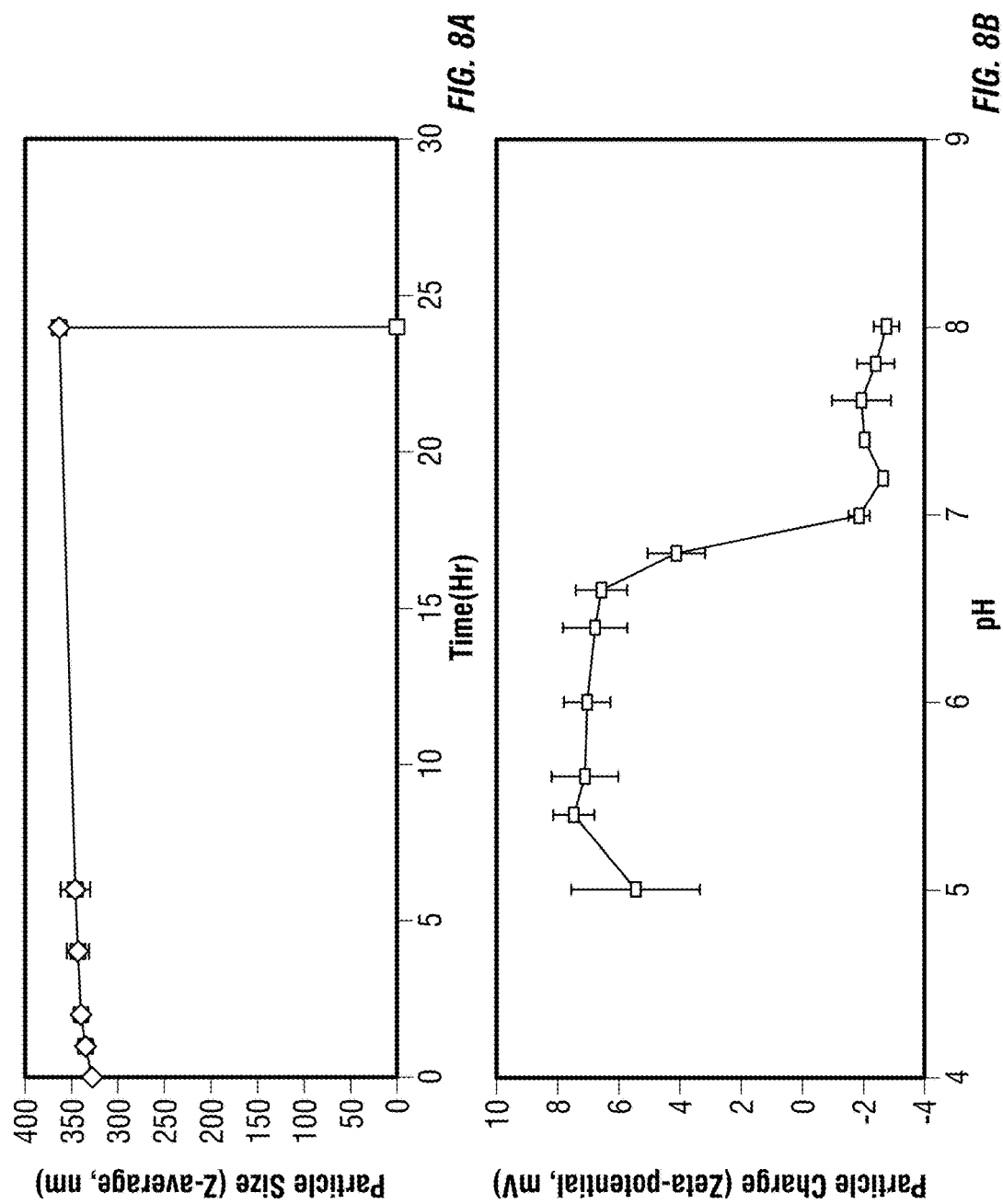
FIG. 8A is a plot of particle size (Z-average) with time and FIG. 8B is a plot of the influence of pH on particle charge (Zeta-potential) for poly-β-aminoester ketal-2 nanoparticles.

The nanocarriers were monitored for 24 hours by DLS, using a Zetasizer-ZS (Malvern, UK). DLS measures hydrodynamic diameter and charge of particles. FIG. 8A shows the nanocarriers remain stable at pH 7.4 over a period of 24 hours without a significant change in size for the first 4 hrs. at pH 7.4 (p>0.05). Subsequently, there is a slight but significant increase between 6 and 24 hours (p=0.044 and 0.002, respectively). This increase in diameter reflects the hydration process of the polymeric nanocarriers due to partial protonation of the amino groups ($pK_a \approx 6.7$) at this pH (FIG. 8B). Changing the pH to 5 (the pH of many cellular sub-compartments) caused a sudden or burst degradation of the nanocarriers. The drop seen in particle size is very dramatic compared to the nanocarriers systems previously published in the literature.

Influence of pH on Nanocarriers Charge

The Zeta potential of the nanocarriers at different pH (FIG. 8) was also measured to detect the protonation of these polymeric nanocarriers with decrease in pH. Zeta potential measurements using DLS gives the charge on these dual response nanocarriers as a function of pH and helps elucidate the degradation mechanism. Poly-β-aminoester ketal-2 nanocarriers were prepared as described and washed using water. A 100 μl suspension of nanocarriers was dispersed in different phosphate buffers with different pH. The charge on the particle increases with decrease in the pH confirming that the amines on the polymer backbone are progressively protonated and the degree of protonation increases dramatically around pH 7-6 which corresponds to the $pK_a$ of the backbone.

Polymer Degradation Studies by GPC and NMR

Figure 9:
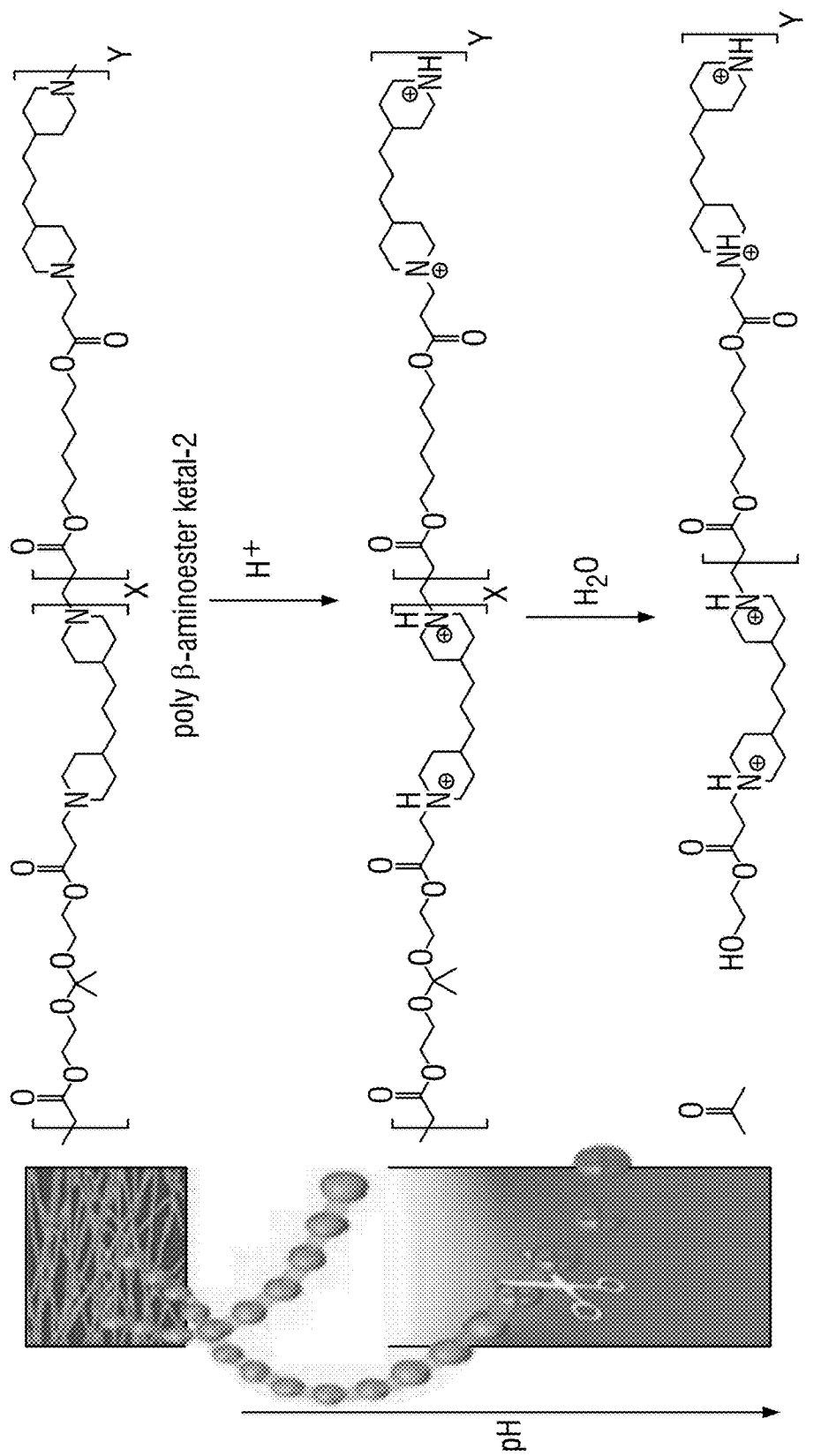
FIG. 9 depicts the scheme of the mechanism of degradation of the polymer backbone of poly-β-aminoester ketal-2.

Polymer degradation studies were performed in order to observe the degradation products and molecular weights of the fragments. NMR studies were carried out by dissolving the polymer in pH 5 phosphate buffer and recording spectra at various time intervals. Acetone peaks appeared immediately and grew until about 2 hours. NMR spectra continued to be recorded for a two week period with no further observation of degradation of the backbone. 100 mg of the polymer was also separately incubated at 37° C. in pH 5 phosphate buffer. Samples were withdrawn at various time points, lyophilized and analyzed via GPC, and it was found that the polymer fragments into smaller fragments at this pH. Based on these findings, this new hydrophobic polymeric nanocarriers is stable at pH 7.4, however upon decreasing the pH the tertiary amines along the polymer backbone become protonated and the polymer becomes more hydrophilic. This results in an increased uptake of water followed by acid catalyzed hydrolysis of the ketal groups along the polymeric backbone (FIG. 9). The ease of degradation of these polymeric nanocarriers is a significant advantage over other systems especially in gene delivery applications as it could minimize the cytotoxicity of the carrier in contrast to other more toxic polyamine systems.

Influence of pH on Nile Red Release from Poly-β-Aminoester Ketal-2 Nanocarriers

Nile red, a non-polar probe that is fluorescent in hydrophobic environments, was encapsulated in dual-response nanocarriers of the present invention in order to investigate the ability of these dual response nanocarriers to release a small hydrophobic molecule, as a model for the release of other bioactive agents.

Figure 10:
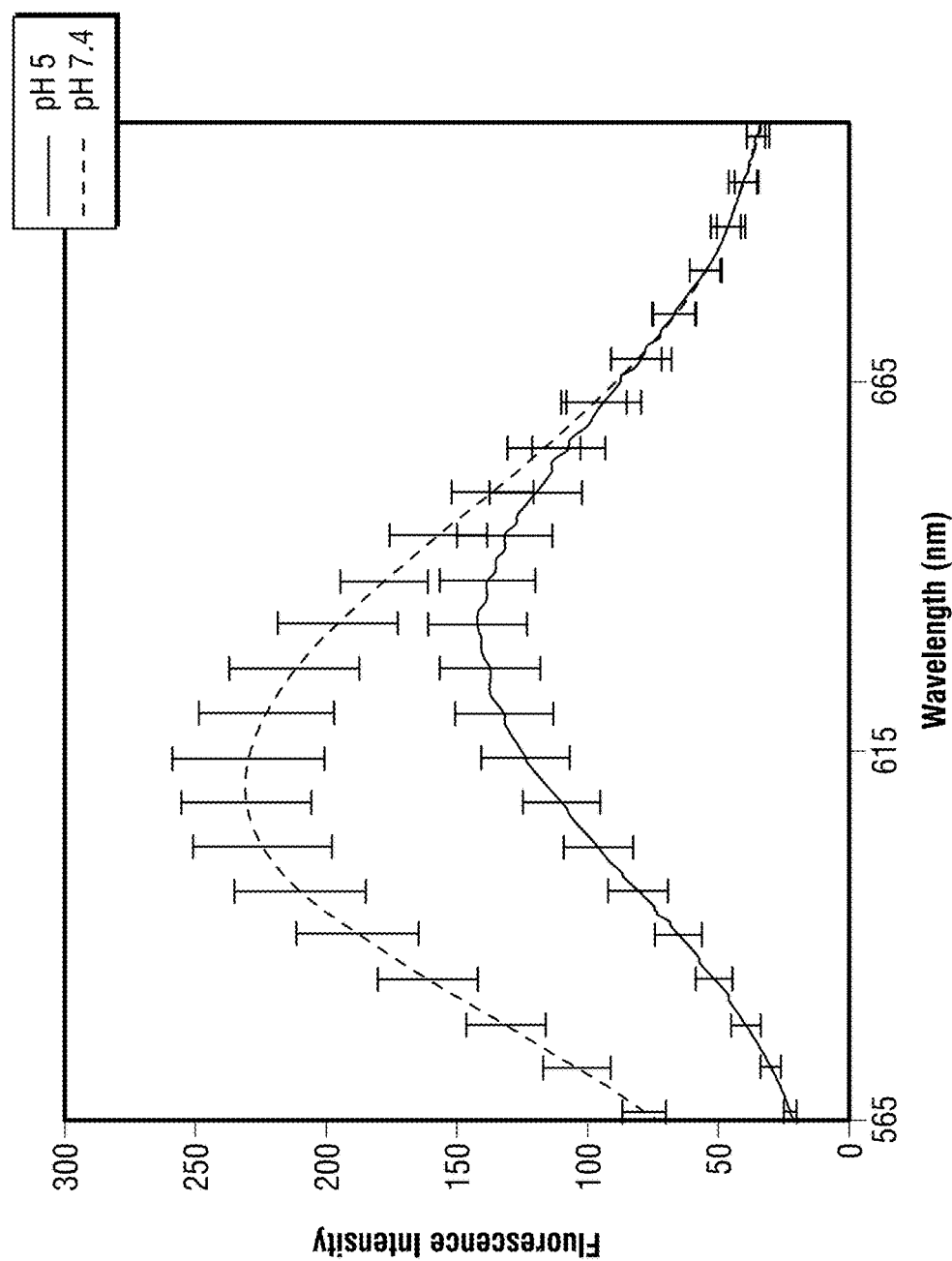
FIG. 10 depicts the significant red and hypochromic shifts ($p<0.001$ and $p=0.010$, respectively) that were observed in the fluorescence absorption spectra of Nile Red poly-β-aminoester ketal-1 nanoparticles suspensions upon changing the pH from 7.4 to 5. These shifts indicate the presence of Nile Red in a hydrophobic environment such as within the nanoparticles which suddenly changes upon decreasing the pH to a more hydrophilic environment.

Nanocarriers containing Nile Red were prepared and the fluorescence of Nile Red poly-β-aminoester ketal-2 nanocarriers was measured at pH 7.4 and 5 (FIG. 10). Upon changing the pH from 7.4 to 5, the fluorescence decreased in intensity coupled with a red shift in the fluorescence peak. These results are indicative of Nile Red release immediately upon decreasing the pH to 5.

Figure 11:
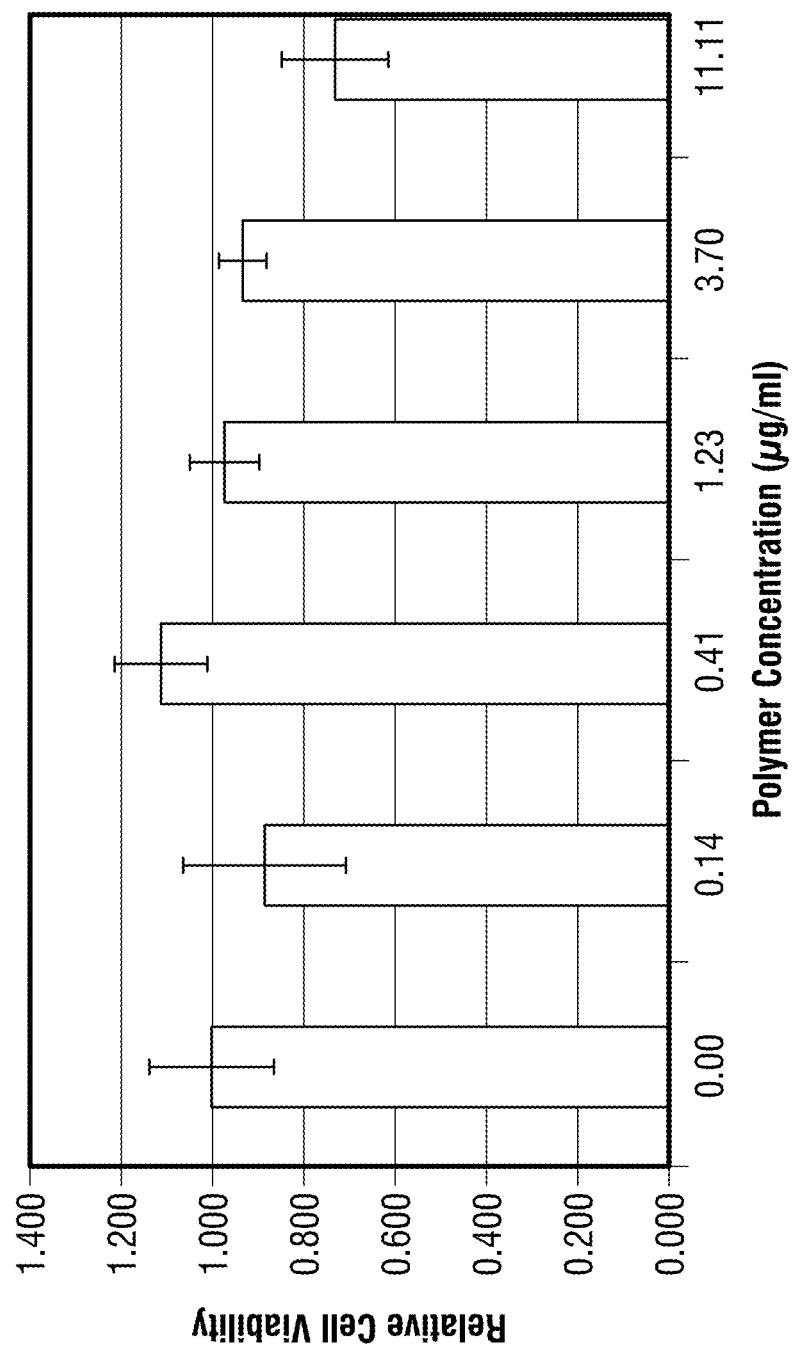
FIG. 11 depicts the cytotoxicity of poly-β-aminoester ketal-2 nanoparticles at different concentrations in RAW 264.7 macrophage cells.

Cytoxicity and Cellular Internalization Studies of the Poly-β-Aminoester Ketal-2 Nanocarriers:

The cytotoxicity of poly-β-aminoester ketal-2 nanocarriers in cells was evaluated by a MTT assay. RAW 264.7 cells were incubated with various amounts of nanocarriers for 20 hr. FIG. 11 illustrates the comparison of cytotoxicity between cells treated with increasing concentrations of poly-β-aminoester ketal-2 with respect to polymer and control cells. There was no significant cytotoxicity observed until high concentrations of polymer were reached (beyond 11.1 ug/ml).

Figure 12B:
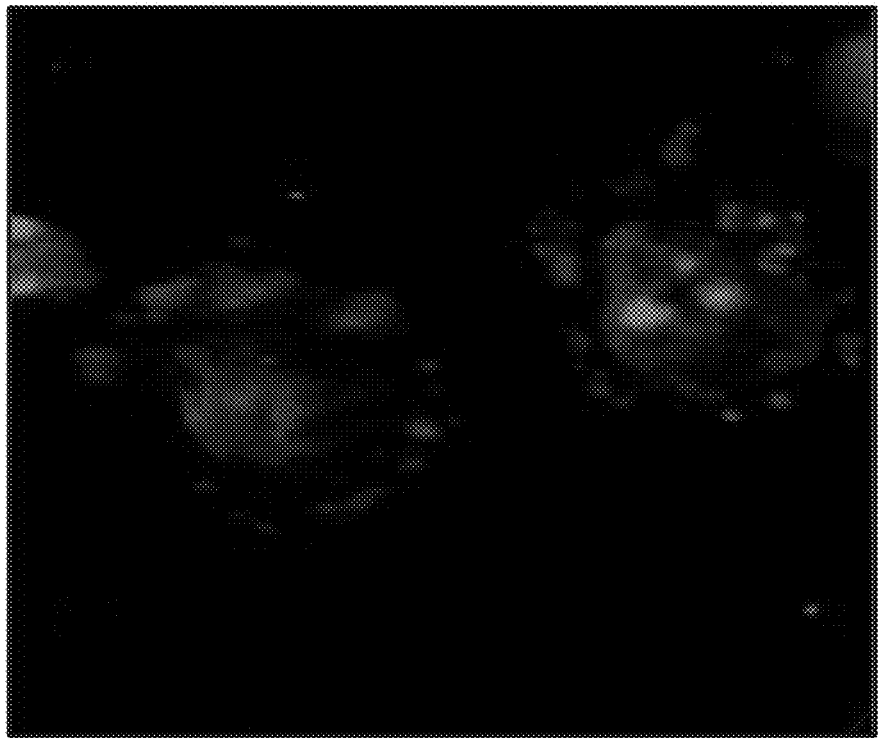
FIGS. 12A and 12B depict the uptake of nanoparticles and loaded with fluorescent BSA by macrophage cells. Raw 264.7 macrophage cells were treated for two hours with poly-β-aminoester ketal-2 or PLGA nanoparticles containing BSA-Alexa Fluor 594 (red—FIG. 12A) and stained with DAPI (blue—FIG. 12B).
Figure 12A:
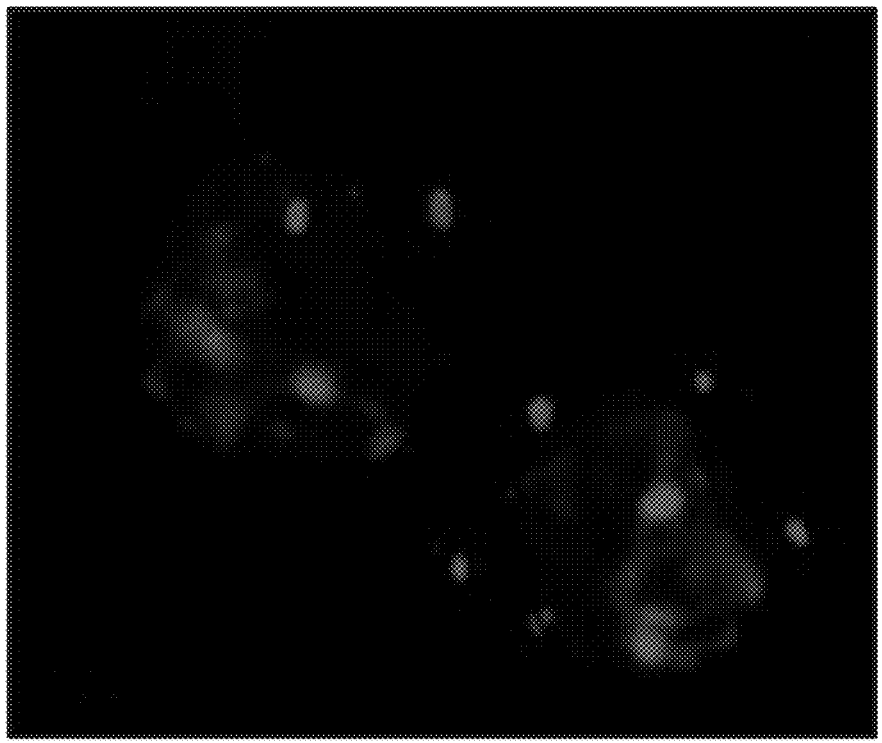

Finally, the uptake of nanocarriers of the present invention by RAW 264.7 macrophages was evaluated by fluorescence microscopy. More diffuse fluorescence was observed from the dual-pH-responsive nanocarriers of the present invention encapsulating labeled BSA, compared with poly lactic-co-glycolic acid (PLGA) encapsulated fluorescent BSA where fluorescence was more punctuate (FIG. 12A). These images indicated that the uptake of poly-β-aminoester ketal-2 nanocarriers and release of fluorescent BSA is enhanced when compared to PLGA nanocarriers (FIG. 12B).

Synthesis of Poly-β-Amino Ester Ketal-1 & 2

The polymers were prepared by Michael addition of the corresponding diacrylates with trimethyl dipiperidine (FIG. 7). Typically, acrylic ketal monomer 4 was synthesized from commercially available reagents by methods known in the art (Heath et al. (2008) *Macromolecules* 41, 719-726). In a vial, diacrylate 4 (5 mmol) and acrylicketal 4 (4.2 mmol) was dissolved in 1 ml DCM followed by addition of 1 ml of TEA. A Teflon®-coated stir bar was added to mix the reactants, and dipiperidine (10 mmol) was added to the vial which was then sealed with a Teflon®-lined screw-cap. The reaction was purged with nitrogen gas. The reaction was stirred at room temperature for four days. The solvent was then evaporated, and the crude polymer was dissolved in 10 ml DCM. The polymer was purified by precipitating it into 2×200 ml hexane to yield 360 mg of the polymer. The polymer was collected and dried under vacuum prior to analysis.

Poly-β-Aminoester Ketal-1

$^1$H NMR (600 MHz, CDCl$_3$)_4.24-4.14 (m, 4H), 3.68-3.57 (m, 4H), 2.85 (d, J=10.3 Hz, 4H), 2.65 (t, J=7.5 Hz, 4H), 2.52 (t, J=7.5 Hz, 4H), 1.93 (t, J=9.9 Hz, 4H), 1.63 (d, J=6.4 Hz, 4H), 1.35 (d, J=9.2 Hz, 6H), 1.26 (d, J=4.3 Hz, 2H), 1.17 (s, 10H).

$^{13}$C NMR (151 MHz, CDCl$_3$)_172.77, 100.36, 100.12, 63.92, 58.97, 54.00, 53.94, 36.86, 35.73, 32.48, 32.32, 24.90, 24.01.

Molecular weight: Estimated by size exclusion chromatography against polystyrene standards in DMF/0.01% LiBr with a VWD (variable wavelength detector) at 250 nm M$_w$=33400, Mn=13300, PDI=2.52

Poly-β-Aminoester Ketal-2

$^1$H NMR (400 MHz, CDCl$_3$)_4.20 (m, 1.6H), 4.07 (t, J=6.6 Hz, 2.3H), 3.64 (m, 1.6H), 2.87 (d, J=9.8 Hz, 4H), 2.67 (t, J=6.9 Hz, 4H), 2.52 (dd, J=16.3, 8.4 Hz, 4H), 1.95 (s, 4H), 1.64 (s, 6H), 1.37 (s, 5H), 1.22-1.19 (br, m, 14H).

$^{13}$C NMR (126 MHz, CHLOROFORM-D)_172.87, 172.72, 100.31, 64.42, 63.88, 58.92, 54.03, 53.95, 53.87, 36.81, 35.69, 32.43, 32.27, 28.58, 25.65, 24.86, 23.96.

Molecular weight: Estimated by size exclusion chromatography against polystyrene standards in DMF/0.01% LiBr with a VWD (variable wavelength detector) at 250 nm M$_w$=6300, Mn=2880, PDI=2.18

Preparation of Dual-Responsive Nanocarriers

In a vial, 25 mg of the synthesized polymer was dissolved in 2.5 ml DCM. The dissolved polymer was added to 50 ml of phosphate buffer (pH 8) containing 1% PVA. The mixture was stirred at 1000 rpm for 10 min to prepare an emulsion. Further emulsification was achieved using a high pressure homogenizer (Microfluidic® 110PS, USA) at 23000 psi for three cycles. The nanocarriers suspension was stirred at 1000 rpm using a magnetic stirrer to evaporate the DCM. Concentrated mode tangential flow filtration system using 500 kDa Pellicon XL cassettes (Millipore, USA) was used to remove the PVA. The nanocarriers suspension was concentrated to 10 ml and washed two times using phosphate buffer (pH 8).39 The pH of nanocapsule suspensions was reduced to 7.4 using KH$_2$PO$_4$ (6.5 w/v %). The pH was acidified to 5 using 0.1N HCl. This nanocarriers solution was used diluted and used to perform the degradation and zeta potential experiments.

Nile Red Containing Poly-β-Aminoester Ketal-2 Nanocarriers

For this study nanocarriers were prepared as described earlier and by addition of 500 μg Nile Red in the DCM used during the single emulsion preparation step. This nanocarriers solution was diluted with buffer and used as such for the performing the degradation experiments using Nile Red.

BSA-Alexa Flour Containing Poly-β-Aminoester Ketal-2 Nanocarriers

Nanocarriers were prepared using double emulsion method W/O/W. Briefly: 5 mg of BSA Alexa Fluor 594 was dissolved in 0.5 ml PBS buffer and emulsified with 5 ml DCM containing 100 mg polymer (poly-β-aminoester ketal-2 or PLGA) using magnetic stirring. The primary emulsion was added to 50 ml 1% PVA in PBS pH 8 and the secondary emulsion was produced. Subsequently further emulsification was achieved similar to before. This nanocarrier solution was diluted and used as such for the fluorescence microscopy.

Cell Toxicity of Nanocarriers

The cytotoxicity of nanocarriers was investigated using a 3-(4,5-dimethylthiazol-2-yl)-2,5-diphenyltetrazolium bromide (MTT) reduction assay. RAW 264.7 macrophage cells were seeded at a density of 15,000 cells/well in a 96 well plate and incubated for 24 h to reach ~60% confluency. Cells were treated with various amounts of nanocarriers that correspond to different amounts of polymer content in them (0.14 μg/ml to 11.4 μg/ml) and incubated for 20 hr. To each well was added 10 μL of MTT solution and incubated for 3 hr. Dimethyl sulfoxide (DMSO, 100 μL) was added to cells to dissolve the resulting formazan crystals. After 20 min of incubation, the absorbance at 570 nm was measured using a microplate reader (Flexstation, Molecular Device Co.). Cell viability was obtained by comparing the absorbance of nanocarrier-treated cells to that of untreated control cells.

Cellular Internalization of Nanocarriers

In summary, in some embodiments of the present invention, two pH response moieties: a pH solubility switch and a pH labile group, were incorporated into the backbone of polymers which were formulated into dual-responsive nanocarriers encapsulating small hydrophobic molecules and/or larger protein payloads. These dual pH-responsive moieties function like a logic gate to fine tune the degradation of, and release from, these nanocarriers. Nanocarrier formulations were stable for 24 hours in healthy physiological pH, and upon reducing the pH to endosomal levels, pH 5, these dual-responsive nanocarriers underwent a rapid and dramatic degradation followed by concomitant release of their Payloads. Without being bound by any theory, the degradation mechanism begins with the protonation of the tertiary amines along the backbone that switch the polymeric nanocarriers from hydrophobic to hydrophilic. The increased uptake of water under acidic conditions then allows the ketal groups to rapidly hydrolyze, giving a bulk degradation profile. In acidic pH, these polymeric nanocarriers degrade into innocuous fragments, namely diols and acetone. Furthermore, the degradation by-product, acetone, is anti-inflammatory, alleviating concerns of an inflammatory response of acidic by-products typical of traditional polyester biomaterials. Such rapid hydrolysis is known to increase the osmotic pressure inside sub cellular compartments leading to cytoplasmic release of encapsulated payloads.

The uptake of Alexa Fluor-594-BSA-loaded nanocarriers was studied in RAW264.7 cells using a fluorescent microscope. Cells were plated on 12 mm cover slides at a density of 10,000 cells per well for 24 hr followed by treatment with poly-β-aminoester ketal-2 or PLGA nanocarriers. The payload in the nanoparticles contained a final concentration of approximately 50 ug/ml Alexa Fluor-594-BSA. After two hours at 37° C., the cells were washed three times with PBS before mounting and staining with DAPI.

Thus, the system of the present invention provides a means for the targeted administration of hydrophilic and/or hydrophobic payloads into target areas of the human body.

Example 2

ROS-Responsive Polymers

In the present invention, novel classes of polymers that can be used to synthesize nanocarriers with linear dual-response mechanisms to increase sensitivity and efficacy of sensing and releasing bioactive agents to targeted, e.g., diseased, environments were developed. One was described supra.

Figure 39:
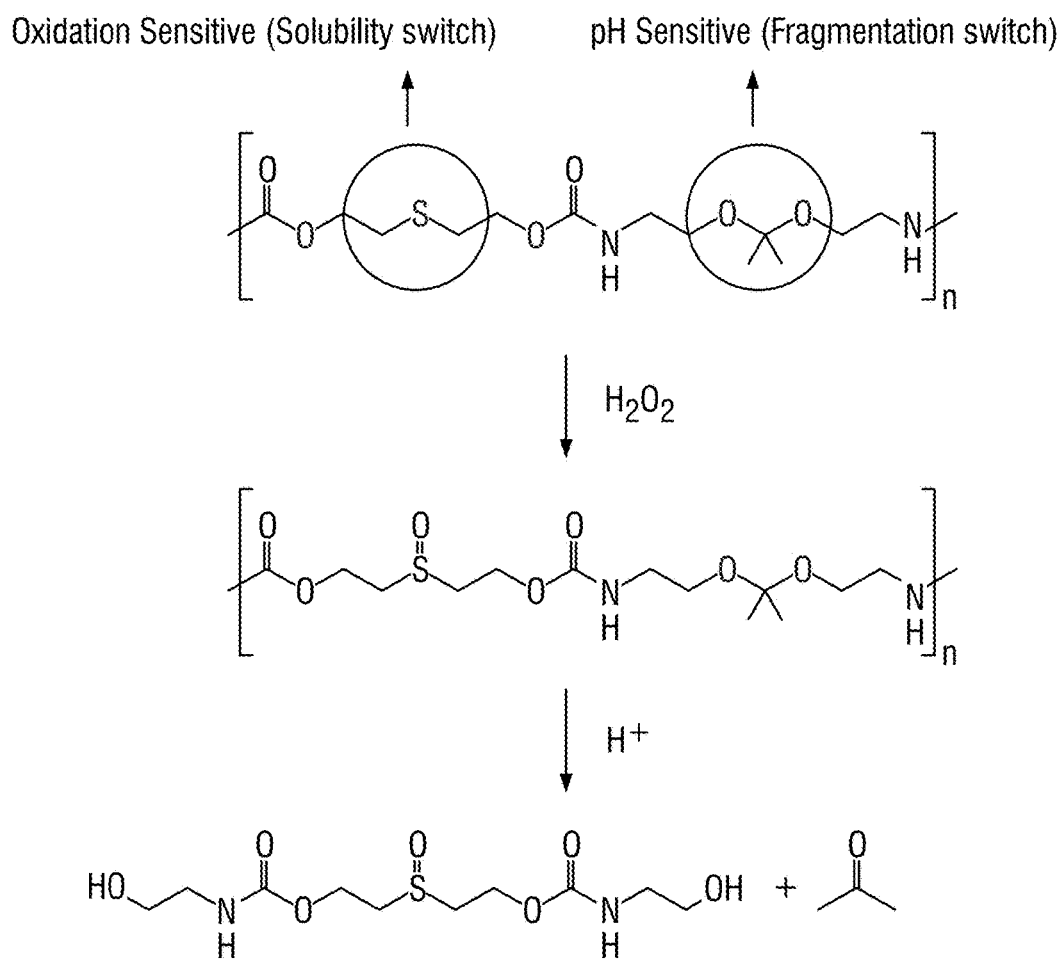
FIG. 39 depicts the degradation mechanism of polythioether ketal. Hydrogen peroxide and acidic pH stimulate the degradation of the polymeric nanoparticles in tandem.

In some other embodiments, the present invention also features a novel poly thioether-ketal that incorporates a thioether moiety in its polymer backbone; the thioether acts as a solubility switch that turns the polymer more hydrophilic when it becomes oxidized from a thioether into a sulfone. Sulfones are inherently more hydrophilic because of a strong dipole due to the presence of the sulfur oxygen double bond; this strong dipole leads to an increased affinity for water, resulting in an accelerated rate of hydrolysis of the ketal groups along the backbone. This allowed polymers of the present invention sharper more rapid degradation kinetics in comparison to conventional polyketals (FIG. 39).

The synthesized poly thioether-ketal nanocarriers of the present invention were prepared to target the oxidative stress areas of many diseases including tumors, atherosclerosis and causes of aging due to mitochondrial damage. Associated with these diseases states and/or abnormalities, reactive oxygen species (ROS) are formed when oxygen undergoes a partial one-electron reduction to super oxide anion, and subsequently forms hydrogen peroxide, hypochlorite peroxynitrite, and other oxidants. Herein, the formulated nanocarriers that are triggered by both ROS and low pH (typical of inflamed tissue), function akin to an "AND" logic gate in circuits. nanocarriers of the present invention will better target diseased tissue for drug delivery or diagnostics. Thus the oxidation stress response allows pH-initiated bulk degradation to occur only in response to mildly acidic environments such as tumors or subcellular compartments.

One frequently occurring ROS is hydrogen peroxide—hydrogen peroxide is a source of oxidative stress and oxidative damage resulting from cellular imbalances of $H_2O_2$ and other reactive oxygen species (ROS). It is connected to cancer (ref 9) and other severe human diseases (ref 10). The polymer of FIG. 5 is designed to respond to mildly oxidative environments. Upon exposure to reactive oxygen species in water, the sulfur group (FIG. 5) will react to form sulfone groups that will increase the hydrophilic character of the polymer coating. This change will promote any hydrophobic payload encapsulated within a nanocarrier made of this polymer to be released; furthermore, in a mildly acidic environment such as in diseased tissue or in cells, the polymer and thus the entire nanocarrier will fragment into innocuous small molecules that can be easily excreted by the body (FIG. 5).

Polymer Synthesis

Figure 13:
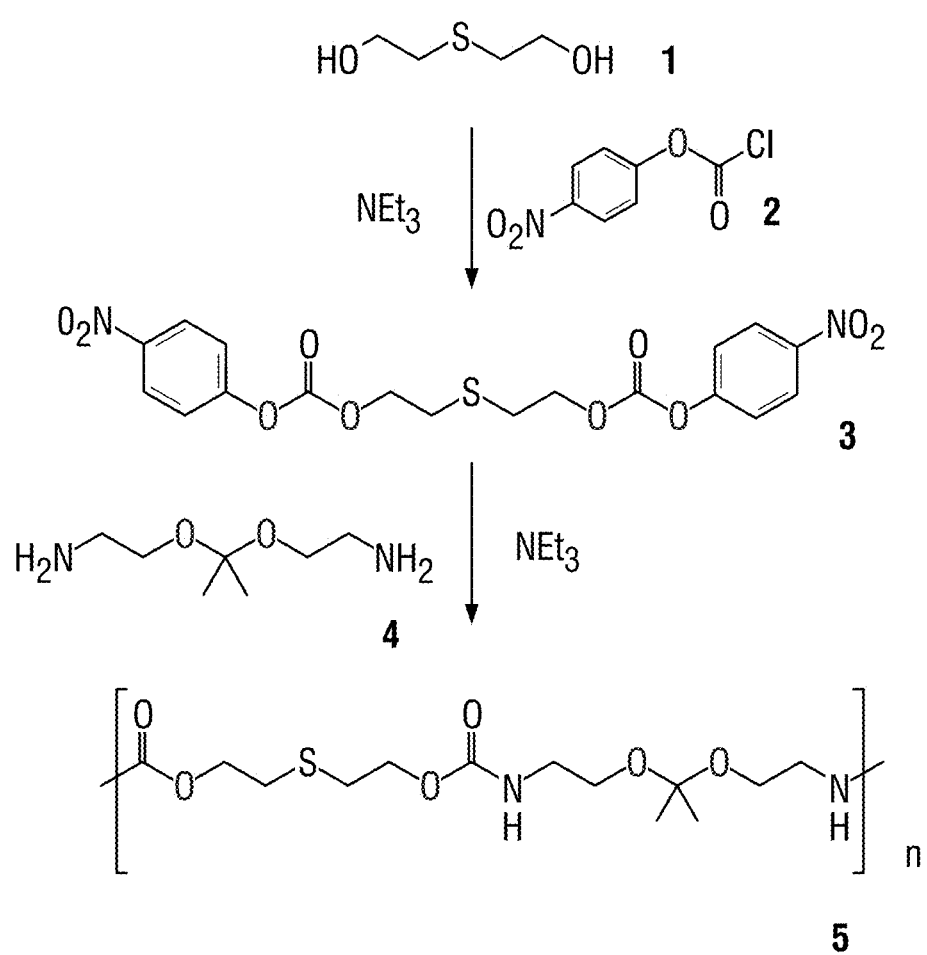
FIG. 13 illustrates the steps in the synthesis of polythioether ketal.

The synthetic scheme for this polymer is shown in FIG. 13. 2,2'-thiodiethanol (compound 1, 3.66 g, 0.03 mol) was taken with 4-nitrophenylchloroformate (compound 2, 13.3 g, 0.064 mol) in a dry round bottom with 125 ml of dry dichloromethane and stirred under a nitrogen atmosphere. To this, triethylamine (30 ml, 0.21 mol) in 25 ml of dry dichloromethane was added drop-wise over 30 min at room temperature. The reaction was subsequently stirred for 4 hrs. At the end of the reaction, the reaction mixture was rotavaped, diluted with 250 ml of dichloromethane, and extracted from 2×100 ml of 1% HCl. The organic layer was dried over MgSO4 and rotavaped. The resulting crude solid was recrystallized from ethyl acetate three times to yield 8.0 g (0.017 mol, 60% yield) of a white solid, MP (138.6-140.10 C). (4-nitrophenyl carbonochloridate may be used instead of 4-nitrophenylchloroformate.)

$^1$H NMR (500 MHz, CHLOROFORM-D)_5.42 (s, 1H), 4.21 (t, J=6.4 Hz, 2H), 3.45 (t, J=5.2 Hz, 2H), 3.30 (d, J=5.3 Hz, 2H), 2.77 (t, J=6.5 Hz, 2H), 1.32 (s, 3H).

13C NMR (126 MHz, CHLOROFORM-D)_156.42, 100.32, 64.24, 64.21, 59.93, 41.20, 31.34, 24.93, 24.90.

Molecular weight: Obtained via GPC against poly styrene standards using DMF (0.01% LiBr) as the eluent.

Mw=59800 Da, Mn=34100, PDI=1.75

Nanocarrier Formation

In o/w procedure, 25 mg of the synthesized polymer was dissolved in 2.5 ml DCM. Then 500 µg Nile red was added to prepare Nile red-containing particles. DCM was added to 50 ml of phosphate buffer (pH 8) containing 1% PVA, and the mixture was stirred at 1,000 rpm for 5 min to prepare an emulsion.

Further emulsification was achieved using a high-pressure homogenizer (Microfluidic® 110PS, USA) at 23,000 Psi for three cycles. The nanocarrier suspension was stirred at 1,000 rpm using a magnetic stirrer to evaporate the DCM. Nile red-containing nanocarriers were filtered through 1 µm filter to remove the insoluble Nile red aggregate, and a concentrated mode tangential flow filtration system with 500 kDa Pellicon XL cassettes (Millipore, USA) was used to remove the PVA and any unencapsulated material. The nanocarrier suspension was concentrated to 10 ml and washed twice.

Protein was encapsulated into the nanocarriers using the w/o/w emulsion method. Briefly, 2 mg Ovalbumin Alexa Fluor® 594 was dissolved in 0.2 ml of PBS buffer and subsequently emulsified with 5 ml of DCM containing 100 mg polymer using probe sonication (stabilized using 2% Span 80) at amplitude of 40% for 5 min (⅛_tip, Misonix S-4000, USA). The primary emulsion was added to 50 ml of 1% PVA in buffer (pH 8) under stirring at 1,000 rpm, and the secondary emulsion was produced. Additional emulsification was achieved using the high-pressure homogenizer at 23,000 Psi for two cycles and tangential flow filtration was accomplished as previously described. Finally, 5% Trehalose was added to the particles before lyophilization. The lyophilized particles were suspended in aqueous media at different pHs and $H_2O_2$ levels for further evaluation of stability or release.

The encapsulation efficiencies of the particles were determined by incubating them at acidic pH in presence of 100 mM $H_2O_2$ until no further particles are detected by the DLS and the detected fluorescence reaches its maximum.

Dynamic Light Scattering Measurements of the Nanocarriers

Nanocarriers were suspended in a phosphate buffer pH 7.4 or pH 5 in presence or absence 100 mM $H_2O_2$, with stability determined by monitoring their size for 24 hrs via dynamic light scattering (DLS) using a Zetasizer-ZS (fixed attenuator of 7, Malvern Worcestershire, UK).

Effect of pH and $H_2O_2$ on Nile Red Release

Nile red was encapsulated into the nanocarriers as a sensor of changes in the hydrophobic-hydrophilic character of the surrounding environment. Nile red fluoresces in the hydrophobic environment inside the nanocarriers and quenches once released into the aqueous release media; this quenching was measured as an indicator of Nile red release into an aqueous media. Nanocarrier powder was dispersed in PB pH 7.4 or 5 in presence or absence 100 mM $H_2O_2$. The pH was checked in the presence of $H_2O_2$ to confirm the pH. Samples were taken and Nile red fluorescence was determined at different time intervals. Decrease in the nanocarrier fluorescence was indication of Nile red release to the aqueous media.

Effect of pH and $H_2O_2$ on Ovalbumin Release

Nanocarrier powder was dispersed in PB pH 7.4 or 6.5 in presence or absence 100 mM $H_2O_2$. PB pH 6.5 was chosen for ovalbumin release study to prevent its precipitation upon release into PB having pH near ovalbumin isoelectric point (pH~5) (Smith, E. R. B. (1935) J. Biol. Chem. 108, 187-94). Samples were taken at different time intervals and spun down at 20K×g for 10 min at 4° C. The supernatant was analyzed for released ovalbumin Alexa Fluor® 594 after appropriate dilution.

Degradation of the Poly Thioether-Ketal by $^1$H NMR 10 mg of the polymer were taken with deuterated a) 1:1 acetonitrile-water (pH=5, phosphate buffer); b) 1:1 acetonitrile-water (pH=5, phosphate buffer) with 20 µl of H2O2; the 1H NMR was obtained at regular intervals.

Cell Toxicity of Nanocarriers

The cytotoxicity of nanocarriers was investigated using a 3-(4,5-dimethylthiazol-2-yl)-2,5-diphenyltetrazolium bromide (MTT) reduction assay. RAW 264.7 macrophage cells were seeded at a density of 15,000 cells/well in a 96-well plate and incubated for 24 hrs to reach 60% confluency. Cells were treated with various amounts of nanocarrier that corresponded to the varying amounts of polymer contained in them (0-300 µg/ml) and incubated for 20 hrs. To each well was added 10 µL of MTT solution, and the wells were incubated for 3 hrs. Dimethyl sulfoxide (DMSO, 100 µL) was added to cells to dissolve the resulting formazan crystals. After 20 mins of incubation, the absorbance at 570 nm was measured using a FlexStation microplate reader (Molecular Devices, Inc., Sunnyvale, Calif., USA). Cell viability was obtained by comparing the absorbance of nanocarrier-treated cells to that of control cells not treated with particles.

Cellular Internalization of Ovalbumin-Containing Nanocarriers

The uptake of ovalbumin Alexa Fluor®594-loaded nanocarriers was studied in RAW264.7 cells using a fluorescent microscope. Cells were plated on CultureWell Chambered Coverglass slides (Life Technologies, Carlsbad, Calif., USA) at a density of 10,000 cells per well for 24 hrs followed by treatment with poly thio-ketal or PLGA nanocarriers. The nanocarrier payload contained a final concentration of approximately 10 µg/ml ovalbumin Alexa Fluor® 594. After 8 hrs at 37° C., the cells were washed with PBS before mounting and staining with DAPI.

As noted above, infected tissues are frequently characterized by a decreased pH and the presence of reactive oxygen species (ROS).

In order to simulate infected tissues, which are frequently characterized by a decreased pH and the presence of reactive oxygen species (ROS), particle behavior was tested at acidic pH and in the presence of $H_2O_2$, which is a prevalent reactive oxygen species. Accordingly, nanocarriers were subjected to different physiologically relevant conditions: pH 7.4 (pH of healthy tissue), pH 7.4/100 mM $H_2O_2$ (presence of ROS), acidic pH, and acidic pH/100 mM $H_2O_2$. Their behavior was monitored via DLS and by measuring the release of Nile red and ovalbumin.

Figure 14:
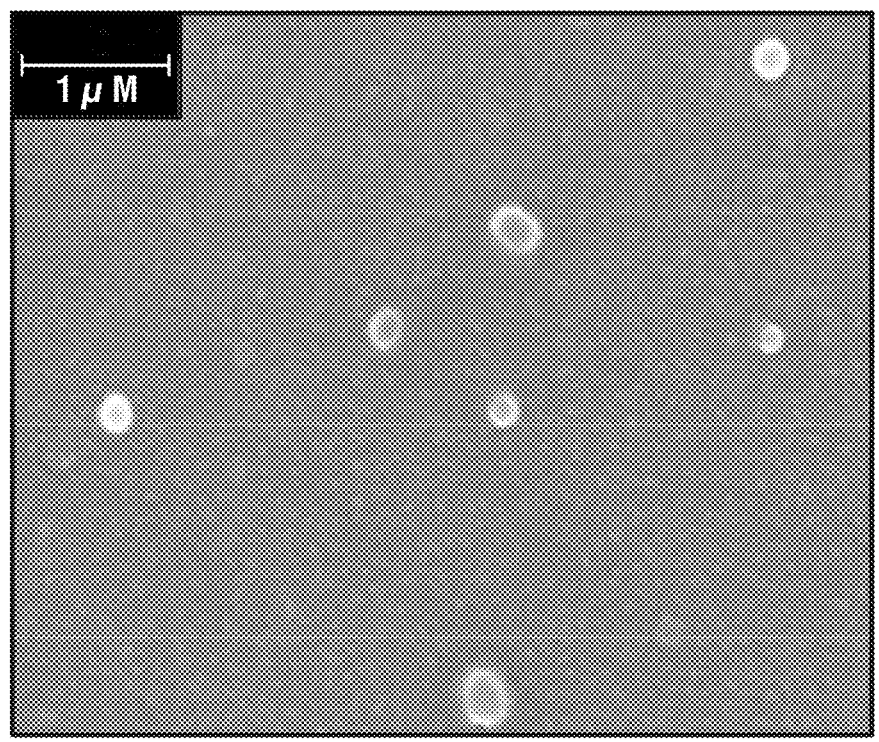
FIG. 14 is a SEM image of the nanoparticles showing a particle diameter of <1 μm.

The hydrophobic nature of the polymer permitted the formulation of the nanocarriers using single- or double-emulsion techniques. This in turn allowed the encapsulation of different payloads with different hydrophobic-hydrophilic characteristics like Nile red and ovalbumin (FIG. 14).

Figure 15:
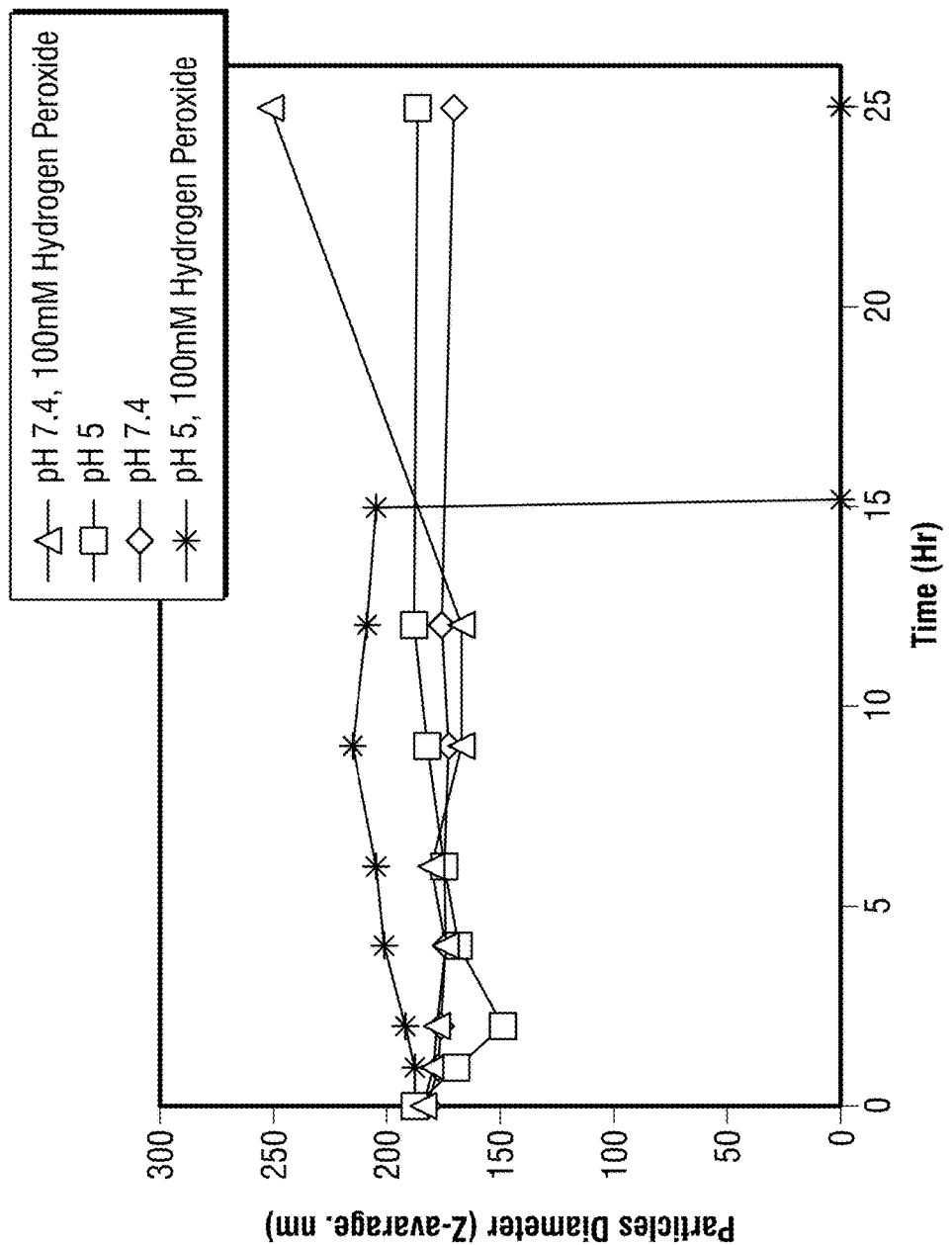
FIG. 15 plots the effect of pH and $H_2O_2$ on the Z-average of the nanoparticles. Triplicate measurements were taken using the DLS at a fixed attenuator of 7.

Monitoring the behavior of the nanocarriers using DLS (FIG. 15) showed that only nanocarriers dispersed in pH 5 in the presence of $H_2O_2$ degraded within 24 hrs, while the particles dispersed in pH 5 alone remained detectable throughout this time period. Thus, the presence of both stimuli caused an accelerated degradation of the nanocarriers. This is further evidenced by the observed increase in particle size upon incubation in $H_2O_2$ at pH 7.4. This swelling is due to the backbone becoming oxidized, resulting in the hydration of the particles.

Figure 16:
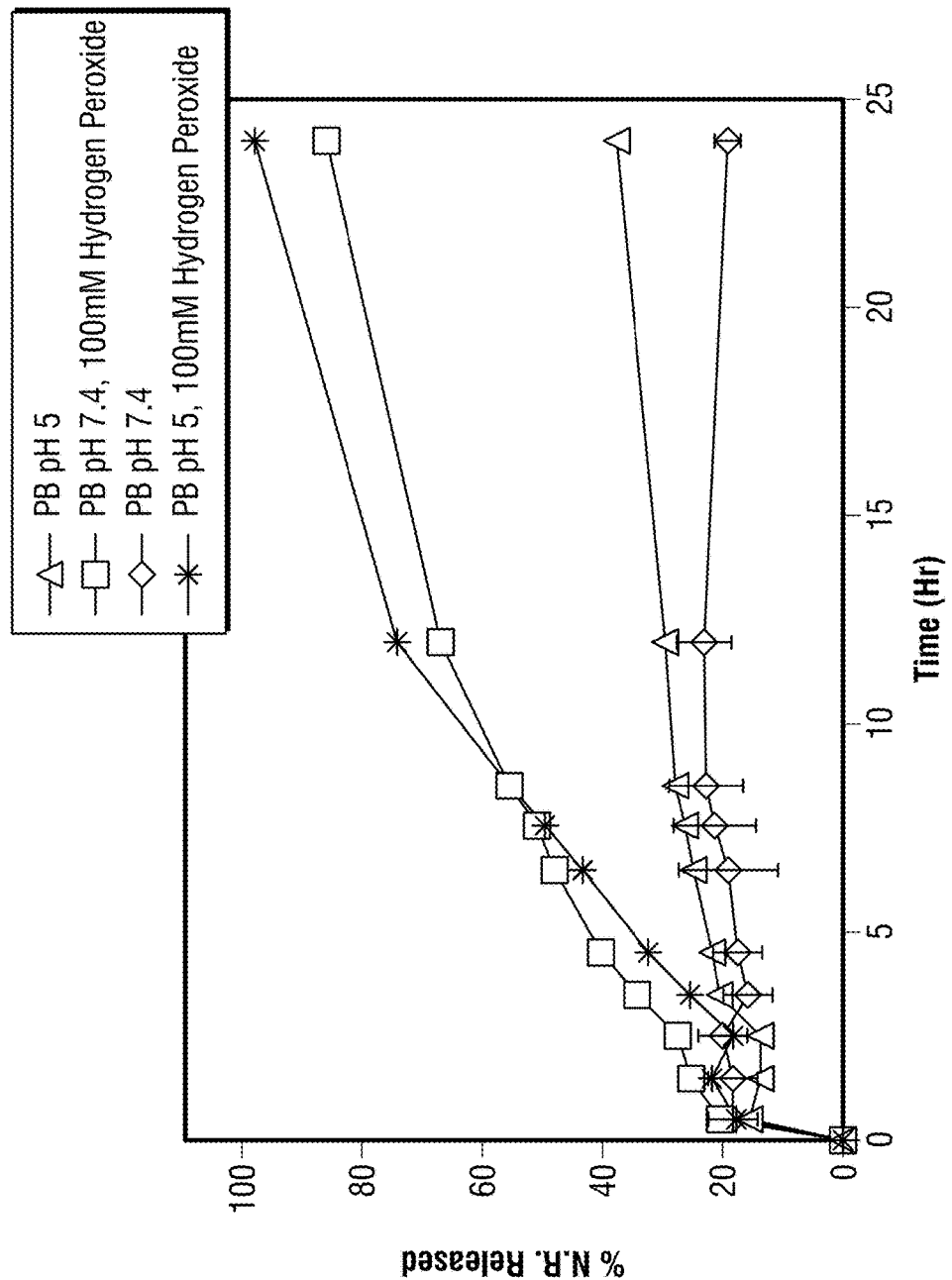
FIG. 16 plots the release of Nile red from polythioether ketal nanoparticles. Decrease in nanoparticle suspension fluorescence was correlated to Nile red release in different conditions.

When Nile Red is encapsulated in the particles it acts as a fluorescent probe of hydrophobicity and release. In presence of $H_2O_2$, oxidation of the polymer backbone occurs, rendering the nanocarriers more hydrophilic. This causes quenching of encapsulated Nile red upon its release from the nanocarriers (Z-average=200 nm). This hydrophilic change occurred in both neutral and acidic conditions and depended entirely on whether the particles were incubated in hydrogen peroxide or not (FIG. 16). Also, Nile red was minimally quenched at pH 5 due to the slow degradation of the particle via surface erosion. However, more quenching is observed when both conditions are operational.

Figure 17:
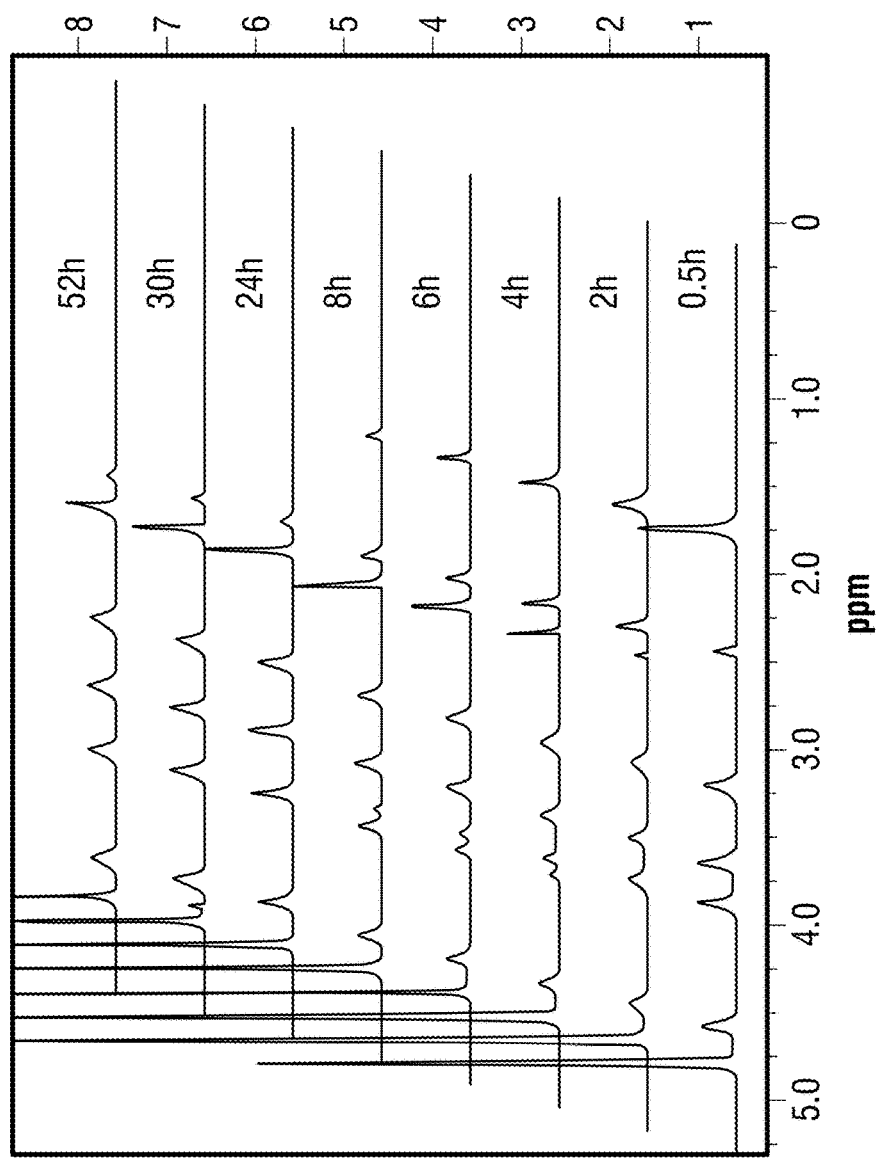
FIG. 17 plots degradation of polymer 5 at pH 5 in 1:1 deuterated acetonitrile and water by 1H NMR. Hydrolysis of ketal is evidenced by the appearance of acetone peak (at δ2.6 ppm) and disappearance of the ketal peak (at δ1.6 ppm). There is also a concomitant change in the peak at δ3.8 ppm to δ3.9 ppm due to the formation of alcohol upon degradation of the ketal.
Figure 18:
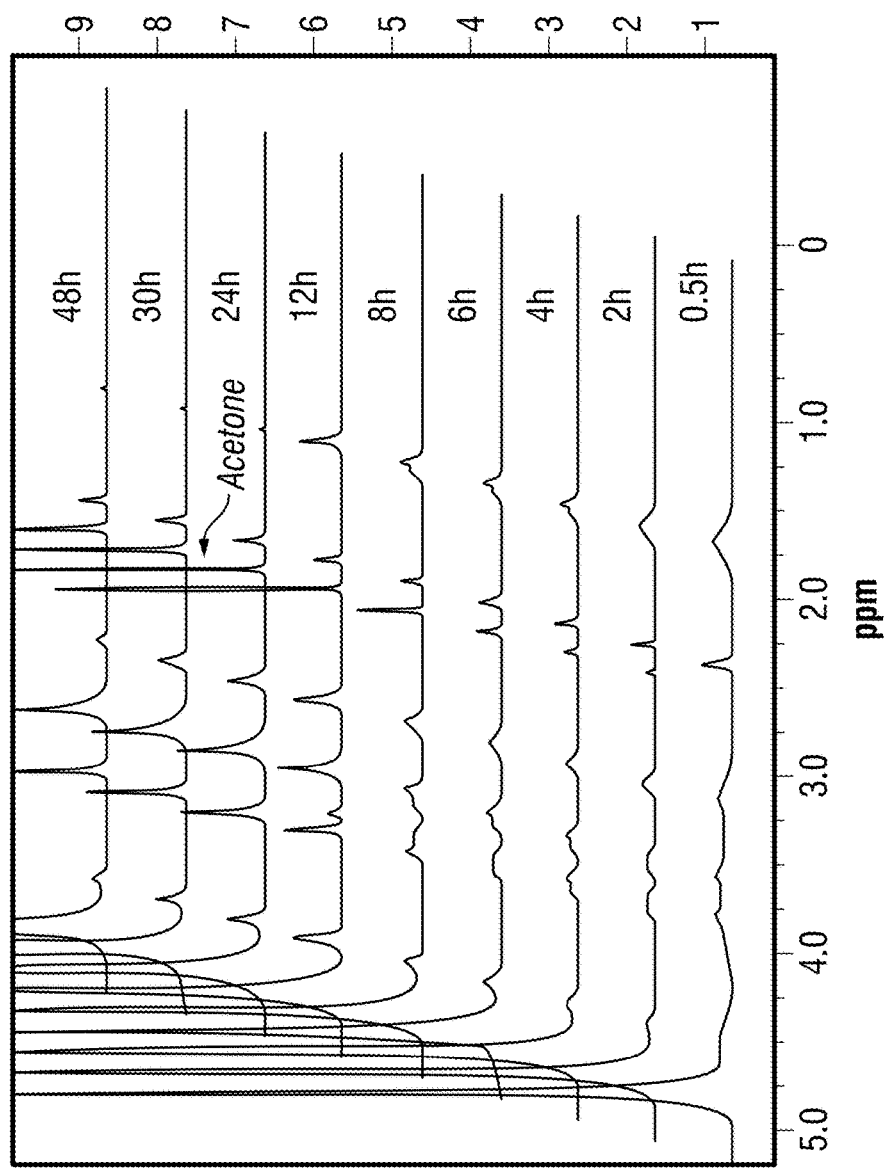
FIG. 18 plots degradation of polymer 5 at pH 5 in 1:1 deuterated acetonitrile and water with addition of 20 μl of 30% $H_2O_2$ by $^1$H NMR. In addition to the changes noted in the FIG. 6, upon addition of $H_2O_2$ we see that the peak at δ3.6 ppm shifts to δ3.7 ppm. This is consistent with the oxidation of sulfur in the backbone to a sulfoxide. These NMR studies establish that the sulfur moiety undergoes oxidation when subjected to $H_2O_2$.

Finally, in order to confirm that our polymer degrades under the said conditions, we performed degradation and analyzed via 1HNMR (FIGS. 17 and 18). Here, as expected, we did not see a difference in polyketal hydrolysis rates because the polymer is completely dissolved without the need of oxidation. The control that we observed in the rates of particle degradation is due to the nanocarrier's architecture, which is lost when the polymer is dissolved. This systemic control was subsequently tested by releasing ovalbumin as a model protein.

Figure 19:
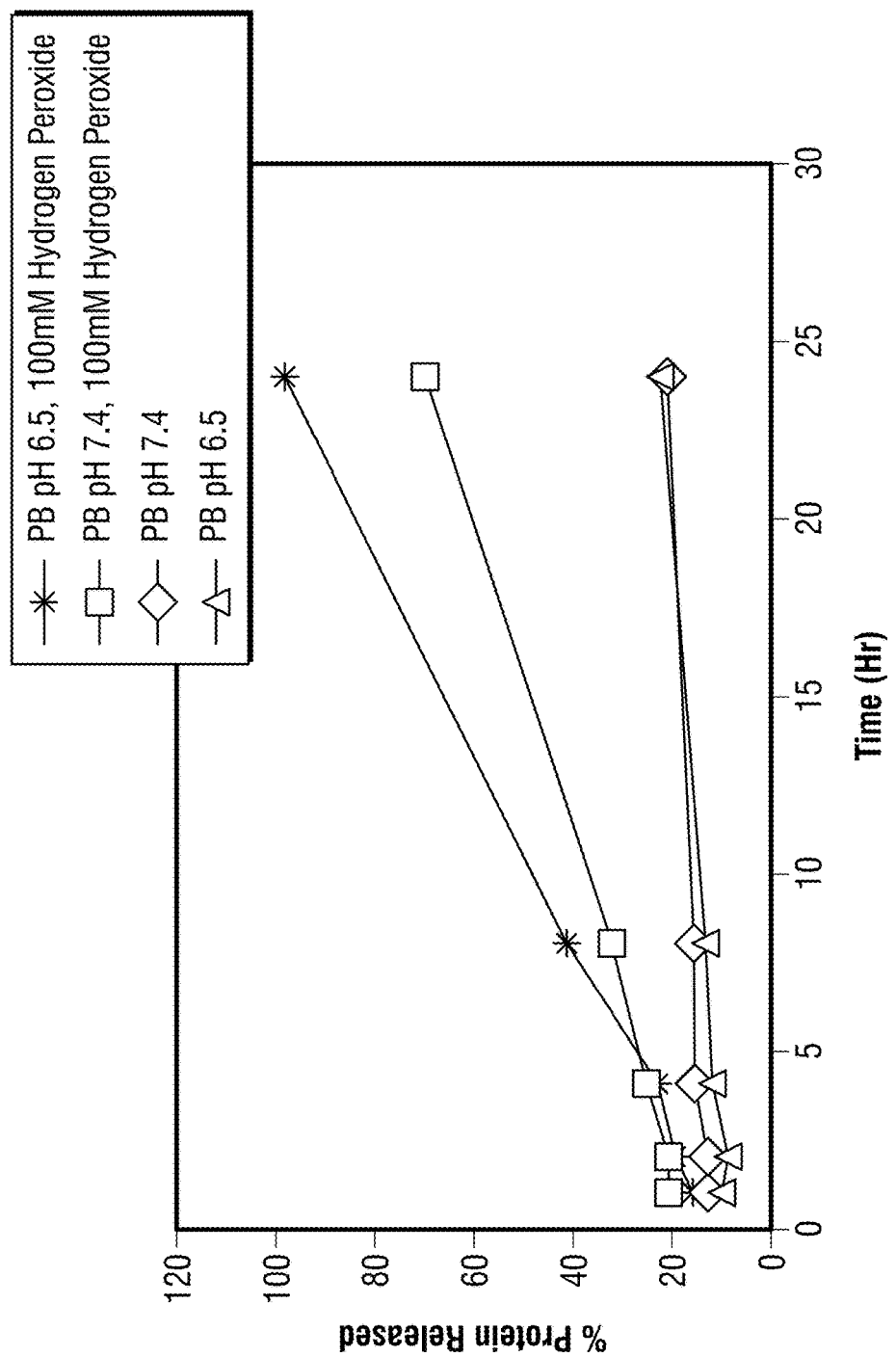
FIG. 19 plots the release of ovalbumin AlexaFluor 488 from polythioketal stained with DAPI (blue) nanoparticles. Nanoparticle supernatants were tested for fluorescence to determine ovalbumin release profile over time (n=3).

FIG. 19 shows that ovalbumin release was initiated by oxidation of the polymer, or more accurately due to swelling of the nanocarriers. Meanwhile, higher release was observed at acidic pH in the presence of hydrogen peroxide due to degradation of the nanocarriers. Importantly, the nanocarriers showed excellent stability at neutral 7.4. Furthermore, the full degradation of our new nanocarriers system is important as small fragments are more readily excreted.

The cytotoxicity of poly thio-ketal nanocarriers in cells was evaluated using the MTT assay using RAW264.7 cell line. The RAW264.7 macrophage cell line is an excellent model system for studying immune response and can produce relatively higher levels of endogenous ROS. Additionally, these cells are able to take up particles very readily without the need of cell penetrating peptides.

Figure 20:
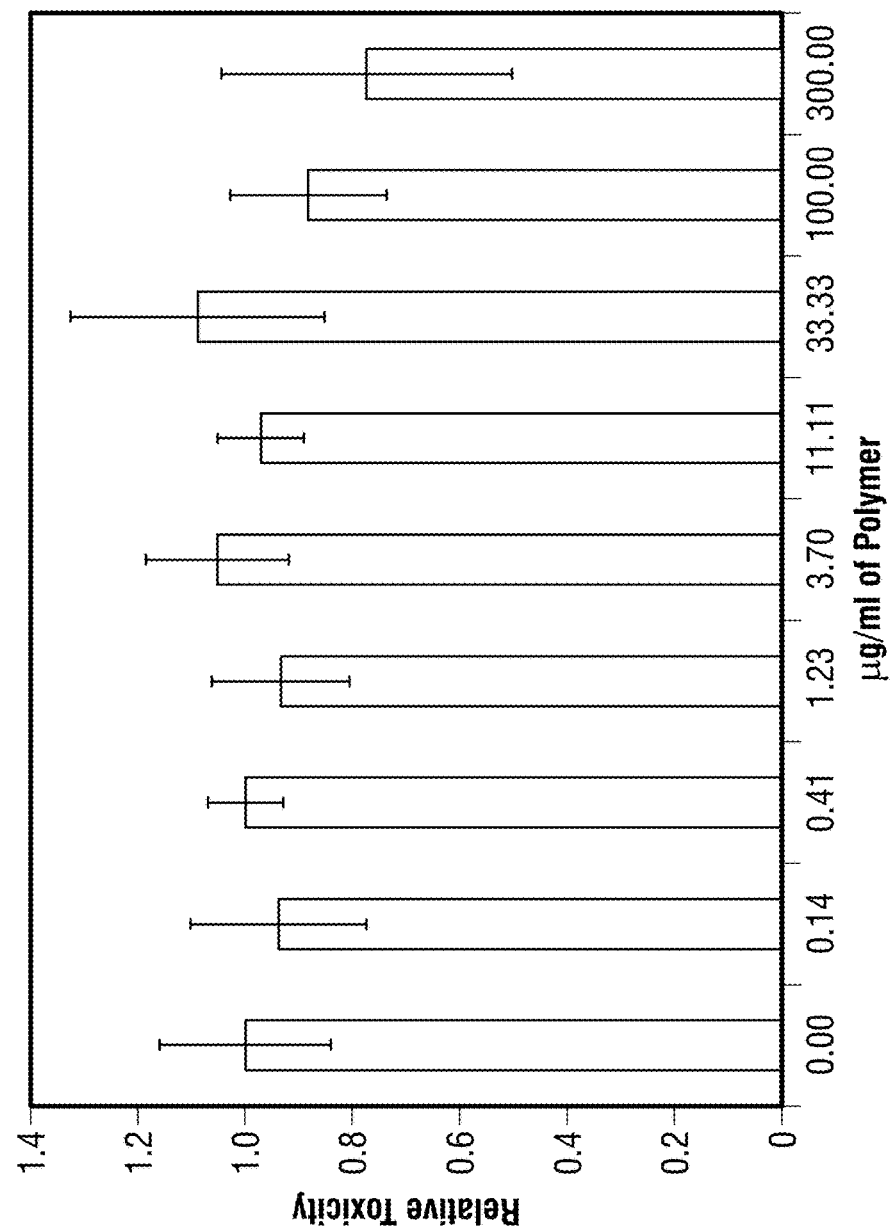
FIG. 20 plots the cytotoxicity of polythioether ketal nanoparticles at different concentrations in RAW 264.7 macrophage cells. The cells were incubated with the nanoparticles for 20 h before performing the MTT assay.
Figure 21:
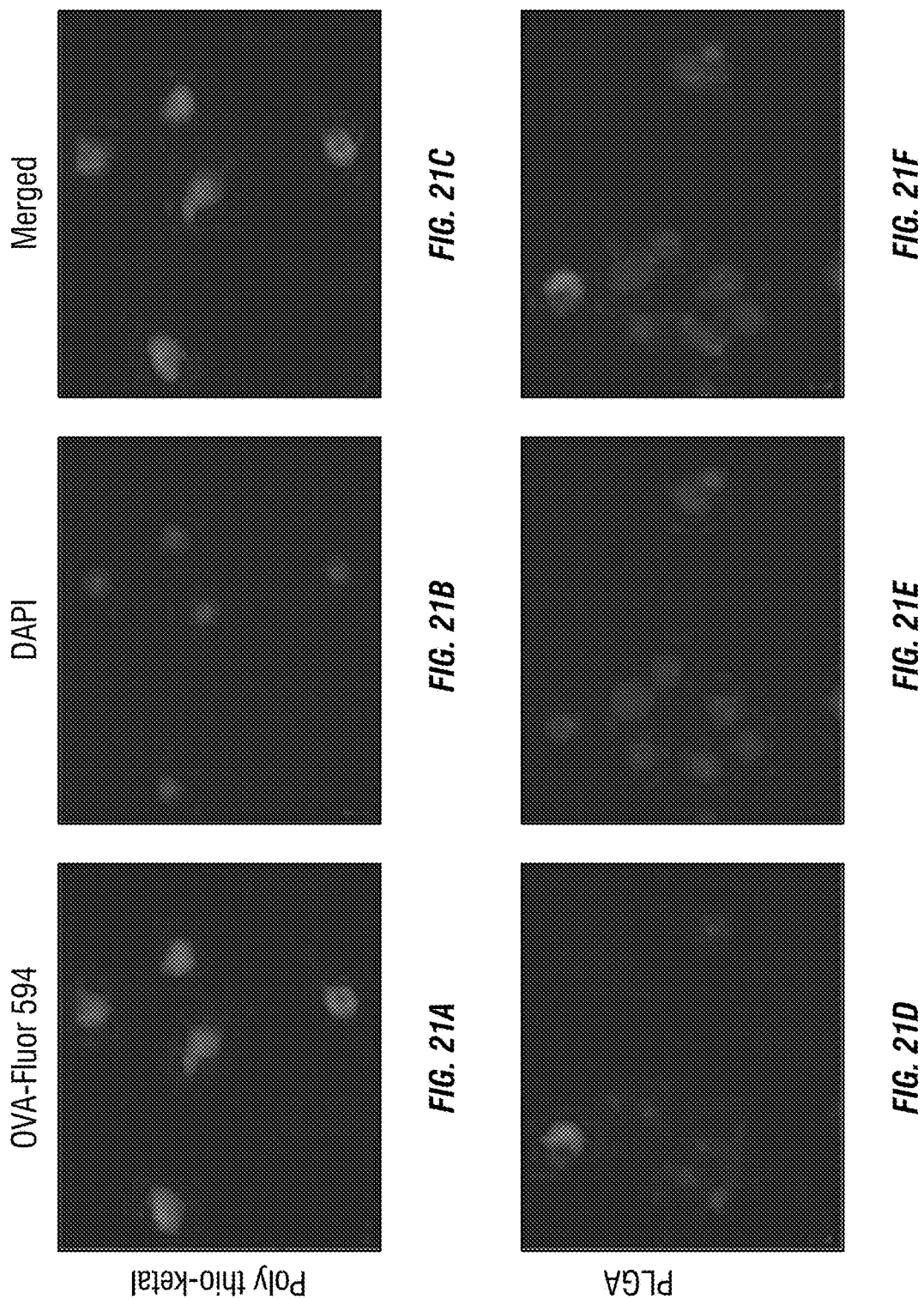
FIGS. 21A-21F are micrographs showing the uptake of nanoparticles loaded with fluorescent ovalbumin. Raw 264.7 macrophage cells were treated for 8 h with polythioether ketal (FIGS. 21A-21C) or PLGA (FIGS. 21D-21F) nanoparticles containing ovalbumin Alexa Fluor 594 (red) and with DAPI (blue).

RAW 264.7 cells were incubated with various amounts of nanocarriers for 20 hr. FIG. 20 illustrates the comparison of cytotoxicity between cells treated with increasing concentrations of poly thioether-ketal polymer. There was no significant cytotoxicity observed with the cells incubated with up 300 µg/ml of polymer (p=0.294). Finally, the cellular uptake of nanocarriers and release of cargo within cells was analyzed by comparing poly thioether-ketal and PLGA nanocarriers containing equal amounts of fluorescently-labeled ovalbumin, shown in FIGS. 21A-21F. Nanocarriers were added to RAW 264.7 cells and evaluated by fluorescence microscopy. Poly thioether-ketal nanocarriers were able to efficiently deliver protein within RAW264.7 macrophage cells that have an $H_2O_2$ concentration of 2 µM 33.

Cells treated with poly thioether-ketal nanocarriers show thorough diffusion of ovalbumin throughout the cytoplasm and nucleus, indicating that labeled ovalbumin was released within the cell. This is in contrast with slow-degrading PLGA nanocarriers that show punctuated spots and less diffused ovalbumin throughout the cell.

In summary, in some embodiments of the present invention, a polymeric nanocarrier with two stimuli responsive moieties in its backbone is synthesized. This nanocarrier undergoes programmed degradation when stimulated by inflammatory cues, ROS and acidic pH, respectively. This system functions akin to an 'AND' Logic Gate. Upon stimulation by ROS, the polymer becomes hydrophilic, followed by ketal hydrolysis promoted at an acidic pH. A release of small hydrophobic molecules, Nile red, in acidic pH and an increase in polymer hydrophilicity upon oxidation was observed.

Higher release of encapsulated ovalbumin was observed in the presence of both hydrogen peroxide and at acidic pH. The nanocarriers were readily taken up by macrophage cells, and that ovalbumin release from the nanocarriers into the cytoplasm was in agreement with the degradation behavior of the nanocarriers as shown in the DLS measurements. This shows that nanocarriers of the present invention can differentiate between the conditions of the target areas from other areas. This ensures the release of the payload in specific diseased regions such as inflammatory or tumor sites and further allows for intracellular delivery. These studies suggest that nanocarriers of the present invention can be applied to the delivery of diagnostics and therapeutics to sites of inflammation.

Example 3

Nanocarriers

In some embodiments of the present invention, nanocarriers are synthesized from the molecularly-engineered polymer. Such nanocarriers may have altered properties by, for example, altering the hydrophobic nature of the polymer backbone of the nanocarriers. Nanocarriers of the present invention were characterized with regard to morphological properties, particle size, charge, nano- and micro-sphere stability, and robustness as part of the process to determine the optimal bioactive delivery vehicles for a range of therapeutic and/or diagnostic applications.

Figure 22:
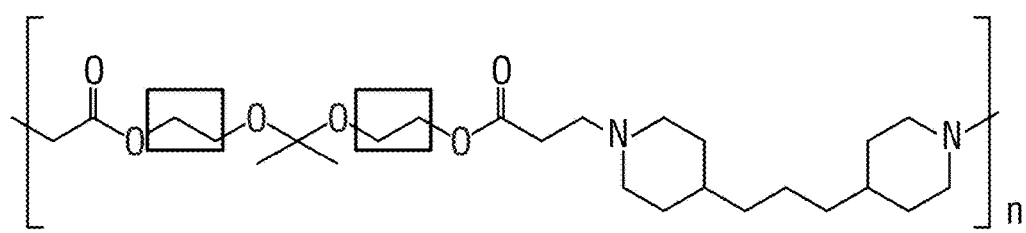
FIG. 22 indicates where the polymer may be modified at specific sites (as indicated in the box) for altered hydrophobicity and crystallinity to study and determine optimal characteristics for polymeric nanocarrier formation.

The hydrophobicity of the polymers may be varied in order to select the optimal polymer structure for nanocarrier formulation (for example, as shown in FIG. 22) and degradation profile. Using double emulsion condensation, nanocarriers are/were formulated using these novel polymers and their quality and stability was characterized.

Figure 23:
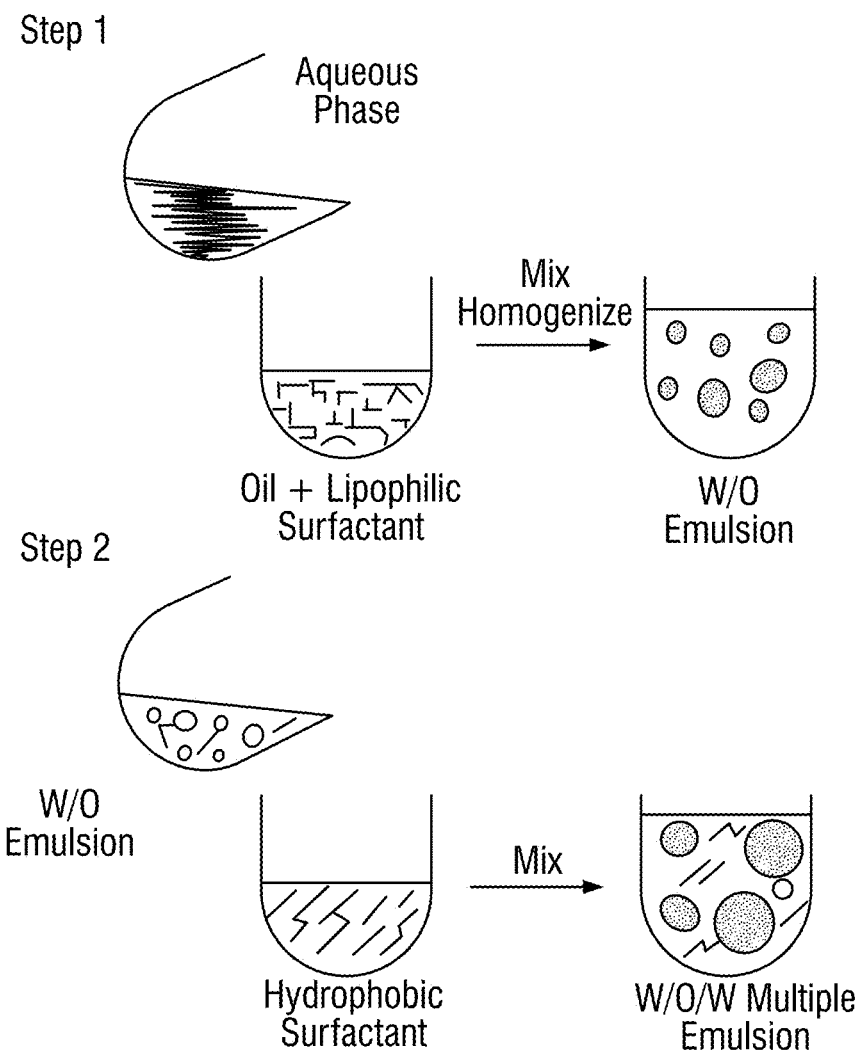
FIG. 23 is a schematic illustration of two-step emulsification of W/O/W double emulsions. A primary emulsion is formed with the bioactive in aqueous solution (W1) encapsulated in an organic phase (O) that contains polymer of the present invention.

The water-oil-water double emulsion technique is a two-step microencapsulation process as shown in FIG. 23. A primary emulsion is formed with the bioactive in aqueous solution (W1) encapsulated in an organic phase (O) that contains polymer of the present invention.

Homogenization is used to obtain a stable W/O emulsion. This primary emulsion is then emulsified with the addition of surfactants in external aqueous solution (W2) to create a W1/O/W2 double emulsion. The polymeric nanocarriers are/were finally isolated through centrifugation, washed several times with water and dried.

Morphology of the polymeric nanocarriers is/was analyzed using scanning electron microscopy (SEM). Particle size and polydispersity can be determined by photon correlation spectroscopy using a Zetasizer. In addition to polymer characteristics, the polymeric nanocarriers will also be assessed for stability to various processing procedures, including suspension, drying, resuspension, centrifugation, etc.

Example 4 pH-Responsive Polymer and its Use as a MRI Contrast Agent

The potential impact and benefits of improving molecular imaging are broad and large. Better methods for molecular imaging promise pharmaceutical scientists a method to monitor drug behavior in a more accurate, and cost-effective manner. In the clinical arena, molecular imaging promises early diagnosis of disease, an advantage which in general leads to more effective treatment. Approaches that advance molecular imaging include targeted agents and activatable agents (also known as 'smart' or 'sensing' agents). These approaches aim to enhance the signal to background ratio at the desired tissue. Despite the potential of contrast activation, it remains in the early developmental stage, most especially for multivalent activatable contrast agents.

As described above, gadolinium (Gd) is a frequently used MRI contrast agent, but one that may be improved. A longer circulation time would provide better bioavailability and ultimately better contrast. A challenge is to create a macromolecular Gd contrast agent able to carry a large load of Gd plus give higher relaxivities and tissue contrast, but yet be able to degrade rapidly to facilitate rapid renal clearance, and thus minimize Gd-associated toxicity.

Figure 24A:
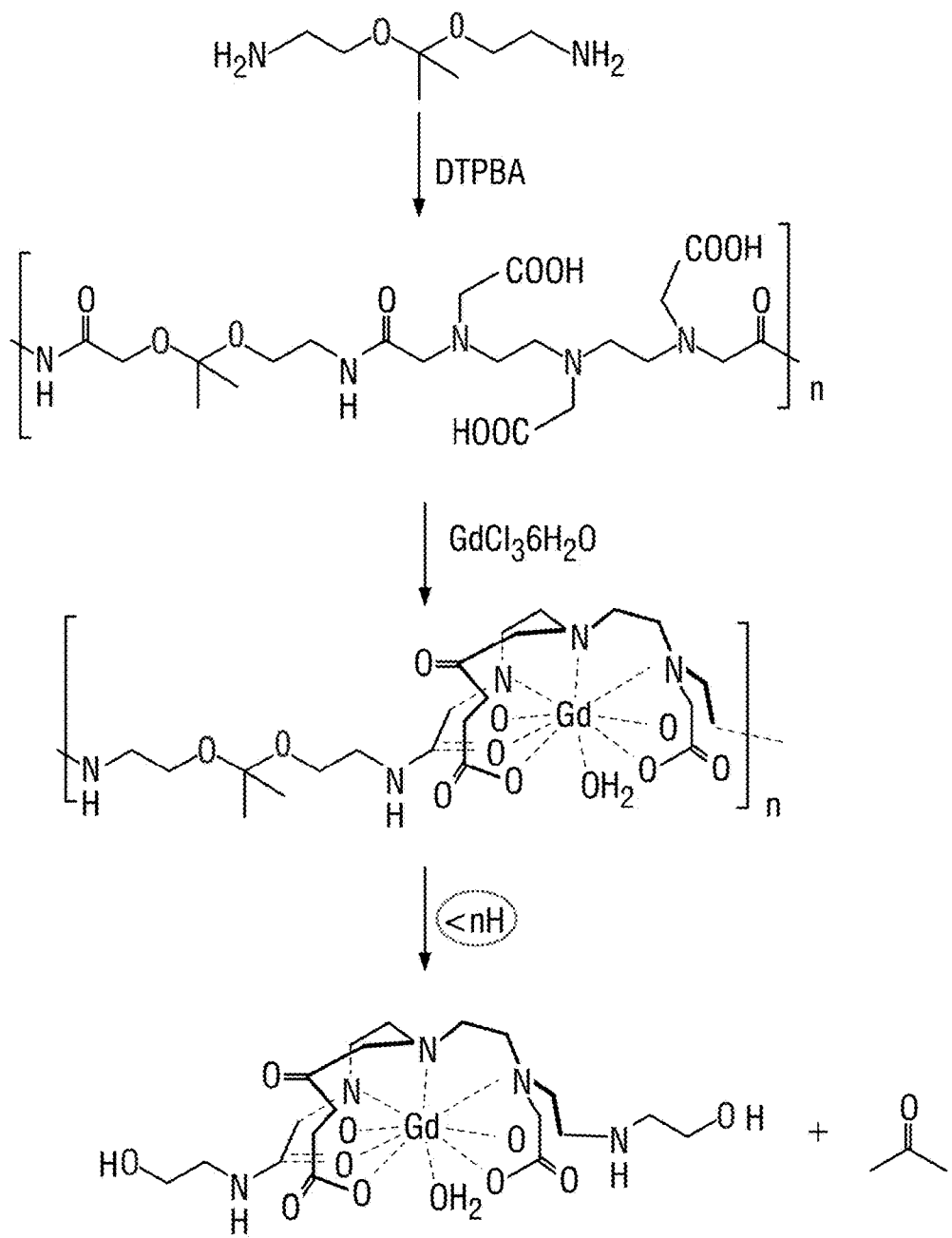
FIGS. 24A-B depict the synthesis and degradation of the pH-degradable polymer (FIG. 24A) and control polymer (FIG. 24B) containing gadolinium.
Figure 24B:
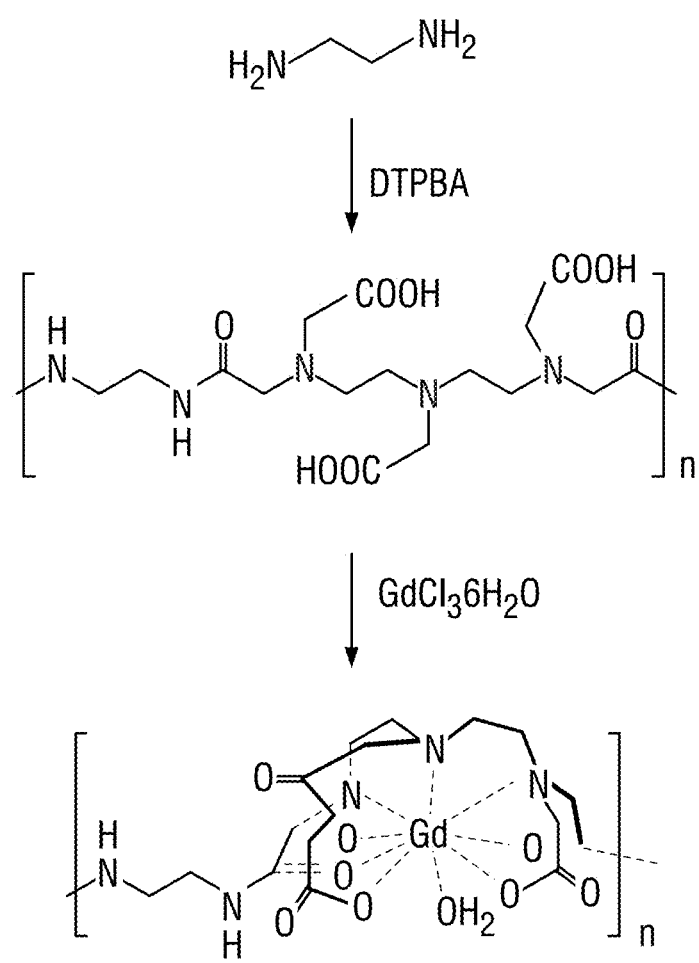

FIG. 24A depicts the structure and degradation of the polymer CAs of the present invention. A second, non-degradable control polymer (FIG. 24B) was also formed, lacking the acid-labile ketal moiety in the backbone. The synthesis and characterization, relaxivity measurements, and in vivo imaging and Gd concentration profiles of both polymer CAs were documented. With the polymers of the present invention pH-dependent polymer degradation occurs rapidly, even at physiological pH values, and, further, this degradation leads to relaxivity changes. Finally, the degradable contrast agent of the present invention offers better contrast and a similar clearance in vivo as commercially available Magnevist®.

Polymer chelates of Gd affect the local water relaxation rate more strongly than monomeric chelates. When polymer chains are broken into smaller fragments whose tumbling frequency is more rapid, their relaxivity decreases. In the present invention, a polymer contrast agent which degrades in physiological conditions would have a higher relaxivity while simultaneously retaining its ability to be cleared rapidly, lowering the effective toxicity of the Gd.

The polymer chelate of the present invention incorporates a metal chelating group for coordination with Gd and a ketal moiety for degradation by hydrolysis. Previous work utilizing ketal hydrolysis as the acid-labile moiety has led to the development of pH-degradable polymers for use in nanocarriers.

Figure 25B:
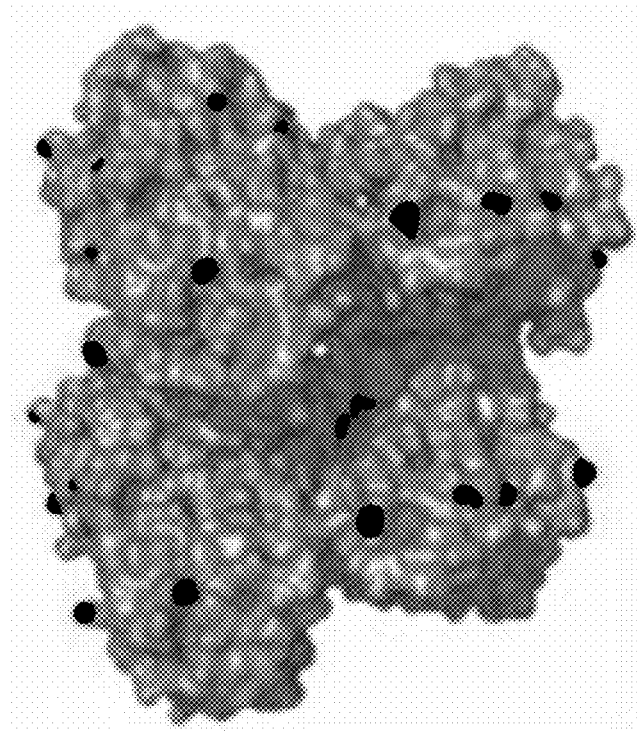
FIG. 25B illustrates the crystal structure of ovalbumin with amino groups highlighted. These amino groups can be used to attach a chelator to the protein.
Figure 25A:
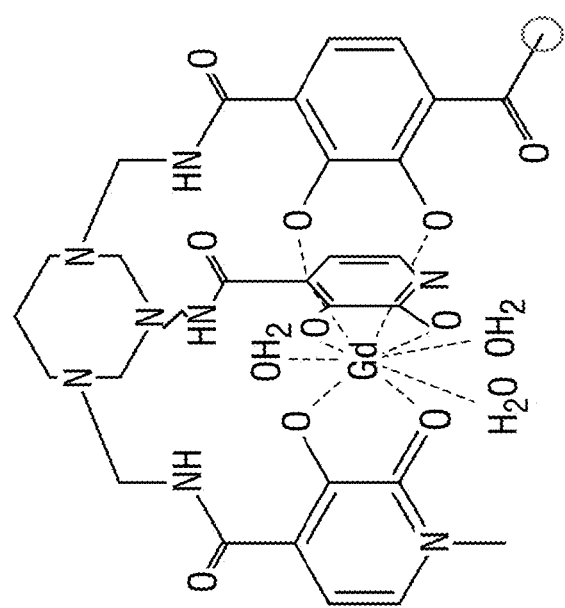
FIG. 25A depicts the chemical structure of triazacyclononane hydroxypyridinone (TACN-HOPO)-based Gd(III) chelates developed by Raymond and coworkers; these have a high hydration number (q=3). combined with high aqueous solubility, fast water exchange, and slow electronic relaxation, which features make these compounds promising as high-relaxivity agents for future MRI applications (r1p~14 mM −1s−1, 60 MHz). The x on the chemical structure symbolizes a good leaving group by which the chelator can be attached to a nucleophile on a protein. In various non-limiting specific embodiments, x is NHS, CL, Maleamide, or PNP.

Imaging of biochemical events by MRI is limited by the sensitivity of the method to probe concentrations in tissue. Thus, the next generation of activatable contrast agents should be designed in view of this problem. In general, a collective response of all the encapsulated agents can overcome this sensitivity issue, while providing a new means of visualizing specific biological events. Controlled deactivation/activation strategies should focus on the water exchange rate and the water spheres. This is especially important in light of the new generation of Gd-chelates with high water coordination spheres (IS), and fast water exchange rates (FIG. 25). Encapsulation of a large payload of hydrophilic protein conjugates of triazacyclononane hydroxypyridinone (TACN-HOPO) Gd(III) complexes within hydrophobic particles, formulated from pH responsive polymers, should dramatically suppress both water spheres and water exchange rates to the contrast agent to achieve the OFF state or contrast silencing. The pH responsive polymeric particles should release the macromolecular MRI agents thereby allowing optimal water exchange rates. The protein is used to fulfill two roles; provide a large hydrodynamic volume needed to entrap the MRI agents, and to decrease the tumbling frequency of the Gd-chelates, which is known to strengthen the MRI contrast agent.

Figure 26:
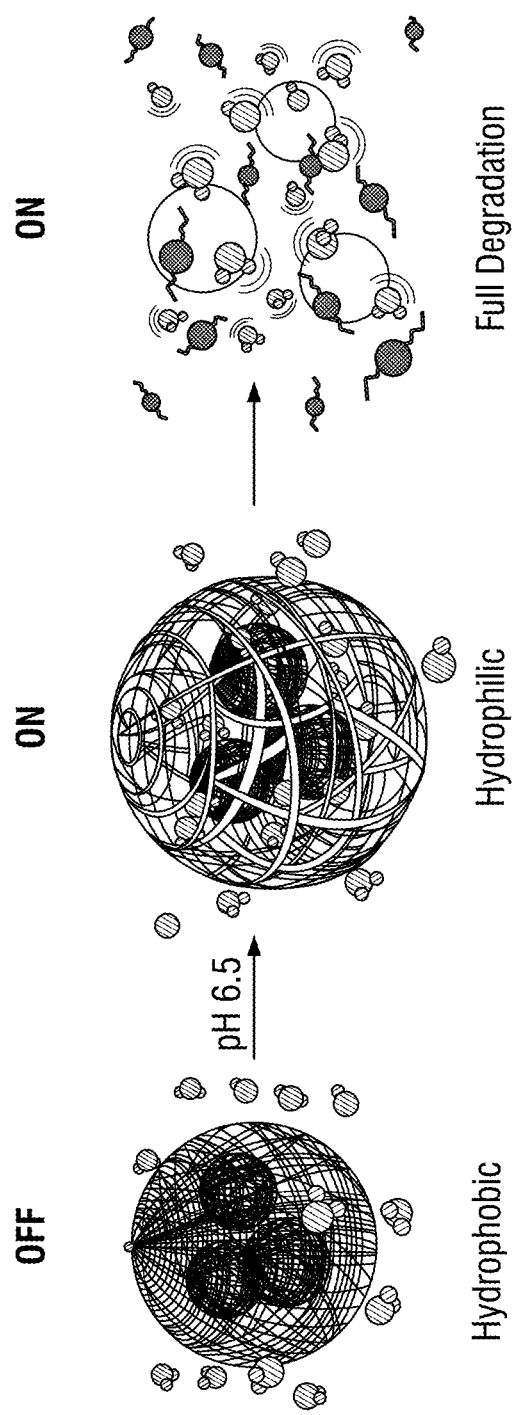
FIG. 26 depicts smart nanoprobes. The contrasting capability of MRI agents is deactivated by embedding in a hydrophobic polymeric particle. As shown here, the polymer become more hydrophilic at pH 6.5 leading to activation of MRI contrast, then at pH 5 it begins to hydrolyze into many fragments.

FIG. 26 illustrates the capacity of a nanoprobe, formulated from the above mentioned polymer, for pH-driven MRI contrast activation. Three stages are highlighted in FIG. 26; the hydrophobic stage should dramatically suppress the water exchange rate while the hydrophilic stage where the nanocarrier is still intact should have a higher relaxivity. In the third and final stage, the nanocarrier is completely degraded in acidic environments, such as endosomal compartments, and may have a unique relaxivity value if Gd was not fully hydrated in the previous state. This is an important stage as the polymer is degraded into innocuous by-products that can be easily excreted.

In addition, other MRI CAs are used with the polymers, nanocarriers, and methods of the present invention. The research designs and methods herein are used to deactivate and reactivate the contrast signal of Magnetic Resonance Imaging (MRI) contrast agents by encapsulating them in dual-response nanocarriers of the present invention thus forming sensing or 'smart' nanoprobes. Thus, embodiments of the present invention relate to formulating Magnetic Resonance (MR) nanoprobes other than gadolinium from polymeric nanocarriers of the present invention and using them to sense and release imaging agents in acidic and/or oxidative environments. The relationship of the polymeric nanocarrier properties on MRI relaxivity is characterized. Nanocarriers are optimized to turn 'off' and 'on' the MR contrast of encapsulated MR agents.

The MR relaxivity properties of the other MR contrast agents encapsulated within polymeric nanocarriers of varying degrees of hydrophobicity/hydrophilicity are characterized. The relationship of the polymeric nanoprobe hydrophobic properties on MRI relaxivity are characterized. This information guides the design and synthesis of polymer-encapsulated MR contrast agents optimized to be "off" when administered and then turn "on" when they encounter diseased tissues.

Manganese Oxide and Iron Oxide nanocarriers can also be coated with hydrophobic polymers to turn off their ability to enhance the relaxation rate of water molecules.

Polymer Degradation is pH-Dependent.

Polymer degradation was monitored in two ways using the GPC. First, the molecular weight of the polymer was determined over time at different pH values. Second, the increase in detected acetone over time was monitored by UV absorption; acetone is a byproduct of polymer degradation. When plotted together in FIG. 27B, the change in acetone detected displays an opposing trend to the change in molecular weight, increasing in equal measure to the decrease in polymer size. As designed, the pH-degradable polymer is able to be degraded fully at pH 7.4 in a little over one day. This rate is increased 3-fold at pH 6.5. However, at pH 10, no degradation is observed.

It is important to note here that ketal degradation this rapid at pH 7.4 has not been shown before. The increased degradation kinetics may be due to the close proximity of carboxylic acids to the ketal moiety in the backbone of the polymer. The proximity of these acids has previously been shown to increase the hydrolysis rate of ketals. It may be possible to tune the degradation rate of this polymer by incorporating hydrophobic components in the synthesis of the polymer should (see, e.g., Paramonov, et al. (2008) *Bioconjug. Chem.* 19, 911-919). Alternatively, changing the distance between the ketal and Gd-chelating moiety may also change the degradation kinetics.

By controlling the degradation rate, the polymer could be designed to have long or short retention times in the blood stream, but changes here could also affect the toxicity of the polymer.

Polymer Degradation Decreases Relaxivity

In a dynamic phantom experiment (FIG. 28) a variety of conditions for the two polymer CAs and recorded T1-weighted images over time were assessed. This was also compared to degraded pH-degradable polymer contrast agent, which after degradation had been adjusted to the appropriate pH values. After 6 h, the pH-degradable CA at pH 6.5 changed significantly, while at 7.4 the intensity decreased only slightly.

To probe the relationship between degradation and relaxivity further, real-time T1 measurements were taken of the polymer solutions using a Bruker minispec mq60 bench top contrast agent analyzer. This machine is able to take rapid T1 measurements over a long duration, allowing for real-time data to be collected. Following data collection, a relationship between T1 and relaxivity can be made, and the relaxivity can be plotted versus time. The relaxivity measurements were then normalized for direct comparison between the two polymer CAs.

Samples were first incubated at 37° C. and various pH values and then measured continuously over time. The control polymer CA showed no change in relaxivity over time at any of the pH values investigated. Similarly, the pH-degradable polymer CA was shown to have a constant relaxivity with time at pH 10. Under these same conditions, the molecular weight should not change (see FIG. 27A). However, at pH 7.4 and pH 6.5, the pH-degradable polymer showed a decrease in its relaxivity with time. This is consistent with the GPC data showing polymer degradation at those pH values.

At pH 6.5, the relaxivity ceases to decrease at approximately 3.7 h, while at pH 7.4 it ceases to decrease at 17 hours; the relaxivity in both conditions is ~3.8 mM−1s−1. This value is slightly higher than the relaxivity for Gd-DTPA as measured, which was $3.64\pm0.12$ mM$^{-1}$s$^{-1}$. Interestingly, these two times are shorter than the time measured for the polymer to fully degrade by GPC; 6 and 24 hours at pH 6.5 and 7.4 respectively. As the polymer CA is degrading, it will form small oligomers. These small fragments will not have any benefit of a long macromolecular tumbling frequency, and should very closely resemble completely-degraded contrast agent. Thus, before total polymer degradation, it would be expected that the relaxivity should cease to decrease, which is what was observed.

The relaxivity measurements obtained for our polymer CAs are similar to other polymeric contrast agents and peptide-based contrast agents used by others, while lower than a conjugated polymer contrast agent used by others, suggesting that this relaxivity is expected from conformationally-unrestricted polymer chelates.

Additional Polymer Considerations and Improvements

Both polymers were chelated in similar conditions, above pH 10, because the pH-degradable polymer CA could be degraded below pH 10. The downside of chelation at this pH is that Gd is not very soluble, and thus the chelation required three days. Using similar polymers, others have shown that the chelation can be completed in only a few hours at pH 6. After chelating the two polymers, insoluble Gd is removed by centrifuging and soluble, un-chelated Gd is removed by the addition of Chelex 100.

Also, the choice of buffer used during chelation is critical. Initially, 100 mM $K_2HPO_4$ was used as the chelation buffer at pH 9 but may have produced some polymer degradation. To prevent degradation, the buffer was switched 100 mM $Na_2CO_3$ with the pH above 10. However, when the polymers were analyzed by our bench top CA analyzer, a slow decrease in relaxivity over time for the control polymer CA was observed. GPC data on these same polymers showed the expected degradation profile; namely, that the control polymer remained at a constant molecular weight and the pH-degradable polymer degraded at the appropriate conditions. The presence of carbonate in the final solution might have caused small amounts of carbon dioxide to be produced over time. This could slightly lower the viscosity, causing a decrease in relaxivity over time by increasing the molecular tumbling frequency. Each time that the chelation step was done in a potassium phosphate buffer, even when the pH was adjusted to >10 by KOH addition, the expected relaxivity profiles were seen over time, and therefore the use of sodium carbonate during chelation was ended.

Figure 29:
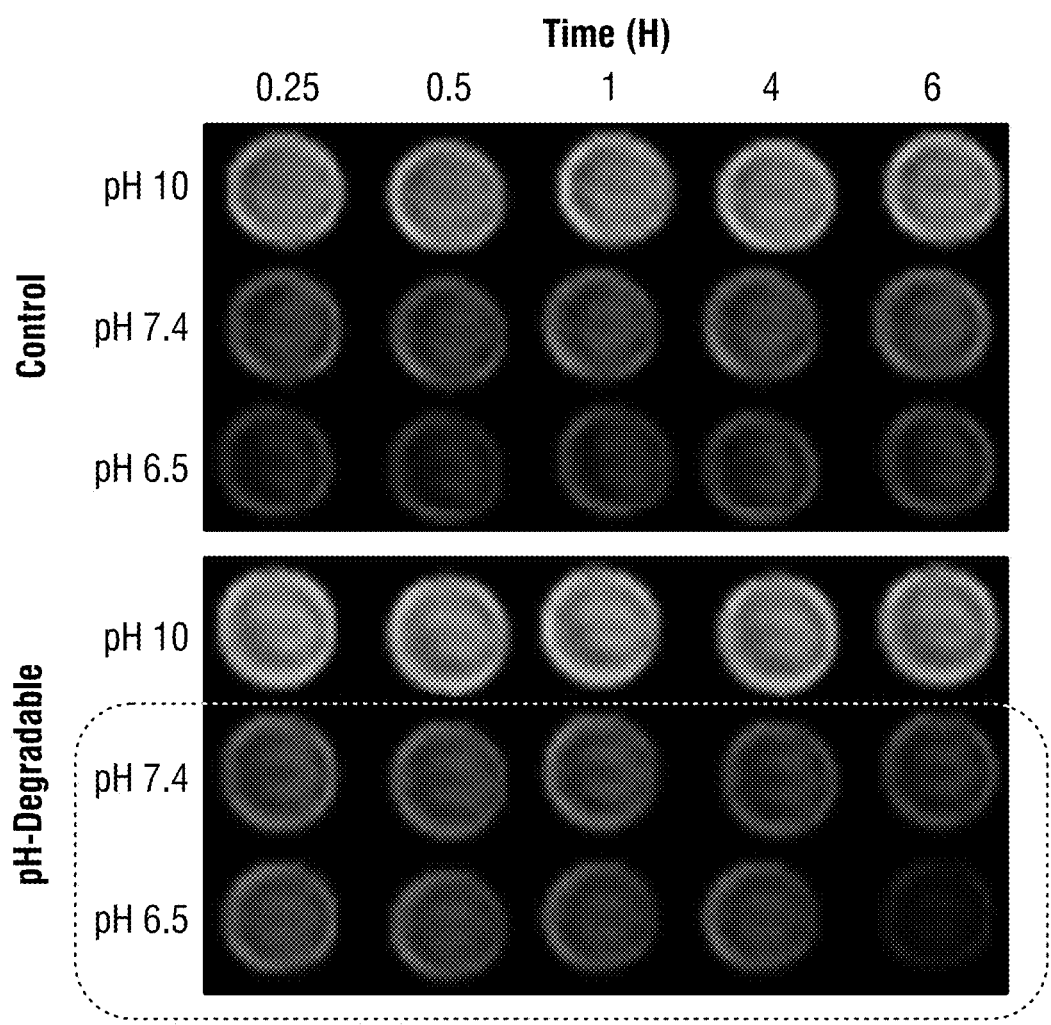
FIG. 29 depicts phantom images of 0.5 mM solutions of the polymer contrast agents at different pH values. The dashed box highlights the two solutions that are designed to change with time.

The polymer CAs described herein, specifically the control polymer CA, show a pH-dependent relaxivity, as was seen in the dynamic phantom experiment in FIG. 29. At pH 10, the control polymer CA is significantly brighter than at pH 7.4, which is in turn brighter than at pH 6.5. Bench-top relaxivities confirmed a pH-dependent relaxivity.

This result is in contrast to a dendrimer-based contrast agent, which shows an increase in relaxivity upon a decrease in pH due to a more ordered and extended structure at these low pH values. Alternatively, at higher pH values, strong intermolecular association could occur, which would lower the degrees of freedom of the system and increase relaxivity. Relaxivity values for Gd-DTPA have been shown previously to be pH-dependent, and polymers of the present invention are a related system. Finally, each pH measured is achieved by using a combination of different potassium phosphate buffers, which implies that each polymer solution has a different buffer concentration. Buffer concentration can also lead to relaxivity changes by changing the viscosity. Although the starting relaxivity of the data herein might not be identical, it is important to note that it still demonstrates a change in relaxivity over time.

In the description above, the pH-degradable contrast agent is prepared by reacting a ketal diamine with the amine-reactive, commercially available DTPA-bisanhydride using readily available components. Karfeld-Sulzer and coworkers have previously shown that a larger, higher molecular weight polymer has a higher ionic relaxivity. Therefore, in some embodiments molecularly-engineered polymers are generated with a higher molecular weight using a different the synthesis route. Such a pH-degradable polymer CA would have a more dramatic decrease in ionic relaxivity upon degradation if its initial relaxivity was at a higher value.

Other embodiments of the present invention are made by selecting a different metal chelating unit. DTPA-bisanhydride reacts with amines to form DTPA-bisamides, which are less stable than other Gd-binding FDA-approved ligands. A similar Gd-DTPA-bisamide to those described above has a stability constant (log K) of 16.84, while Gd-DTPA itself has almost a six-fold higher stability constant (log K of 22.46). Thus, other pH-degradable polymer CAs can be used within the teachings of the present invention.

In another embodiment directed at increasing the stability and lowering the toxicity of compounds of the present invention, DTPA-bisanhydride is replaced with a synthetically-generated unit. This unit would have two distinct features: (1) on one side, two amine-reactive units allow it to react with the ketal diamine, and thus form polymers; (2) on the other side, a DOTA (1,4,7,10-tetraazacyclododecane-1,4,7,10-tetraacetic acid) chelate allows for complexing with Gd. DOTA and DOTA-modified chelates are the most stable, having stability constants of over 23, up to 25.3. Although involving a more complicated synthetic route, a higher stability chelate attached to the pH-degradable polymer improves the efficacy of the present invention when used as an in vivo contrast agent.

In Vivo Properties

Figure 30:
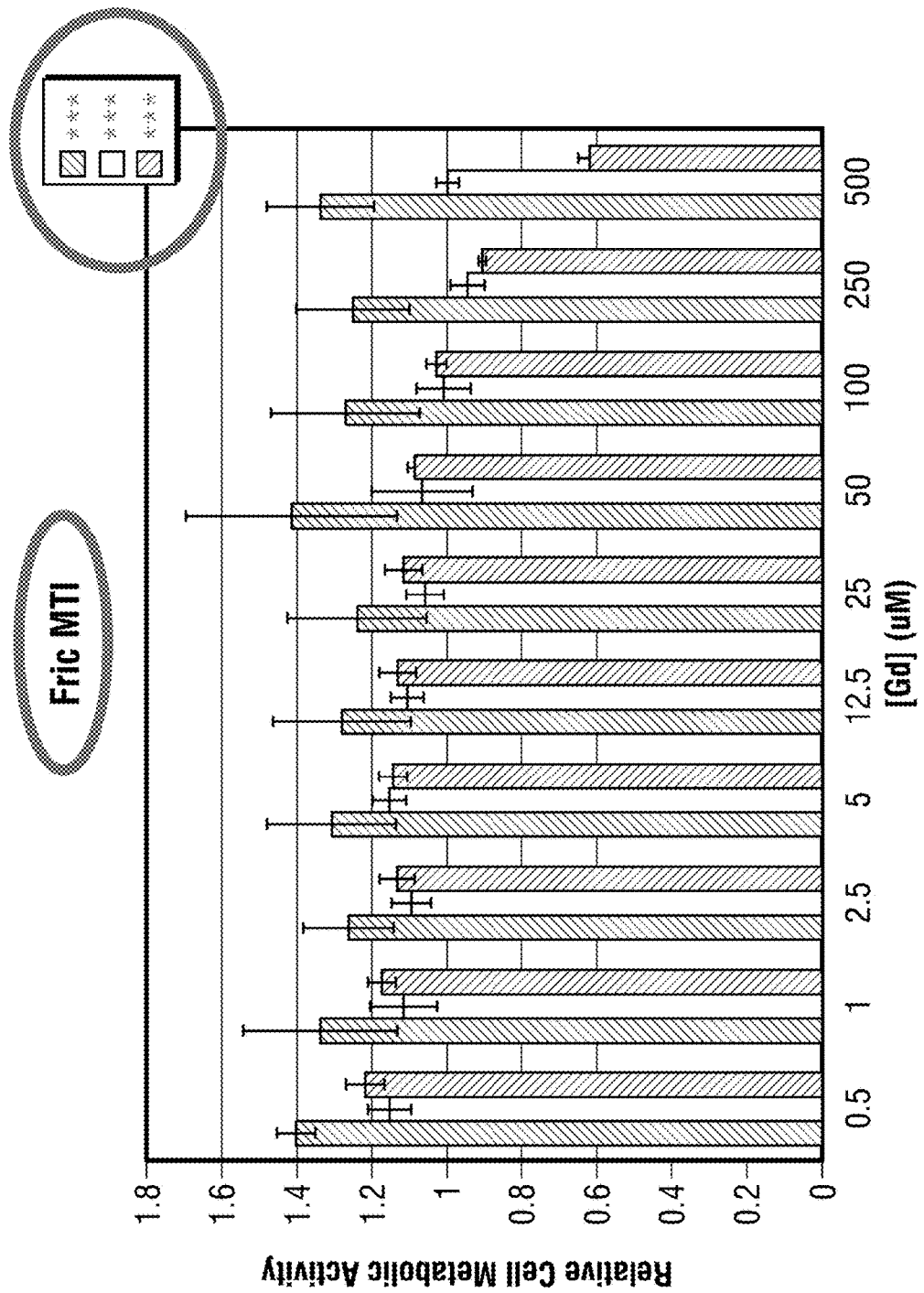
FIG. 30 plots MTT assay results of polymer cytotoxicity.

The toxicity measured by the MTT assay (see FIG. 30) shows only moderate polymer cytotoxicity when incubated with cells for 24 hr. This time is significantly longer than the polymers would reside in vivo at the stated concentrations due to rapid clearance of our polymer CAs shown in our in vivo results. In fact, most of the observed toxicity may be due to buffer concentrations. When two separate solutions of the control polymer were prepared at the same Gd concentration but different buffer concentrations, the solution prepared at a higher buffer concentration showed significantly higher cytotoxicity (5% metabolic activity compared to 99%). Therefore, further modifications of the polymer structure of the CA are capable of decreasing its cytotoxicity.

In further embodiments of the present invention, prior to injection, the buffer concentration is reduced by either using buffer exchange column or dialysis against milliQ $H_2O$. In other embodiments, volatile buffers such as ammonium bicarbonate are used during the synthesis and chelation step. These buffers would be removed during lyophilization, leaving behind only polymer CA, which could then be subsequently resuspended in any buffer at the concentration desired.

In summary, some embodiments of the present invention relate to the synthesis of a polymer contrast agent which can rapidly degrade at physiological pH. This polymer contains acid-labile ketals in the backbone, allowing it degrade by hydrolysis. Degradation at pH 7.4 is catalyzed by the close proximity of these ketals to the carboxylic acids present in the polymer. This polymer CA shows an ionic relaxivity similar to other CAs found by others. The relaxivity change of the polymer CA was monitored over time, and shows a decrease to the same relaxivity at two separate pH values, indicating an inherent monomer relaxivity.

In vivo, the contrast agent of the present invention performs in a similar fashion to Magnevist. The intensity measured in various organs is comparable to Magnevist, but at only half the Gd concentration. Furthermore, when the Gd concentration was measured after injection, our pH-degradable CA shows a similar clearance from the blood pool as Magnevist. Contrast agents of the present invention are improved by several methods, among them: (1) optimizing the buffer during preparation, and (2) using a more stable, less toxic chelating group. The pH-degradable macromolecular contrast agent of the present invention combines the advantages of high relaxivity with the ability to be degraded and rapidly cleared from the body.

Thus, the system of the present invention provides a means for the administration of hydrophilic and hydrophobic payloads into target areas of the human body. These novel systems may also function to sense and image early stages of metabolic diseases and inflammation.

Methods of Polymer Synthesis and Subsequent Analysis

Synthesis of polymer was done by preparing an acid degradable diamine as per the literature. (ref 2-25) Diamine (0.38 g, 2.3 mmol) and 1.0 g (9.3 mmol) of anhydrous sodium carbonate was taken with 15 ml of DMSO in a 40 ml vial. DTPA-bisanhydride (0.85 g, 2.3 mmol) was added portion-wise to the reaction mixture capped with a Teflon® cap and purged with nitrogen. To this, 0.1 ml of triethylamine was added using a syringe and the contents were stirred for 24 h at room temperature. The polymerization was quenched by adding 10 ml of 1% sodium carbonate and the polymer was precipitated into 300 ml of acetone to give 3.00 g polymer with sodium carbonate. 0.5 g of this crude was re-dissolved in 10 ml of water and dialyzed against 0.1 M $K_2HPO_4$ (adjusted to pH 10 using KOH) using a 6000-8000 MWCO membrane for two days. The solution was lyophilized to give the polymer. The control polymer was synthesized similarly using commercially available ethylenediamine (0.192 g, 3.2 mmol) and DTPABA (1.14 g, 3.2 mmol).

Polymer Preparation for Relaxivity Experiments

The lyophilized polymer was then added to a 40 ml glass vial along with an equal weight of $GdCl_3.6H_2O$. 100 mM $K_2HPO_4$ was added to give a final concentration of polymer and $GdCl_3.6H_2O$ of 20 mg/ml and the pH of the solution was adjusted to 10.2-10.4 with KOH. The mixture was stirred at room temperature for 3 days. The solution was then centrifuged at 3,000 rpm for 5 min to remove insoluble Gd and the supernatant was removed. To remove free Gd from the solution, Chelex100 was added to the solution at 100 mg/ml. After stirring for an additional 90-120 min, the solution was centrifuged at 3,000 rpm for 5 min. The supernatant was removed, filtered through a 1 μm syringe filter, and lyophilized. The resulting powder was crushed and used directly in relaxivity experiments. The initial concentration of polymer and buffer salts pre-lyophilization was estimated based on the volume lyophilized and the weight of both components after lyophilization. The Gd content of the polymers was determined by ICP-AES. A dilute solution of polymer was prepared in 1×PBS, and further diluted into milliQ water and a final concentration of approximately 0.4% $HNO_3$.

In Vivo Imaging

Female Swiss-Webster mice used.

The pH-degradable polymer was first concentrated to reach 25 mM Gd. Next, the polymer was added into a Micro Bio-Spin column P-6 (Bio-Rad; Hercules, Calif.) that had previously been exchanged 4 times with 1×PBS. The resulting filtrate was injected into the mice at approximately 0.5× clinical dose (0.05 mmol/kg). The concentration of the injected polymer was measured by ICP-AES.

The control polymer needed to be concentrated by a higher amount to reach 25 mM Gd. In order to remove most of the highly-concentrated buffer, a 25 mM [Gd] solution (5 ml) of control polymer was placed in a 1000 MWCO dialysis membrane and dialyzed against milliQ water (exchanged 3 times) for 24 h. The resulting solution was filtered through a 1 μm filter, lyophilized, and the resulting powder concentrated into 1×PBS. The Gd concentration was then measured by ICP-AES.

MRI scans were taken with the following protocol. The mice were anesthetized using isoflurane gas and placed on a dedicated bed along with a respiration monitoring device. Mice were then placed inside the dedicated whole-body coil at the center of the magnet. Over the duration of the experiment, the mouse is kept under anesthesia. A T1-weighted 3D Gradient Echo sequence was then ran with the following parameters: TR=30 ms, TE=1.7 ms, flip angle=50°, number of excitations=2. Scans were run prior to injection, and at defined time points post-injection.

In Vivo Gadolinium Concentration Profile

Female Swiss-Webster mice were injected. Extracted blood was diluted between 100 and 500 times in milliQ $H_2O$ and approximately 0.4% $HNO_3$. The Gd concentrations from these samples were then measured by ICP-AES.

Gel Permeation Chromatography

Figure 27A:
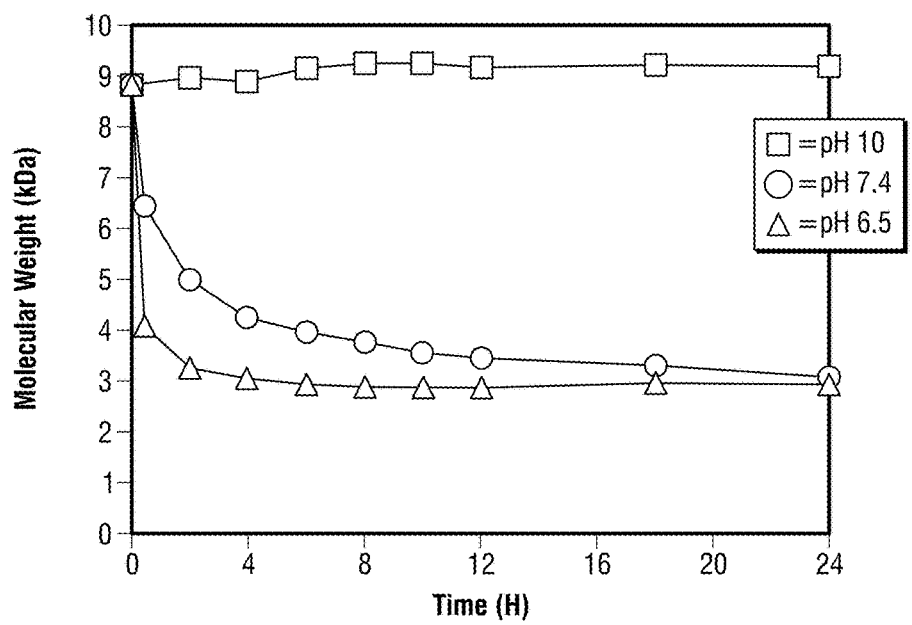
FIGS. 27A and 27B depict gel permeation chromatography results, where

To assess the kinetics of degradation of the polymer CAs, their molecular weight was measured as a function of time at various pH values by GPC. FIG. 27A shows the molecular weight change during the course of the experiment. At pH 10, the polymer shows no mass change, indicating that it remains intact at and above pH 10. However at pH 7.4, degradation of the polymer is clearly visible, with the polymer fully decaying in 24 h. At pH 6.5, the degradation is even more rapid, ceasing to change in molecular weight at approximately 8 h.

Figure 27B:
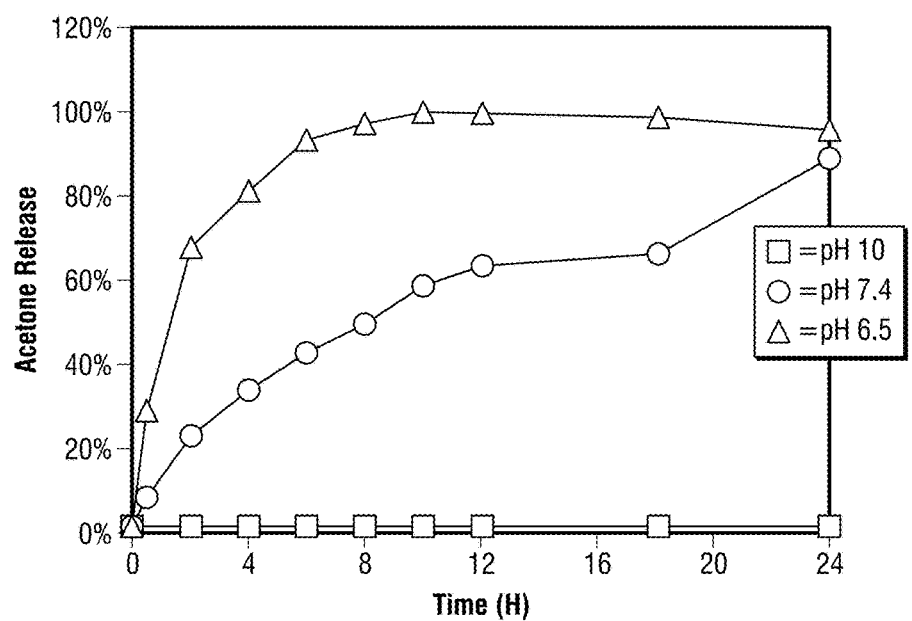

The acetone formation over time was also simultaneously measured in these polymer solutions by UV spectroscopy. Acetone release is an indication of ketal hydrolysis, and therefore polymer degradation. Acetone release is shown in FIG. 27B. For the pH-degradable polymer CA, no acetone release is observed at pH 10, confirming that the polymer remains intact at that pH. At pH 7.4 and pH 6.5, acetone is released. Lower pH values increase the rate of acetone release, which confirms that the polymer degrades more rapidly at lower pH values. Maximum acetone release at pH 6.5 is observed at 10 h, while at pH 7.4, the acetone release is at 90% of maximum. The acetone release results suggest that the molecular weight change graphs slightly underestimate the time for full degradation.

Polymer Relaxivity

After polymer preparation, the concentration of Gd was measured for a given polymer mass. At its original concentration, the pH-degradable polymer contained 4.56±0.06 mM Gd, while the control polymer contained 1.64±0.01 mM Gd. The Gd content in two polymer solutions could be adjusted by concentrating or diluting the polymer solutions, allowing a wide range of concentrations to be prepared as necessary for relaxivity measurements.

Various concentrations of both the pH-degradable and control polymers were placed in a home-made 700 µl centrifuge tube holder within the Aspect M2. An inversion-recovery experiment was performed with varying inversion times. Following image acquisition, a custom Matlab program is used to measure the intensities of each tube for a given inversion time and correlate it to give the T1 relaxation times for each tube at each Gd concentration, which allows inverse T1 times to be generated. FIG. 28A shows the relationship between inverse T1 time and Gd concentration. The slope of this relationship is the relaxivity per Gd, also known as the ionic relaxivity. FIG. 28B shows one of the T1-weighted images at a particular inversion time. An ionic relaxivity of 8.16±0.25 $mM^{-1}s^{-1}$ and 8.72±0.49 $mM^{-1}s^{-1}$ was obtained for the pH-degradable polymer and control polymer respectively.

Dynamic Phantom Imaging

During polymer degradation, the ionic relaxivity was expected decrease until it reaches a value similar to that of a single chelated Gd. In order to observe a change in relaxivity versus time during polymer degradation, a phantom image experiment was performed over time. Here, T1-weighted images were taken of 700 µl centrifuge tubes containing three polymer solutions at three pH values: 10, 7.4 and 6.5. These pH values were chosen to be the same as the GPC values so comparisons could be made between polymer molecular weight and relaxivity. The pH-degradable polymer and the control polymer were two of the solutions measured. To check the hypothesis that the degraded polymer solutions should have a similar relaxivity to single Gd chelates, a solution of pH-degradable polymer was prepared at pH 6.5 and incubated at 37° C. overnight to ensure complete degradation. 1 mM solutions of Gd were prepared from these groups of solutions, adjusted to the pH desired, and diluted with water to reach a final 0.5 mM concentration. As two controls, a 0.5 mM Gd-DTPA solution and a buffer solution were also prepared. Because the same Gd concentration is used, intensity in each tube is proportional to the relaxivity. Therefore, a change in relaxivity will lead to a change in intensity.

FIG. 29 shows images of the different solutions over time. The top grouping shows that the control polymer does not have an intensity change over time, which is consistent with the GPC data that shows no molecular weight change over time. The middle grouping, degraded pH-degradable polymer, shows a lower intensity, which is indicative of a lower relaxivity. Furthermore, the intensity of these solutions does not change with time, indicating that the polymer has been fully degraded. In the bottom grouping, the pH-degradable polymer shows an intensity change at both pH 7.4 and 6.5, confirming the hypothesis that polymer degradation leads to a relaxivity change; the solution at pH 10 shows no intensity change as expected from the GPC results.

Relaxivity Change Versus Time

To investigate the change in relaxivity over time at different pH values further, continuous T1 measurements were taken using a bench top contrast agent analyzer. Using this machine, the T1 time of a 200 µl solution in an NMR tube is able to be measured. Furthermore, the measurement duration is short, allowing for a more real-time investigation of the T1 time. Finally, the software allows for sequential measurements to be performed, allowing for over 24 h of continuous T1 data to be taken.

Figure 31:
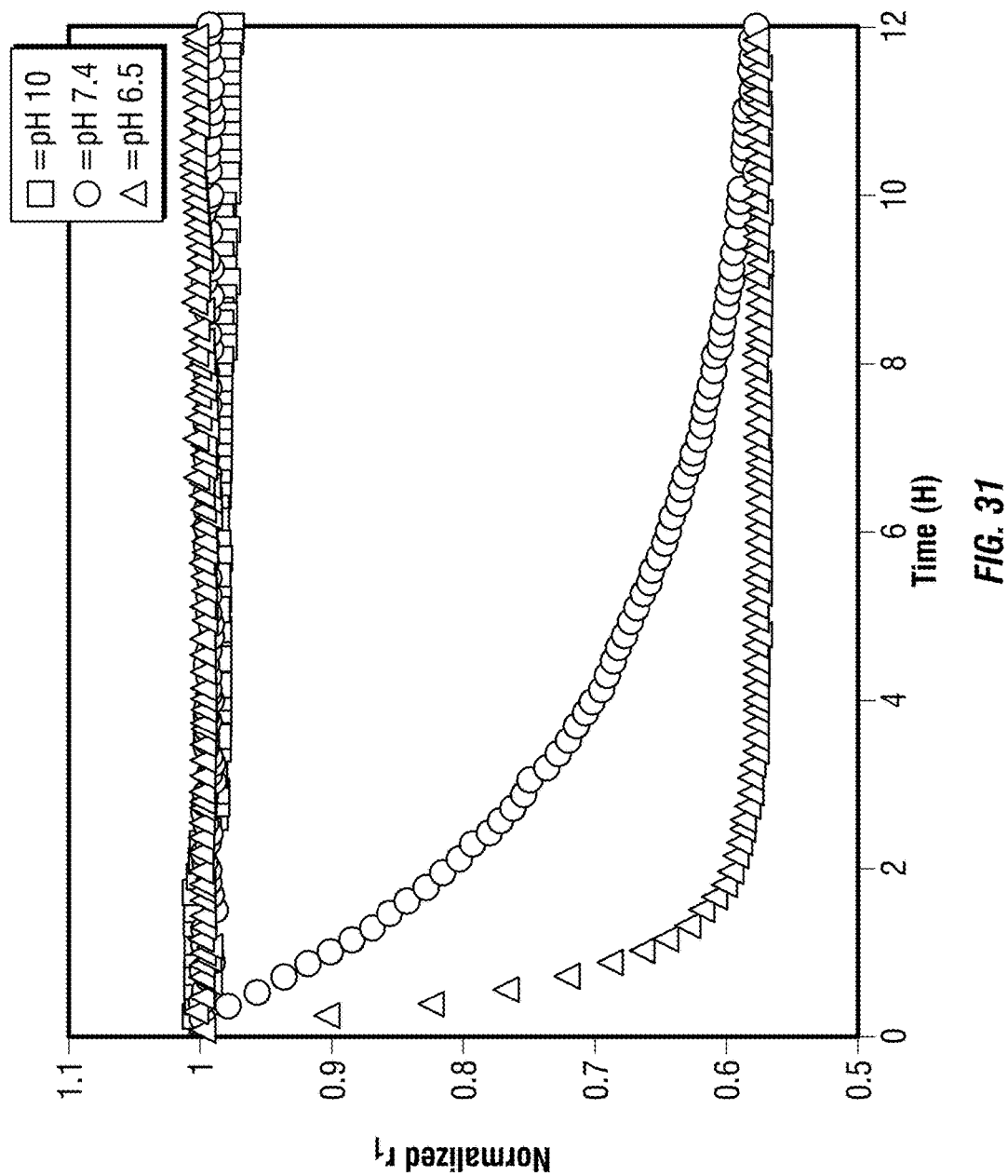
FIG. 31 plots the relaxivity versus time for different pH values of both the pH-degradable and control polymer contrast agents. Shaded circles correspond to the pH-degradable polymer contrast agent while hollow circles correspond to the control polymer contrast agent.

Solutions of both polymer contrast agents were prepared at the desired pH values and pre-incubated for 5 min at 37° C. prior to T1 measurements. After 24 h of measurements, the T1 values were converted to relaxivity values based on the relationship described in the elsewhere. Relaxivity values were then normalized by dividing by the initial measurements, and the results are shown in FIG. 31. Similar to the dynamic phantom experiment described earlier, the control polymer shows no relaxivity change over time at any pH value attempted. The pH-degradable contrast agent is shown to have no relaxivity change in time at pH 10, while decreases to below 60% initial relaxivity over time at both pH 7.4 and 6.5. These results are in agreement with the hypothesis that the relaxivity will change during polymer degradation.

Polymer Cytotoxicity

Various Gd concentrations of the polymer CAs as well as Gd-DTPA were prepared by dilution. Cytotoxicity was measured by a MTT assay and normalized to cells treated only with buffer. The results of the assay indicate that our polymer exhibits only slight cytotoxicity at high Gd concentrations.

In Vivo Imaging

Figures 32A, 32B:
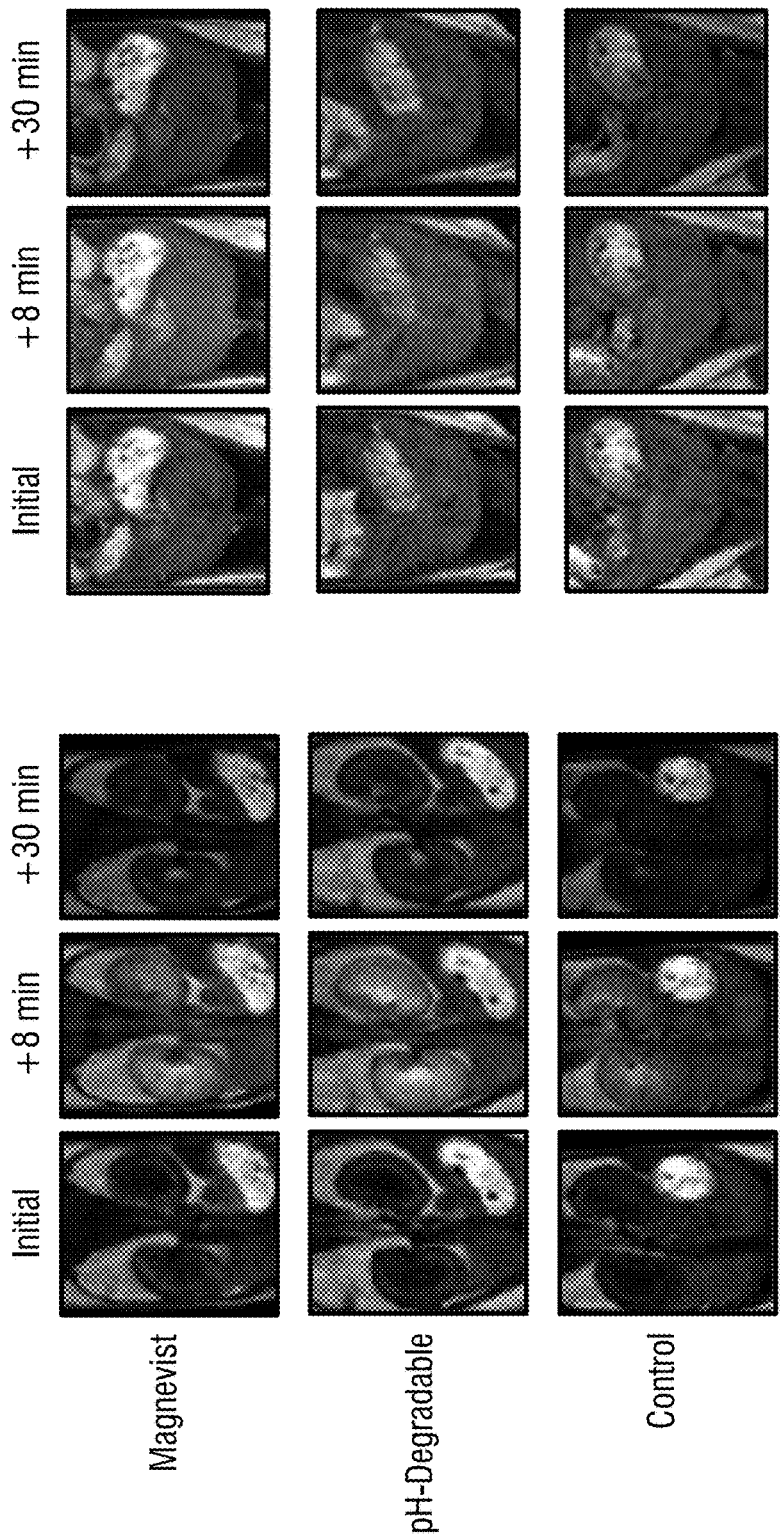
FIGS. 32A and 32B show in vivo MRI images of both polymer CAs as well as Magnevist. Two different slices are shown for each contrast agent initially, as well as two time points post injection, focusing on the kidneys (FIG. 32A) and the liver (FIG. 32B). Images are representative of each triplicate.

Following anesthesia by isoflurane, Female Swiss-Webster mice were injected with either commercially available Magnevist or either the pH-degradable or control contrast agent and imaged. A Gd standard was placed adjacent to the mice in order for post-imaging data normalization. A pre-injection image was first taken to record baseline intensities. Immediately following injection, successive scans were taken over the first hour (7 scans total). A final scan was taken 4 hrs. post injection. FIG. 32 shows representative images taken at various time points for all three contrast agents. These images can be measured qualitatively, and show that a contrast enhancement of the blood and kidneys is readily visible immediately after injection and is decreasing significantly 30 min post-injection.

For quantitative analysis of the MRI images obtained, the intensity in various organs/areas was measured using ImageJ (NIH). These intensities were normalized by dividing by the Gd standard present next to the mice. The results are summarized in FIG. 32. The liver shows the smallest change in signal, while there is an almost doubling of the intensity in both the major artery and kidney immediately after injection. Furthermore, the intensities of all CAs are approximately the same even though both polymer CAs were injected at half the Gd concentration as Magnevist.

Example 5

Gene Delivery

Effective gene delivery tools offer the possibility of addressing multiple diseases and current strategies rely on viruses or polyplexes. Encapsulation of DNA within nanocarriers is an attractive alternative method for gene delivery. In some embodiments of the present invention, nanocarriers with the Logic Gate feature described herein were used for gene delivery. The nanocarriers, composed of a dual pH-response random co-polymer (poly-β-aminoester ketal-2), can undergo a two-step 'in series' response to endosomal pH. First, a hydrophobic-hydrophilic switch occurs followed immediately by rapid degradation. Rapid fragmentation is known to increase cytoplasmic delivery from nanocarriers. Therefore, the Logic Gate nanocarriers of the present invention enable increased gene delivery and expression relative to those nanocarriers that degrade more slowly such as PLGA-based nanocarriers. Passive nanocarrier entry into cells was demonstrated by delivering Cy-5-labeled pDNA-encoding EGFP into HCT116, a colon carcinoma cell line. Flow cytometry analysis showed cells are positive for Cy5-DNA-nanocarriers and produced EGFP expression superior to PLGA nanoparticles. Inhibition of V-ATPases using bafilomycin A1 demonstrates that expression of EGFP is dependent on a drop in pH. The advanced Logic Gate nanocarriers of the present invention offer new therapeutic possibilities in gene delivery and other applications where rapid release is important.

Figure 33:
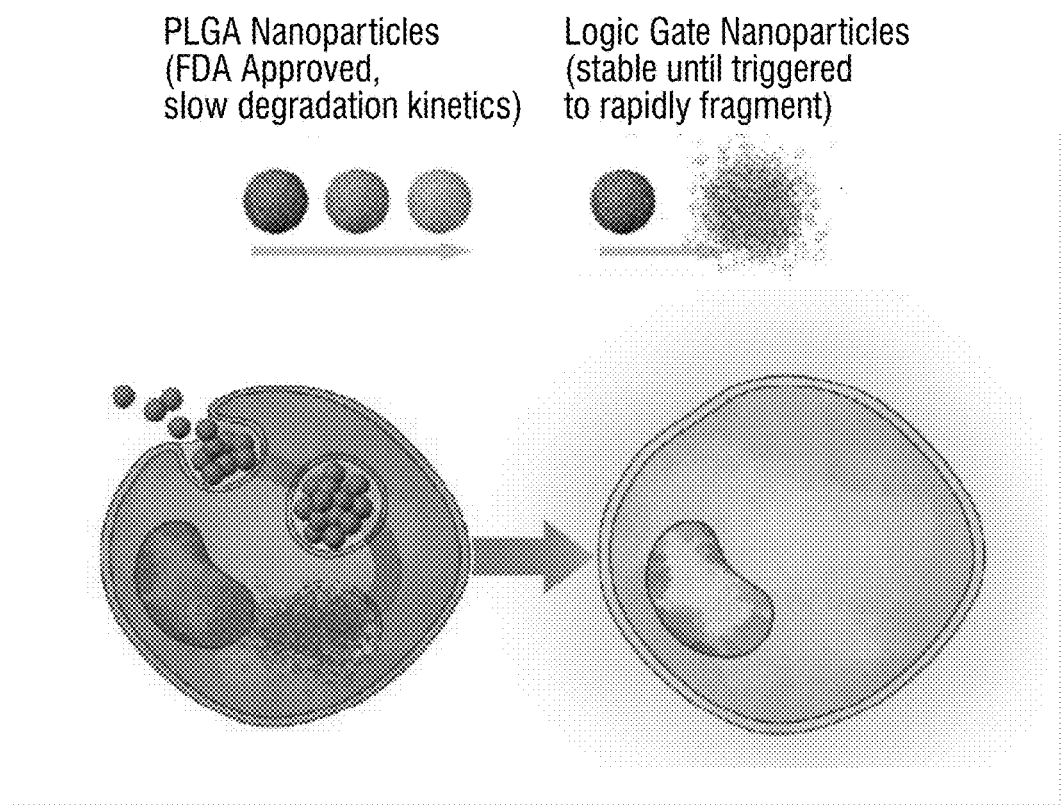
FIG. 33 diagrammatically illustrates the advantages of the Logic Gate Nanoparticles (also known as Logic Gate Nanocarriers) over PLGA nanoparticles.

Some embodiments of the present invention provide a novel gene delivery system using Logic Gate nanocarriers developed with dual pH responsive random co-polymers (poly-β-aminoester ketal-2) (Sankaranarayanan et al. (2010) *ACS Nano* 4, 5930-36). Nanocarriers of the present invention featuring random copolymers as described herein are unique because the amine backbone undergoes a sharp hydrophobic-hydrophilic switch. This leads to an increase in uptake of water (bulk dissolution) and hence an increase in ketal hydrolysis (surface degradation). The nanocarrier formulations are stable for 24 hours in physiological pH, and upon reducing the pH to endosomal levels, pH 5, these dual-responsive nanocarriers undergo a rapid and dramatic fragmentation followed by concomitant release of their payloads (FIG. 33). Nanocarriers of the present invention composed of the dual pH-responsive polymer offer effective endosomal release and expression of encapsulated DNA due to their ability to undergo rapid fragmentation.

DNA Encapsulation and Stability Study

Several obstacles exist to thwart successful gene delivery including DNA packaging, transportation across the membrane, endosomal escape and nuclear transport. However, nanocarriers of the present invention overcome these barriers to effectiveness.

Figure 34A:
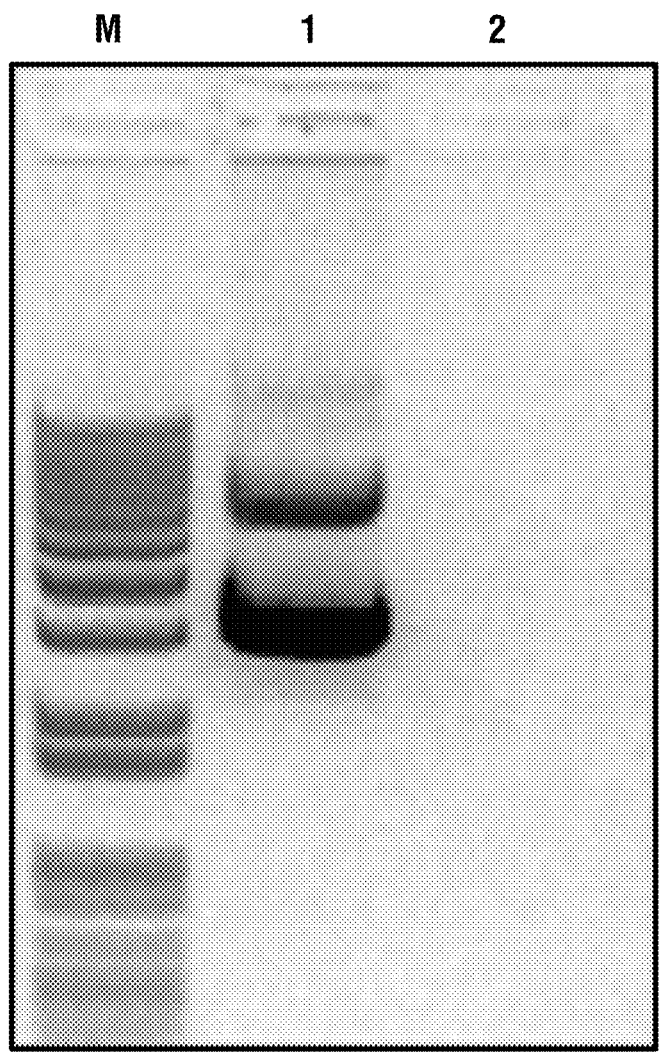
FIGS. 34A-34C illustrate the results of the DNA encapsulation efficiency and release studies, where
Figure 34B:
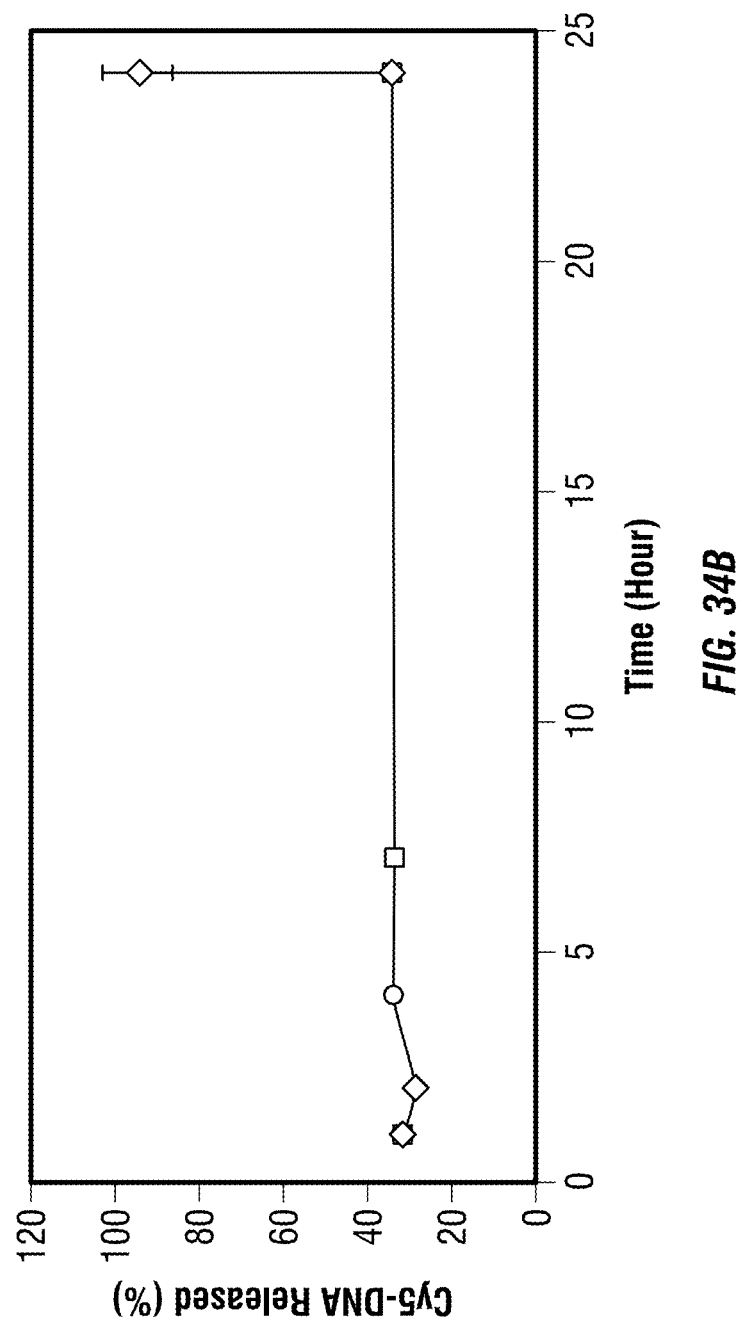
Figure 34C:
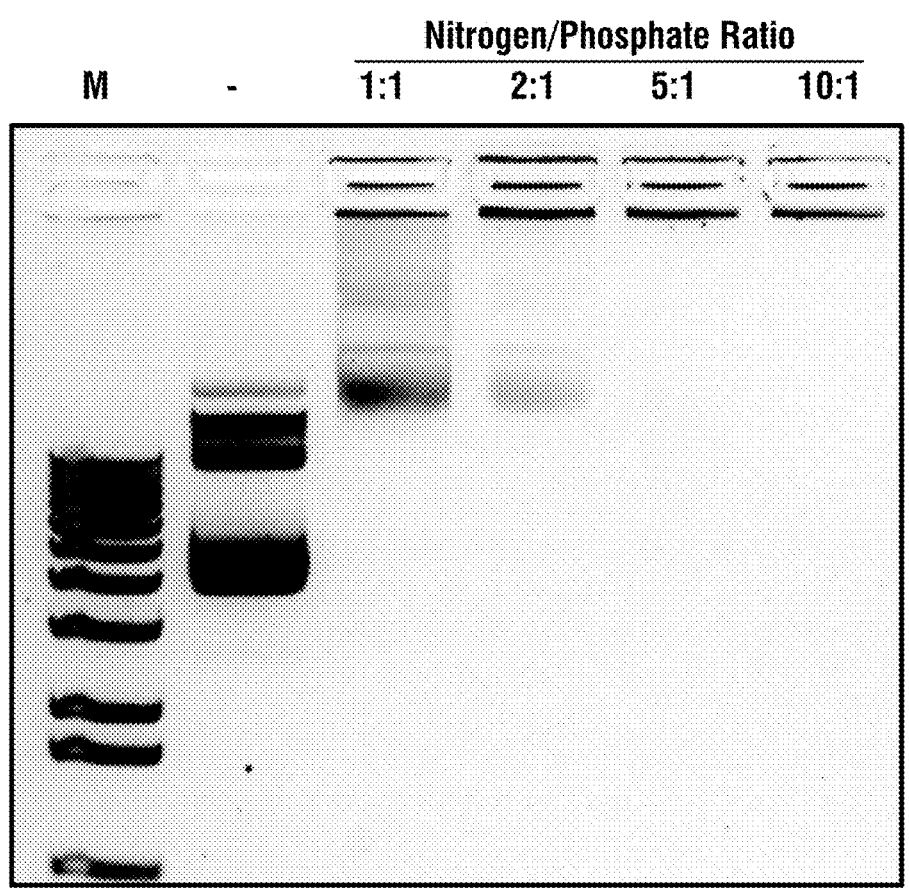

The dual pH-responsive nanocarriers of the present invention containing plasmid DNA were prepared with poly-β-aminoester ketal-2 using double emulsion method. The nanocarriers were approximately 300 nm in diameter and had a zeta potential of −0.562 mV. The supernatant and washes of the preparations were kept and analyzed to estimate the percent of non-encapsulated DNA. The encapsulation efficiency was estimated to be approximately 100% since no detectable DNA was observed in comparison to the starting amount (FIG. 34A). The high encapsulation efficiency may be due to the high nitrogen to phosphate ratio in the nanocarrier-DNA formulation, approximately 1:133 DNA:polymer wt ratio was used. To further support that DNA in the nanocarriers is well complexed, poly β-aminamide ketal, an analogous polymer (that is water soluble), was mixed with plasmid DNA using increasing nitrogen to phosphate ratios and we observed complete complexation at ratios beyond 5 (FIG. 34C).

The release of plasmid DNA from nanocarriers was monitored using Cy5 labeled DNA. The nanocarriers were very stable over a 24-hour period at the physiological pH of 7.4 (FIG. 34B). There appears to be a slight initial burst release of DNA from the nanocarriers but no additional release of DNA is observed. Complete and immediate burst release of the nanocarriers occurred when the pH was dropped to 5, similar to the pH inside an endosome as shown by the curve jump to 100%. The fast fragmentation of the polymer and release of DNA from nanocarriers occurs via a dual chemical response to low pH which causes particles to undergo a hydrophobic-hydrophilic switch and leads to bulk and surface degradation. Particles were also treated with phenol/chloroform to extract the plasmid DNA to ensure that the double emulsion encapsulation procedure did not destroy the plasmid. The double emulsion method used to prepare DNA encapsulated particles caused very minimal degradation of plasmid DNA.

Plasmid DNA Delivery and Expression of EGFP

Figure 35A:
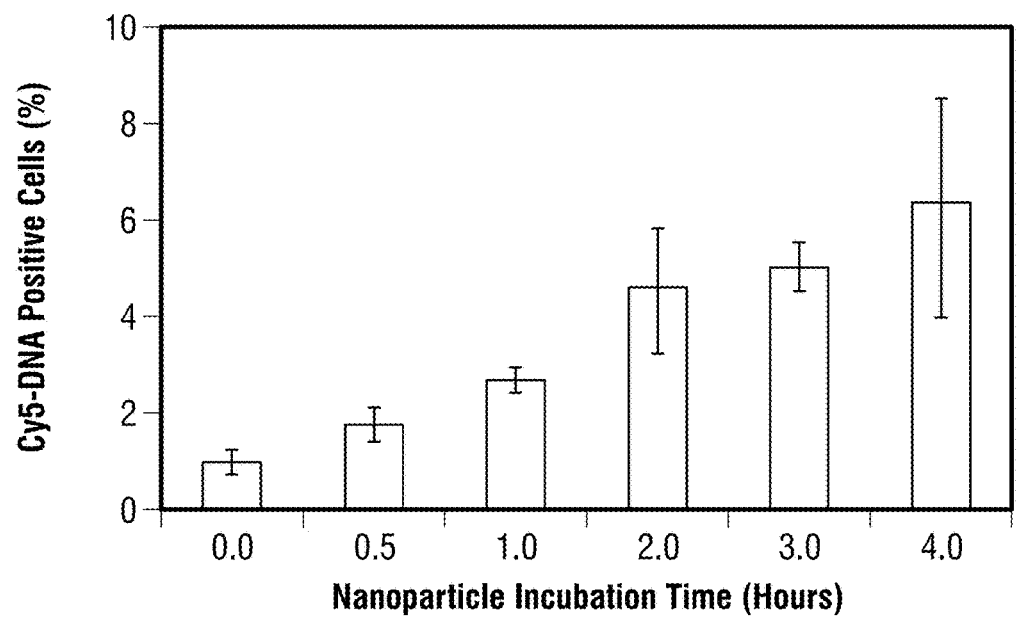
FIGS. 35A and 35B depict Cy5-labeled DNA delivery into cells via pH-responsive nanoparticles: HCT116 cells were incubated with pH-responsive nanocarriers containing Cy5-DNA for 0-4 hours and analyzed by flow cytometry (FIG. 35A) and microscopy after 4 hours (FIG. 35B).
Figure 35B:
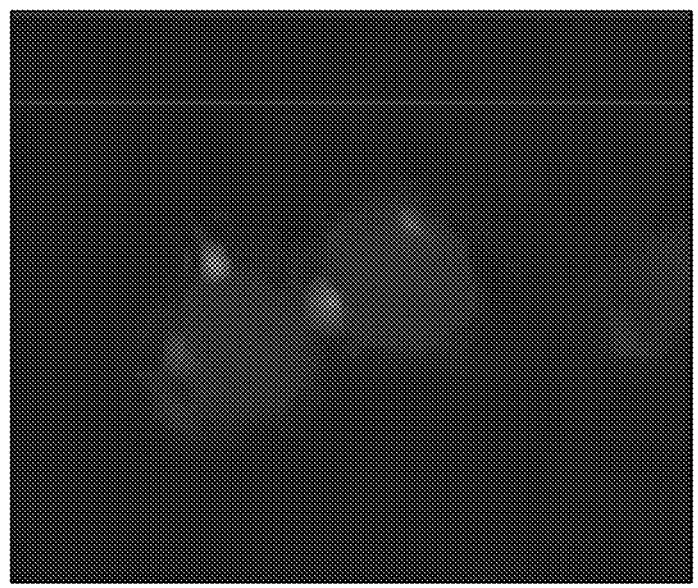

The pH-responsive nanocarriers of the present invention can cross membrane barriers for the proper delivery and expression of proteins such as eGFP. Previous toxicity characterization of these nanocarriers demonstrated a maximum limit of nanocarrier that could be safely delivered to cells (Sankaranarayanan et al. (2010) *ACS Nano* 4, 5930-36). With the formulation method of the present invention and toxicity limits, up to 100 ng of pEFGP was safely delivered per well in 24-well plates. The uptake and transfection efficiency of the dual pH-responsive nanocarriers containing pEGFP was studied using HCT116 cells. First, cell uptake kinetics of nanocarriers using Cy5 labeled pEGFP was analyzed. The nanocarriers were allowed to be passively endocytosed by cells over 4 hours before flow cytometry analysis. About 5% of HCT116 cells were considered positive for Cy5-pEGFP by 3 hours and only a minor increase after 4 hours (FIG. 35A). Although most of the cells are likely taking up a low amount of particles, it appears that only a small percentage of cells are taking up enough particles to detect Cy5 signal over background. Microscopy analysis confirmed that pEGFP was efficiently delivered inside cells and reached the periphery of the nucleus (FIG. 35B). The uptake efficiency of the dual pH responsive nanocarriers by HCT116 cells was very similar to PLGA nanocarriers.

Figure 36A:
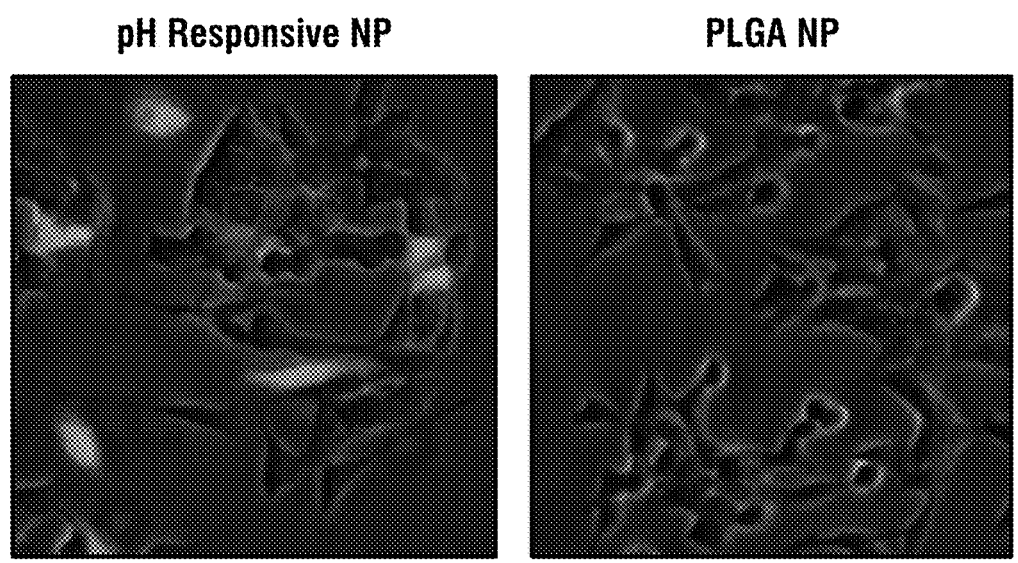
FIGS. 36A and 36B illustrate expression of DNA being superior with pH responsive nanoparticles (NPs) compared to PLGA NPs: HCT116 cells were incubated with NPs for 3 hours, washed, and then incubated in media for 48 hours followed by (FIG. 36A) microscopy and (FIG. 36B) flow cytometry analysis.
Figure 36B:
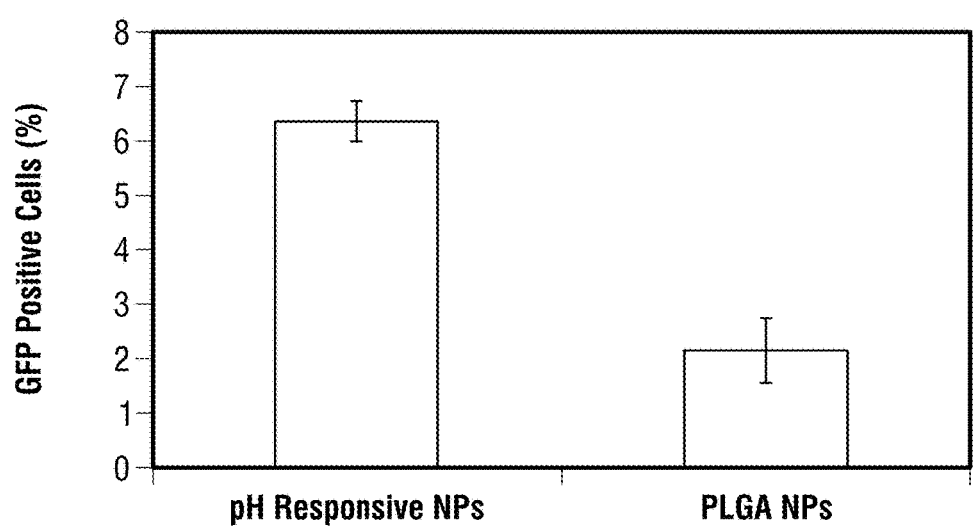

Expression and transfection efficiency of the HCT116 cells was tested by incubating them for 4 hr before washing excess nanocarriers and incubating cells in fresh media for 48 hr. Cells treated with the dual pH-responsive nanocarriers produced intense green fluorescence when analyzed by microscopy. In contrast, cells treated with PLGA nanoparticles containing similar amounts of pEGFP produced relatively low fluorescence (FIG. 36A). Flow cytometry analysis revealed that approximately 6% of the cell population treated with the dual pH responsive nanocarriers had fluorescence intensity higher than 99% of all non-treated cells (FIG. 36B). PLGA-treated cells only had 2% of the cell population with signal intensity above background. The percentage of EGFP positive cells correlates well with the number of Cy5-positive cells, indicating that expression efficiency is high once inside cells.

Figure 37:
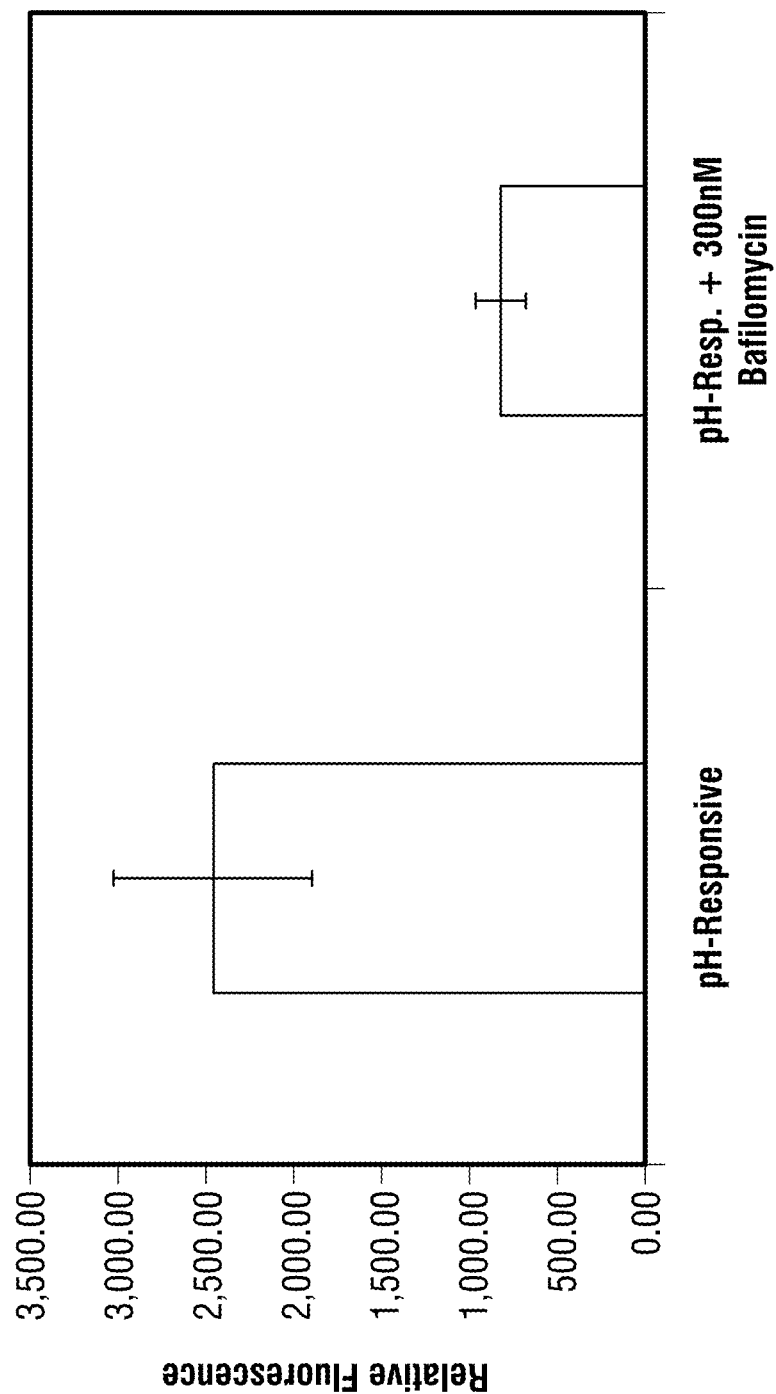
FIG. 37 shows that DNA expression is dependent on endosomal release: Effects of low pH were analyzed by comparing transfection of nanoparticles in the presence or absence of 300 nM bafilomycin A1, a V-ATPase inhibitor.
Figure 38A:
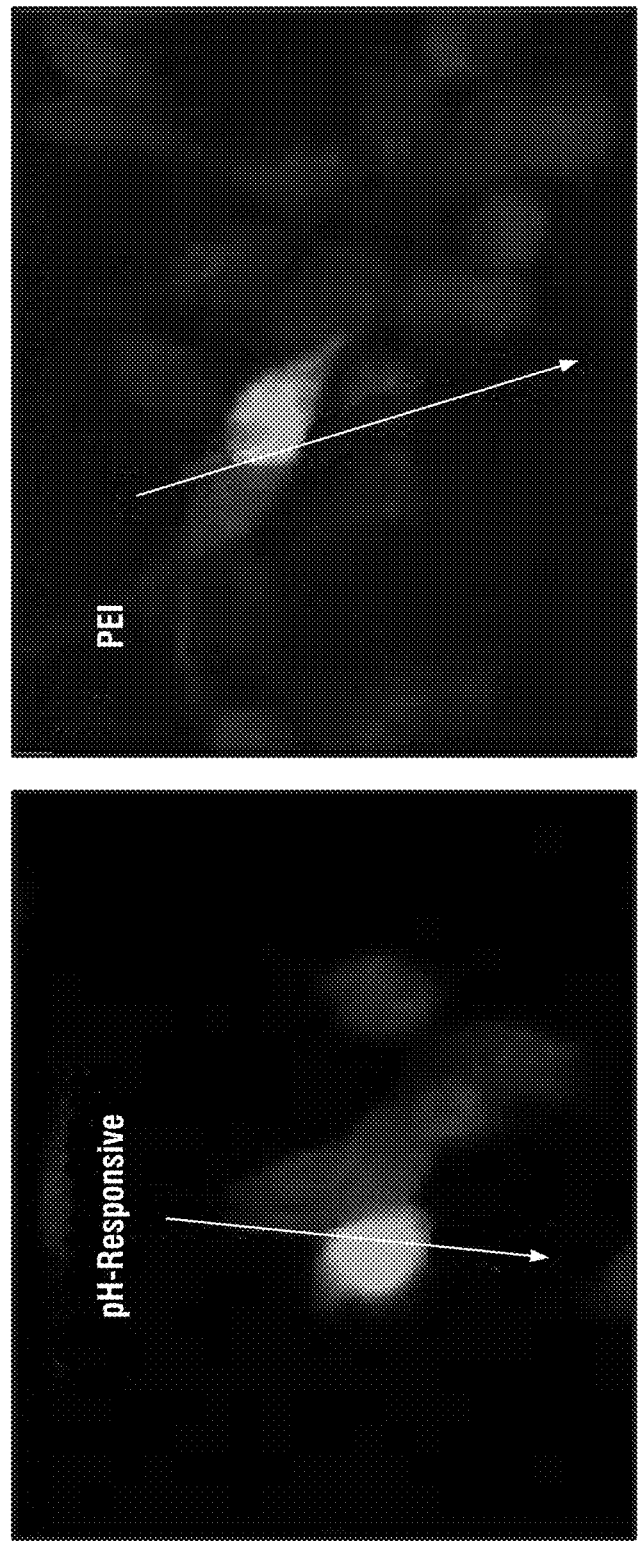
FIGS. 38A and 38B provide an intensity comparison after transfection of 100 ng of DNA using pH-responsive nanoparticles or PEI in 24 well plates of HCT116 cells by microscopy analysis (FIG. 38A) and quantification of the fluorescence intensity through the line shown in the microscopy images (FIG. 38B.)
Figure 38B:
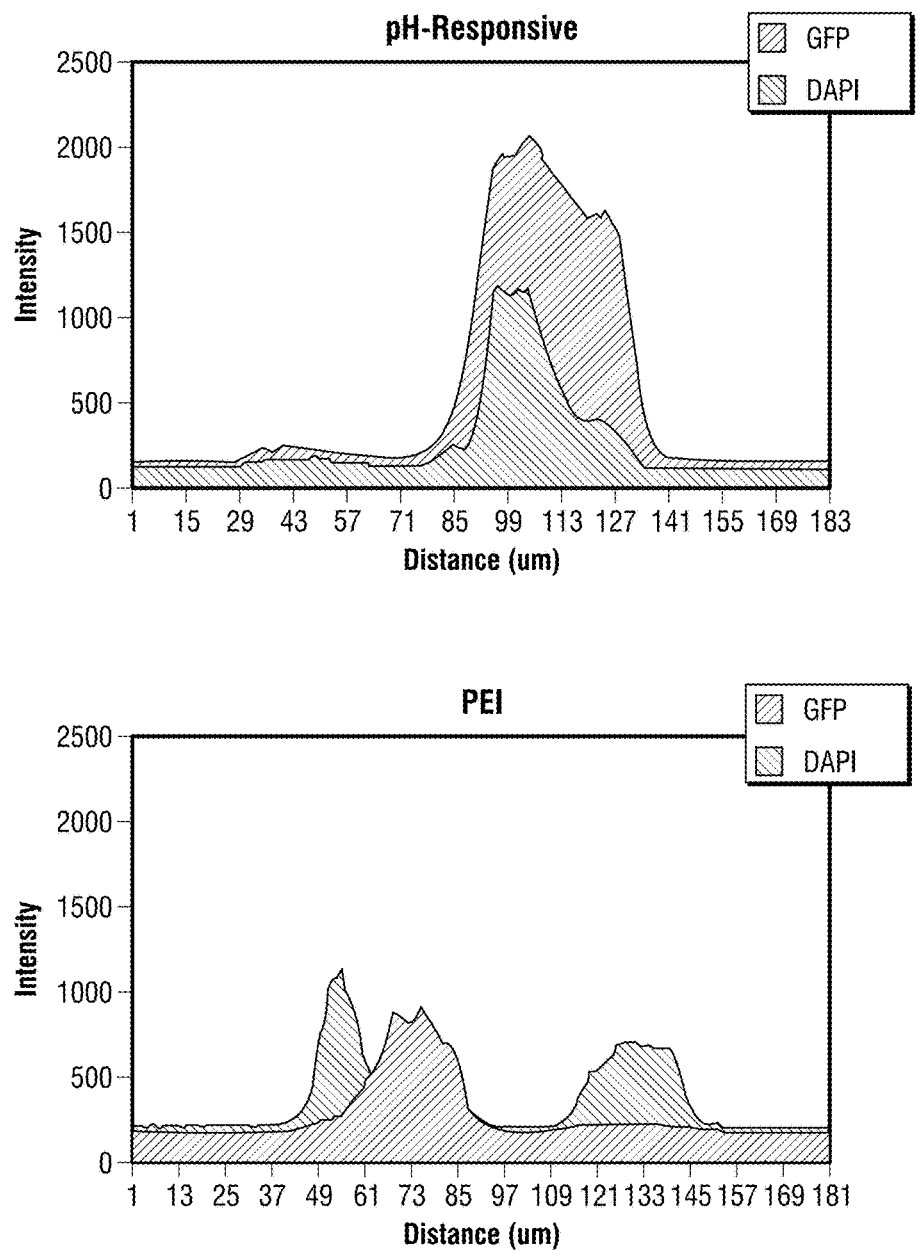

Additionally, comparing the intensity of EGFP-positive cells transfected with nanocarriers of the present invention or with an equal amount of DNA using commercial PEI, nanocarriers can produce similar EGFP expression (FIG. 34). Immediate burst degradation and release of DNA from the dual pH-responsive nanocarriers only occurs in an environment of low pH. The endosome's low pH offers the appropriate stimulus to solubilize the polymer, resulting in an accelerated degradation via ketal hydrolysis. Bafilomycin A1, an inhibitor of V-ATPase, blocks the acidification of endosomes and has been previously used to characterize the mechanism of release of pH dependent polyplexes and nanocarriers. To verify a pH dependency with our system, the transfection efficiency of our dual pH responsive nanocarriers was examined in the presence of 300 nM bafilomycin A1 that is expected to inhibit the pH dependent burst degradation. EGFP expression via nanocarrier delivery in HCT116 cells, measured by mean fluorescence, was affected by the presence of bafilomycin A1, causing 66% reduction in signal relative to non-treated cells (FIG. 37). Expression of EGFP is dependent on the acidic endosomal pH in order for the nanocarriers to degrade rapidly and presumably cause an endosomal burst.

Without being bound by any theory, this is consistent with the main mechanism of action for gene delivery using our dual pH responsive nanocarriers being dependent on a low pH environment.

Due to low toxicity as well as bulk and surface degradation from the novel dual pH-response nanocarriers, higher transfection efficiency is achieved when compared to PLGA, a well known slow degradable polymeric material. The dual response system forms a stable shield as shown by stability experiments and may be suitable for the protection of DNA from nuclease degradation. Our nanocarriers takes advantage of the low pH stimulus within endosomes and allows for rapid fragmentation and DNA release only if particles are endocytosed by cells. Gene transfection was demonstrated by delivering Cy5-labeled pDNA encoding for EGFP into HCT116, a colon carcinoma cell line. The dual responsive nanocarriers produced EGFP expression superior to PLGA nanocarriers Inhibition of V-ATPases using bafilomycin A1 demonstrates that expression of EGFP is dependent on the lower pH of the endosome.

The fast-release system of the present invention offers multiple advantages over slow release formulations. One significant example is that these nanocarriers may also be well-suited for siRNA delivery. siRNA delivery via nanoparticles has already shown promising results using well-characterized polymers like PLGA (Woodrow et al., (2009) *Nat Mater* 8(6), 526-33). Further experiments are underway to test if siRNA can be encapsulated and delivered for fast release and gene knockdown. Furthermore, advanced dual-response nanocarriers of the present invention offer new therapeutic possibilities and can be combined with cell-type specific peptides or antibodies for improved cellular entry and target specificity.

Plasmid Preparation and Cy5 Labeling

The pEGFP plasmid was expanded in overnight cultures of DH5 alpha *E. coli* cells and purified using maxi prep kits (Life Technologies). The DNA was Cy5 labeled using the Label ITTracker Intracellular Nucleic Acid Localization Kit. Labeled DNA was separated from free dye using Micro Bio-Spin 30 chromatography columns (Bio-Rad, Hercules, Calif.).

Synthesis and Characterization of Poly-β-Aminoester Ketal-2

The polymer was prepared by Michael addition of the corresponding diacrylates with trimethyl dipiperidine (Sankaranarayanan et al. (2010) *ACS Nano* 4, 5930-36). Molecular weight: Estimated by size exclusion chromatography against polystyrene standards in DMF/0.01% LiBr with a VWD (variable wavelength detector) at 250 nm. Mw=6300, Mn=2880, PDI=2.18.

Preparation of Nanocarriers

The DNA was encapsulated into the particles using double emulsion method (W/O/W). In a vial, 10 mg of the polymer were dissolved in 300 £gl of DCM. Subsequently, 30 μl DNA solution prepared in Tris-HCl buffer pH 8 was added. The two phases were sonicated for 30 s at amplitude of 2 (MisonixS-4000 cup horn, USA). Then, an aqueous solution of 3 ml 1% PVA in Tris-HCl buffer pH 8 was added and sonicated for two 30 s cycles at an amplitude of 5. The nanocarriers suspension was stirred at 500 rpm under vacuum using a magnetic stirrer to evaporate DCM. Concentrated mode tangential flow filtration system using 500 kDa MicroKros® modules (Spectrum Labs) was used to remove the PVA and free DNA.

The nanocarriers suspension was concentrated and washed two times. Finally, the suspension was lyophilized after adding 5% trehalose. The nanocarriers characterization and properties were in agreement with other results (see, e.g. the present invention and/or (Sankaranarayanan et al. (2010)

ACS Nano 4, 5930-36)). In brief, the particles had an average hydrodynamic volume of 300 nm, 0.3 PDI, and −0.562 mV using dynamic light scattering measurements on a Malvern nanosizer.

Nanocarriers Encapsulation Efficiency

Unencapsulated DNA was collected, lyophilized, and resuspended to determine the amount of DNA using 1% TAE agarose gel. To test the quality of encapsulated DNA, nanocarriers (0.2 ml) in 10 mM Tris HCl (pH8) and heparin (1:100 DNA to heparin) were extracted with 0.2 ml phenol: chloroform:isoamyl alcohol (25:24:1) and spun down at 12,100×g for 20 min. Then, 50 µl of the aqueous layer were diluted with 250 µl buffer and extracted with 300 µl CHCl$_3$. The aqueous layer was separated by spinning down and analyzed by gel electrophoresis.

DNA Release from the Nanocarriers

DNA-Cy5 nanocarriers were resuspended in phosphate buffer pH 7.4. The nanocarriers were left in a shaker at 60 rpm/37° C. Aliquots were taken at different time intervals and spun down at 2K×g/4° C. for 10 min. The supernatant was used to determine the amount of released DNA. After 24 hr, the particles were spun down and resuspended in phosphate buffer pH 5 to test the effect of pH.

Transfection of DNA with Nanocarriers

HCT116 cells were plated at a ~50% density in a 24 well culture plate and allowed to attach overnight. Cells were then treated with 50 to 100 ng of labeled or unlabeled DNA, encapsulated in nanocarriers, for 4 hr. The media was then replaced with 500 µl of fresh media in each well after washing and removing excess nanocarriers. The cells were then incubated for 48 hours and subsequently analyzed by fluorescence microscopy (Nikon) or flow-cytometry (Accuri C6) to detect green fluorescence. For microscopy analysis, cells were placed in wells containing glass cover slips. For flow cytometry, cells were first trysonized for 5 nm followed by two washes with PBS and analyzed immediately. When treated with Bafilomycin A1, a final concentration of 300 nM was added just prior to adding nanocarriers.

Example 6

NIR Imaging

NIR fluorescence imaging uses non-ionizing radiation that can be detected at the femtomolar level; it requires fewer safety precautions than radioactive imaging techniques, and this results in low cost and user-friendly imaging equipment. NIR light can pass through the skin, without damaging tissue, and is least absorbed by water, hemoglobin, oxygenated hemoglobin, fat, and melanin. Additionally, fluorescence from intrinsic tissue components (autofluorescence) is low in the NIR region, resulting in higher signal-to-background ratios, and thus provides excellent contrast. NIR reporters that can non-invasively detect and analyze diseased tissue offer a sensitive, inexpensive, safe and decisive contrast tool to interrogate biological processes in vitro and in vivo. NIR contrast probes are encapsulated in dual-response polymeric nanocarriers of the present invention to form highly sensitive smart NIR nanoprobes.

NIR dyes are known to interact closely with each other to form H-type homoaggregates via face-to-face stacking in aqueous environments and at high concentrations. This agglomeration suppresses their fluorescence intensity and lifetime through non-radiative decay, and thereby minimizes background noise. This property is exploited to create an 'OFF' state. Nanoprecipitation of NIR fluorophores with polymers of the present invention yields nanocarriers that encapsulate NIR contrast agents. When released, the fluorophores drift apart and fluorescence intensity increases and/or activates along with a change in the excited state decay characteristics to the ON state.

Thus, Near Infrared (NIR) nanoprobes are developed from nanocarriers of the present invention, and their ability to sense and release in acidic and/or oxidative environments is demonstrated. Further, the relationship of the polymeric nanocarriers of the present invention properties on NIR fluorescence is characterized. Further, polymeric nanocarriers of varying degrees of hydrophobicity/hydrophilicity are used to encapsulate NIR contrast agents, and the results are characterized.

This information guides the design and synthesis of polymeric nanocarriers optimized to turn 'off' and 'on' the NIR Fluorescence contrast agents.

Example 7

Diagnostic Applications

In the clinical diagnostic arena, the present invention assists with the early diagnosis of disease at which point chances for successful treatment are much higher. Nanocarriers of the present invention containing imaging reagents are administered to a patient. In some embodiments, the lower pH and/or ROS present that causes degradation of nanocarriers of the present invention within the patient provides diagnostic information. In other embodiments, the nanocarriers are targeted to a disease or condition prior to the triggered degradation.

Example 8

Site-Specific Delivery Applications

The present invention assists with the site-specific delivery of pharmaceutical compounds. Nanocarriers of the present invention containing bioactive agents are administered to a patient. In some embodiments, the lower pH and/or ROS present that causes degradation of nanocarriers of the present invention within the patient provides delivers the bioactive agents at the selected site. In other embodiments, the nanocarriers are targeted to a disease or condition prior to the triggered degradation.

Example 9

Polymer and Nanocarrier Characterization

In addition to the experiments and measurements described above, polymers and nanocarriers of the present invention are analyzed by a host of spectroscopic, structural, and biological techniques including, but not limited to, electron microscopy techniques; atomic force microscopy; light scattering; analytical ultracentrifugation; steady-state and time-resolved absorption and emission measurements; X-ray; IR; NMR; chromatography techniques; SEC; MALS; mass spectrometry (MALDI and ICP-MS); elemental analysis; cell culture; confocal microscopy; and two-photon microscopy.

What is claimed is:

1. A nanocarrier comprising at least one polymer having a backbone that is stable at normal physiological pH and/or oxidative conditions, the backbone having a response element adapted to fragment the nanocarrier and a trigger moiety, wherein the trigger moiety activates in response to one of lower pH and reactive oxygen species ("ROS") to trigger the response element, wherein the at least one polymer comprises a repeat unit selected from the group consisting of

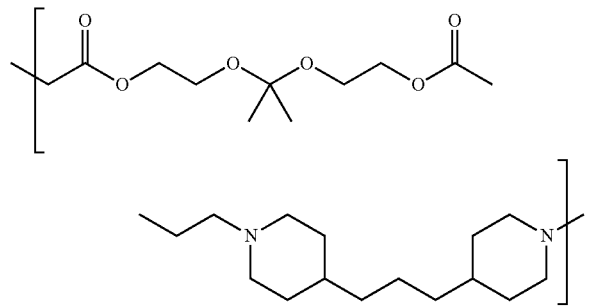

or

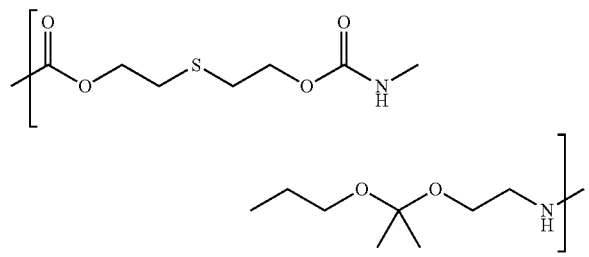

or a derivative thereof.

2. The nanocarrier of claim 1, wherein the nanocarrier encapsulates a payload.

3. The nanocarrier of claim 1, wherein the response element is a ketal group.

4. The nanocarrier of claim 1, wherein the response element is a sulfur atom in the polymer.

5. The nanocarrier of claim 1, wherein the payload comprises a bioactive agent.

6. The nanocarrier of claim 1, wherein the payload comprises an imaging agent.

7. The nanocarrier of claim 1, wherein the payload comprises an MRI imaging agent.

8. The nanocarrier of claim 1, wherein the payload comprises a gadolinium-based MRI imaging agent.

9. The nanocarrier of claim 1, wherein the payload comprises a protein.

10. The nanocarrier of claim 1, wherein the polymer comprises

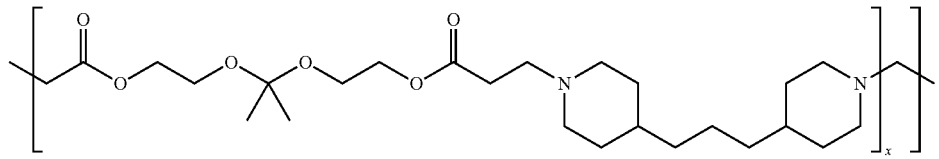

or a derivative thereof.

11. The nanocarrier of claim 1, wherein the polymer comprises

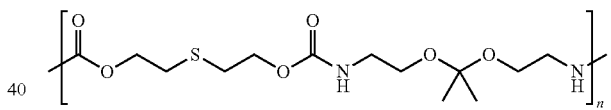

or a derivative thereof.

12. The nanocarrier of claim 1, wherein the ROS is hydrogen peroxide.

13. The nanocarrier of claim 1, wherein the lower pH is within a range of about 7.2 and 5.0.

14. The nanocarrier of claim 1, wherein the payload is protein or DNA.

15. The nanocarrier of claim 1, wherein the trigger moiety is selected from the group consisting of an aminoester responsive to lower pH and a sulfur atom responsive to ROS.

16. The nanocarrier of claim 1, wherein the lower pH is within a range of about 6.5 to 6.0.

17. A nanocarrier comprising:
a payload; and
at least one polymer encapsulating the payload, the at least one polymer having a backbone that is stable at normal physiological pH and/or oxidative conditions, the backbone having a response element adapted to fragment the nanocarrier to release the payload and a trigger moiety, wherein the trigger moiety activates in response to one of pH within a range of about 7.2 and 5.0 and a reactive oxygen species ("ROS") to trigger the response element, wherein the at least one polymer comprises a repeat unit selected from the group consisting of

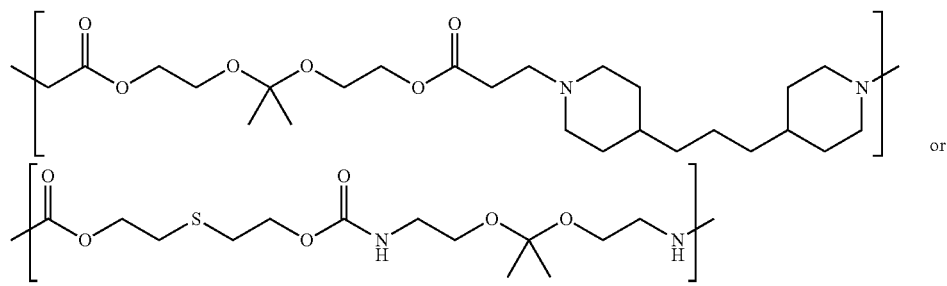

or a derivative thereof.

18. The nanocarrier of claim 17, wherein the payload is selected from the group consisting of a bioactive agent, an imaging agent, a protein, and DNA.

19. The nanocarrier of claim 17, wherein the response element is selected from the group consisting of a ketal moiety and a sulfur atom.

20. The nanocarrier of claim 17, wherein the trigger moiety is selected from the group consisting of an aminoester responsive to lower pH and a sulfur atom responsive to ROS.

* * * * *